US011133113B2

(12) United States Patent
DeBates et al.

(10) Patent No.: US 11,133,113 B2
(45) Date of Patent: Sep. 28, 2021

(54) DATA LABELING SYSTEM AND METHOD OPERATIVE WITH PATIENT AND CLINICIAN CONTROLLER DEVICES DISPOSED IN A REMOTE CARE ARCHITECTURE

(71) Applicant: ADVANCED NEUROMODULATION SYSTEMS, INC., Plano, TX (US)

(72) Inventors: Scott DeBates, Frisco, TX (US); Douglas Alfred Lautner, Frisco, TX (US); Tucker Tomlinson, Sachse, TX (US); James Nagle, Celina, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 16/901,368

(22) Filed: Jun. 15, 2020

(65) Prior Publication Data

US 2020/0398063 A1    Dec. 24, 2020

Related U.S. Application Data

(60) Provisional application No. 62/865,155, filed on Jun. 22, 2019.

(51) Int. Cl.
*A61N 1/372* (2006.01)
*G16H 80/00* (2018.01)
(Continued)

(52) U.S. Cl.
CPC ........... *G16H 80/00* (2018.01); *A61B 5/0031* (2013.01); *A61B 5/7435* (2013.01);
(Continued)

(58) Field of Classification Search
CPC ......... A61N 1/372; H04L 29/06; H04L 12/26; H04N 7/14; G06H 40/67; G06H 10/60
(Continued)

(56) References Cited

U.S. PATENT DOCUMENTS 5,987,519 A    11/1999 Peifer et al.
7,228,179 B2   6/2007 Van Campen et al.
(Continued)

FOREIGN PATENT DOCUMENTS

| WO | 2001/093953 A1 | 12/2001 |
| WO | 2017/165717 A1 | 9/2017 |
| WO | 2019/032788 A2 | 2/2019 |

OTHER PUBLICATIONS

ISA/US, International Search Report, Application No. PCT/US2020/034519, dated Sep. 21, 2020, 8 pgs.
(Continued)

*Primary Examiner* — Melur Ramakrishnaiah
(74) *Attorney, Agent, or Firm* — Norton Rose Fulbright US LLP

(57) ABSTRACT

A system and method for facilitating remote care management involving a patient having an implantable medical device (IMD). Upon establishing a remote care session between a patient controller device and a clinician programmer, wherein the clinician and the patient are remotely located with respect to each other, input from the patient or the clinician may be received via a user interface control associated with a particular functionality or aspect of the remote care session, including audiovisual (AV) communications, remote therapy programming, and related context. Responsive to the user input, a dialog interface is effectuated at one of the patient controller device and/or the clinician programmer. A user characterization label is received via the dialog interface from the user, wherein the user characterization label is indicative of a subjective assessment of the particular functionality of the remote care session, which may be used in generating user-labeled data pertaining thereto.

12 Claims, 42 Drawing Sheets

(51) Int. Cl.
*G16H 20/30* (2018.01)
*G16H 40/67* (2018.01)
*G16H 10/60* (2018.01)
*H04L 12/26* (2006.01)
*H04L 29/06* (2006.01)
*H04N 7/14* (2006.01)
*A61B 5/00* (2006.01)

(52) U.S. Cl.
CPC ..... *A61N 1/37247* (2013.01); *A61N 1/37282* (2013.01); *G16H 10/60* (2018.01); *G16H 20/30* (2018.01); *G16H 40/67* (2018.01); *H04L 43/04* (2013.01); *H04L 65/1069* (2013.01); *H04L 65/80* (2013.01); *H04N 7/14* (2013.01)

(58) Field of Classification Search
USPC ............................................ 348/14.01–14.16
See application file for complete search history.

(56) References Cited

U.S. PATENT DOCUMENTS

| | | | |
|---|---|---|---|
| 8,332,041 B2 | 12/2012 | Skelton et al. | |
| 8,922,330 B2 | 12/2014 | Moberg et al. | |
| 9,215,075 B1 | 12/2015 | Poltorak | |
| 9,288,614 B1 | 3/2016 | Young et al. | |
| 9,348,972 B2 | 5/2016 | Goetz | |
| 9,445,264 B2 | 9/2016 | Young et al. | |
| 9,446,252 B2 | 9/2016 | Benson | |
| 9,649,049 B2 | 5/2017 | Pless et al. | |
| 9,773,060 B2 | 9/2017 | Gerst et al. | |
| 9,855,433 B2 | 1/2018 | Shahandeh et al. | |
| 10,086,202 B2 | 10/2018 | Seim et al. | |
| 10,124,177 B2 | 11/2018 | Kumar | |
| 2002/0072785 A1 | 6/2002 | Nelson et al. | |
| 2002/0082665 A1* | 6/2002 | Haller | G06F 8/65 607/60 |
| 2004/0080610 A1 | 4/2004 | James et al. | |
| 2006/0189854 A1 | 8/2006 | Webb et al. | |
| 2009/0069867 A1 | 3/2009 | Knight et al. | |
| 2009/0326608 A1 | 12/2009 | Huynh et al. | |
| 2011/0171905 A1 | 7/2011 | Roberts et al. | |
| 2013/0154851 A1 | 6/2013 | Gaskill et al. | |
| 2013/0218582 A1* | 8/2013 | LaLonde | A61B 5/686 705/2 |
| 2013/0246084 A1* | 9/2013 | Parmanto | G06Q 50/22 705/2 |
| 2014/0122120 A1 | 1/2014 | Doudian | |
| 2014/0244305 A1 | 8/2014 | Schoenberg | |
| 2015/0089590 A1 | 3/2015 | Krishnan et al. | |
| 2015/0343229 A1 | 12/2015 | Peterson et al. | |
| 2015/0358583 A1* | 12/2015 | Lee | H04N 7/15 348/14.08 |
| 2017/0032092 A1 | 2/2017 | Mink et al. | |
| 2017/0111488 A1 | 4/2017 | Mazar et al. | |
| 2018/0325463 A1* | 11/2018 | Walsh | A61M 16/04 |
| 2018/0361153 A1 | 12/2018 | Heldman et al. | |
| 2020/0398062 A1 | 12/2020 | Ibarrola et al. | |
| 2020/0402656 A1 | 12/2020 | DeBates et al. | |
| 2020/0402674 A1 | 12/2020 | DeBates et al. | |

OTHER PUBLICATIONS

ISA/US, International Search Report, Application No. PCT/US2020/037180, dated Sep. 4, 2020, 6 pgs.

ISA/US, International Search Report, Application No. PCT/US2020/038165, dated Sep. 11, 2020, 8 pgs.

ISA/US, International Search Report, Application No. PCT/US2020/038434, dated Sep. 10, 2020, 8 pgs.

Kim et al., Self-Organizing Peer-to-Peer Middleware for Healthcare Monitoring in Real-Time, Sensors, Nov. 17, 2017, pp. 1-19, MDPI.

Ricci et al., Home Monitoring Remote Control of Pacemaker and Implantable Cardioverter Defibrillator Patients in Clinical Practice: Impact on Medical Management and Health-Care Resource Utilization, Europace, Jan. 16, 2008, 7 pgs. European Society of Cardiology.

Sundaravadivel et al., Everything You Wanted to Know About Smart Health Care, IEEE Consumer Electronics Magazine, Dec. 13, 2017, pp. 18-28, IEEE Consumer Technology Society.

Vegesna et al., Remote Patient Monitoring via Non-Invasive Digital Technologies: A Systematic Review, Telemedicine and e-Health, Jan. 2017, pp. 3-17, Mary Ann Liebert, Inc.

* cited by examiner

EFFECTUATING THE REMOTE CARE SESSION RESPONSIVE TO INPUT BY THE PATIENT AT A SUITABLE GRAPHICAL USER INTERFACE (GUI) CONTROL PROVIDED AS PART OF A GUI ASSOCIATED WITH THE PATIENT CONTROLLER DEVICE AND THE CLINICIAN HAS ACTIVATED A CORRESPONDING GUI CONTROL PROVIDED AS PART OF A VIRTUAL WAITING ROOM DISPLAYED ON A GUI ASSOCIATED WITH THE CLINICIAN CONTROLLER DEVICE ⎯ 832

PROVIDING REMOTE THERAPY PROGRAMMING INSTRUCTIONS TO THE PATIENT'S IMD VIA THE REMOTE THERAPY SESSION ONLY AFTER VERIFYING THAT REMOTE CARE THERAPY PROGRAMMING WITH THE PATIENT'S IMD IS COMPLIANT WITH REGULATORY REQUIREMENTS OF ONE OR MORE APPLICABLE LOCAL, REGIONAL, NATIONAL, SUPRANATIONAL GOVERNMENTAL BODIES, NON-GOVERNMENTAL AGENCIES, AND INTERNATIONAL HEALTH ORGANIZATIONS ⎯ 842

REMOTELY CONTROLLING A CAMERA COMPONENT ASSOCIATED WITH THE PATIENT CONTROLLER DEVICE BY ACTIVATING ONE OR MORE GUI CONTROLS OF THE CLINICIAN PROGRAMMER DEVICE TO PAN AND ZOOM ON DIFFERENT PARTS OF THE PATIENT IN ORDER TO OBTAIN HIGHER QUALITY IMAGES OF THE PATIENT ⎯ 852

PAUSING THE AV COMMUNICATION SESSION WHILE THE REMOTE THERAPY SESSION IS PAUSED AND RESUMING THE AV COMMUNICATION SESSION WHEN THE REMOTE THERAPY SESSION IS RESUMED — 1920

ACTIVATING A FIRST ONE OF A PLURALITY OF REMOTE THERAPY SESSION CONTROLS PROVIDED AT THE PATIENT CONTROLLER DEVICE OR AT THE CLINICIAN PROGRAMMER DEVICE TO CAUSE A FIRST TRIGGERING EVENT (E.G., A PAUSE CONTROL) — 1930

ACTIVATING A SECOND ONE OF THE PLURALITY OF REMOTE THERAPY SESSION CONTROLS PROVIDED AT THE PATIENT CONTROLLER DEVICE OR AT THE CLINICIAN PROGRAMMER DEVICE TO CAUSE A SECOND TRIGGERING EVENT (E.G., A RESUME CONTROL) — 1940

| DATA 2302 | | | | NETWORK/KPI PARAMETRIC DATA 2306 | THERAPY SETTINGS DATA 2308 |
|---|---|---|---|---|---|
| AUDIO 2304-1 | VIDEO 2304-2 | VOCALIZATION 2304-3 | ... | MOTOR RESPONSE CAPTURE 2304-N | | |
| LABEL-1 | LABEL-2 | LABEL-3 | ... | LABEL-K ... LABEL-N | {P-1, P-2, P-3, ... P-M} | {STIM SETTING PROFILE-X} |
| ... | ... | ... | ... | ... | ... | ... |
| LABEL-A | LABEL-B | LABEL-C | ... | LABEL-J ... LABEL-Q | {P-1, P-2, P-3, ... P-V} | {STIM SETTING PROFILE-Z} |

DATA LABELING SYSTEM AND METHOD OPERATIVE WITH PATIENT AND CLINICIAN CONTROLLER DEVICES DISPOSED IN A REMOTE CARE ARCHITECTURE

PRIORITY AND CROSS-REFERENCE TO RELATED APPLICATION(S)

This nonprovisional application claims priority based upon the following prior United States provisional patent application(s): (i) "SYSTEM, METHOD AND ARCHITECTURE FOR FACILITATING REMOTE PATIENT CARE," Application No. 62/865,155, filed Jun. 22, 2019, in the name(s) of Scott DeBates et al., each of which is hereby incorporated by reference in its entirety.

This application discloses subject matter that is related to the subject matter of the following United States patent application(s): (i) "SYSTEM, METHOD AND ARCHITECTURE FOR FACILITATING REMOTE PATIENT CARE," application Ser. No. 16/449,056, filed Jun. 21, 2019, in the name(s) of Germinal Ibarrola et al.; (ii) "UI DESIGN FOR PATIENT AND CLINICIAN CONTROLLER DEVICES OPERATIVE IN A REMOTE CARE ARCHITECTURE," application Ser. No. 16/896,694, filed Jun. 9, 2020, in the name(s) of Scott DeBates et al.; and (iii) "SYSTEM AND METHOD FOR MODULATING THERAPY IN A REMOTE CARE ARCHITECTURE," application Ser. No. 16/900,202, filed Jun. 12, 2020, in the name(s) of Scott DeBates et al.; each of which is hereby incorporated by reference in its entirety.

TECHNICAL FIELD

The present disclosure generally relates to remote patient care. More particularly, and not by way of any limitation, the present disclosure is directed to a data labeling system and method operative with patient and/or clinician controller devices disposed in a remote care architecture.

BACKGROUND

Implantable medical devices have changed how medical care is provided to patients having a variety of chronic illnesses and disorders. For example, implantable cardiac devices improve cardiac function in patients with heart disease by improving quality of life and reducing mortality rates. Respective types of implantable neurostimulators provide a reduction in pain for chronic pain patients and reduce motor difficulties in patients with Parkinson's disease and other movement disorders. A variety of other medical devices are proposed and are in development to treat other disorders in a wide range of patients.

Many implantable medical devices and other personal medical devices are programmed by a physician or other clinician to optimize the therapy provided by a respective device to an individual patient. Typically, the programming occurs using short-range communication links (e.g., inductive wireless telemetry) in an in-person or in-clinic setting. Since such communications typically require close immediate contact, there is only an extremely small likelihood of a third-party establishing a communication session with the patient's implanted device without the patient's knowledge.

Remote patient care is a healthcare delivery method that aims to use technology to provide patient health outside of a traditional clinical setting (e.g., in a doctor's office or a patient's home). It is widely expected that remote patient care may increase access to care and decrease healthcare delivery costs.

Whereas advances in longer range telemetry capabilities and remote care networks continue to grow apace, several lacunae remain, thereby requiring further innovation as will be set forth hereinbelow.

SUMMARY

Embodiments of the present patent disclosure are directed to a system, method and a network architecture for facilitating remote care therapy via secure communication channels between clinicians and patients having one or more implantable medical devices (IMDs), wherein an integrated remote care service session operative to effectuate a common application interface for both audio/video (AV) communications and IMD programming may be implemented. In one arrangement, the network architecture includes a cloud-based service node or entity configured to execute a remote care session management service operative with one or more patient controller devices, each executing a patient controller application, and one or more clinician controller devices, each executing a clinician controller application. In some example embodiments, the patient and clinician controller applications may each comprise executable code operative to effectuate, inter alia, a consolidated graphical user interface (GUI) at respective patient and clinician controller devices that may include suitable GUI controls for remote session control as well as various remote applications, e.g., including but not limited to telemedicine/telediagnostics, remote patient monitoring, remote care therapy (i.e., remote programming of patients' IMDs), and the like.

In one aspect, an embodiment of a method for facilitating remote care management involving a patient having an implantable medical device (IMD) is disclosed. Example embodiment may include, inter alia, establishing a remote care session between a controller device associated with the patient and a programmer/controller device associated with a clinician, wherein the clinician and the patient are remotely located with respect to each other and the remote care session includes an AV communication session channel controlled by one or more AV controls provided at the patient controller device and/or by one or more AV controls provided at the clinician programmer device. When the patient requires remote therapy, one or more programming instructions may be transmitted to the patient's IMD via a remote therapy session component of the remote care session with the patient controller device. Upon establishing the remote care session, input from the patient or the clinician may be received via a user interface control associated with a particular functionality or aspect of the remote care session, including AV communications, remote therapy programming, and related network context. Responsive to the user input, a dialog interface may be effectuated at one of the patient controller device and/or the clinician programmer. A user characterization label may be received via the dialog interface from the user, i.e., the clinician and/or the patient, wherein the user characterization label is indicative of a subjective assessment of the particular functionality or aspect of the remote care session. In some variations, one or more a records may be generated for associating the user characterization labels with therapy settings data and one or more network performance metrics and context data that may be captured relative to when the user characterization labels are input by the user, thereby creating user-labeled data pertaining to the remote care session. In some variations, the user-labeled data records may be used for facilitating efficient retrieval of the therapy settings data based on user characterization label information in response to a user request (e.g., by a clinician). In some variations, the user-labeled data records may be used in training a machine language (ML) engine to provide efficient predictive analytics with respect to current or future therapy settings. In still further variations, assessments relating to at least one of AV communication quality, patient motor response capture quality, patient vocalization capture quality, and network performance, context data, etc., may be marked or indexed by different types of user characterization labels, e.g., textual labels, voice labels, ranking labels, binary category labels, graphic icon labels, gesture-based labels, etc.

In another aspect, an embodiment of a remote care management system is disclosed, which comprises, inter alia, a first external device configured as a clinician programmer device associated with a clinician; a second external device configured as a patient controller device associated with a patient; and an IMD implanted in the patient, wherein the IMD supporting a therapy application may be configured to be programmable by at least one of the clinician operating the first external device and the patient operating the second external device. The first external device and the second external device may be configured to establish a remote care session therebetween, wherein the remote care session is configurable to selectively effectuate a remote therapy session or channel for IMD programming in addition to or association with an AV communication session or channel that may be used for facilitating a telehealth consultation between the clinician and the patient. In one arrangement, the remote therapy session for delivering one or more programming instructions to the patient's IMD from the clinician programmer device may be effectuated in response to an input by the patient at the patient controller device to indicate the selection of a remote therapy mode of operation. Further, at least one of the first external device and the second external device may be provided with a user interface control for receiving user input, the user interface control associated with a particular functionality or aspect of the remote care session, including AV communications, remote therapy programming, and related network context. Responsive thereto, a dialog interface is effectuated at either the first or second external devices, which may be used by the user, i.e., the clinician and/or the user, to input a user characterization label indicative of a subjective assessment of the particular functionality or aspect of the remote care session.

In some variations, a record generator may be configured to create one or more a records associating the user characterization labels with therapy settings data and one or more network performance metrics and context data that may be captured relative to when the user characterization labels are input by the user. In some variations, a database module is provided for facilitating the storage and efficient retrieval of the therapy settings data based on user characterization label information in response to a user request (e.g., by a clinician).

In some variations, an ML engine may be included that may be trained by using the user-labeled data records to provide efficient predictive analytics with respect to current or future therapy settings. In still further variations, a remote care management system may include an triggering module configured to pause the remote therapy session in response to determining that a particular user characterization label (e.g., a negative characterization label) has occurred a predetermined number of times with respect to a certain functionality over a configurable period of time, which may be cleared responsive to an input from the clinician and/or the patient.

In still further aspects, one or more embodiments of a non-transitory computer-readable medium or distributed media containing computer-executable program instructions or code portions stored thereon are disclosed for effectuating one or more embodiments herein when executed by a processor entity of a patient controller device, a clinician controller device, a network node, apparatus, system, network element, a datacenter node or cloud platform, and the like, *mutatis mutandis*.

Additional/alternative features and variations of the embodiments as well as the advantages thereof will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

FIGS. 8A-8E depicts flowcharts illustrative of a remote care scenario involving the example remote care service architecture of FIG. 1A wherein an integrated remote care session may be established between a patient and a clinician operating respective controller devices that support suitable graphical user interfaces (GUIs) for facilitating a therapy session and an audiovisual (AV) communication session according to an example embodiment;

FIGS. 19A-19D depict flowcharts illustrative of blocks, steps and/or acts that may be (re)combined in one or more arrangements with or without additional flowcharts of the present disclosure for facilitating remote care therapy intervention according to some example embodiments;

FIG. 23 depicts an example database structure containing user-labeled data records in a remote care therapy service according to some embodiments;

DETAILED DESCRIPTION

Figure 1A:
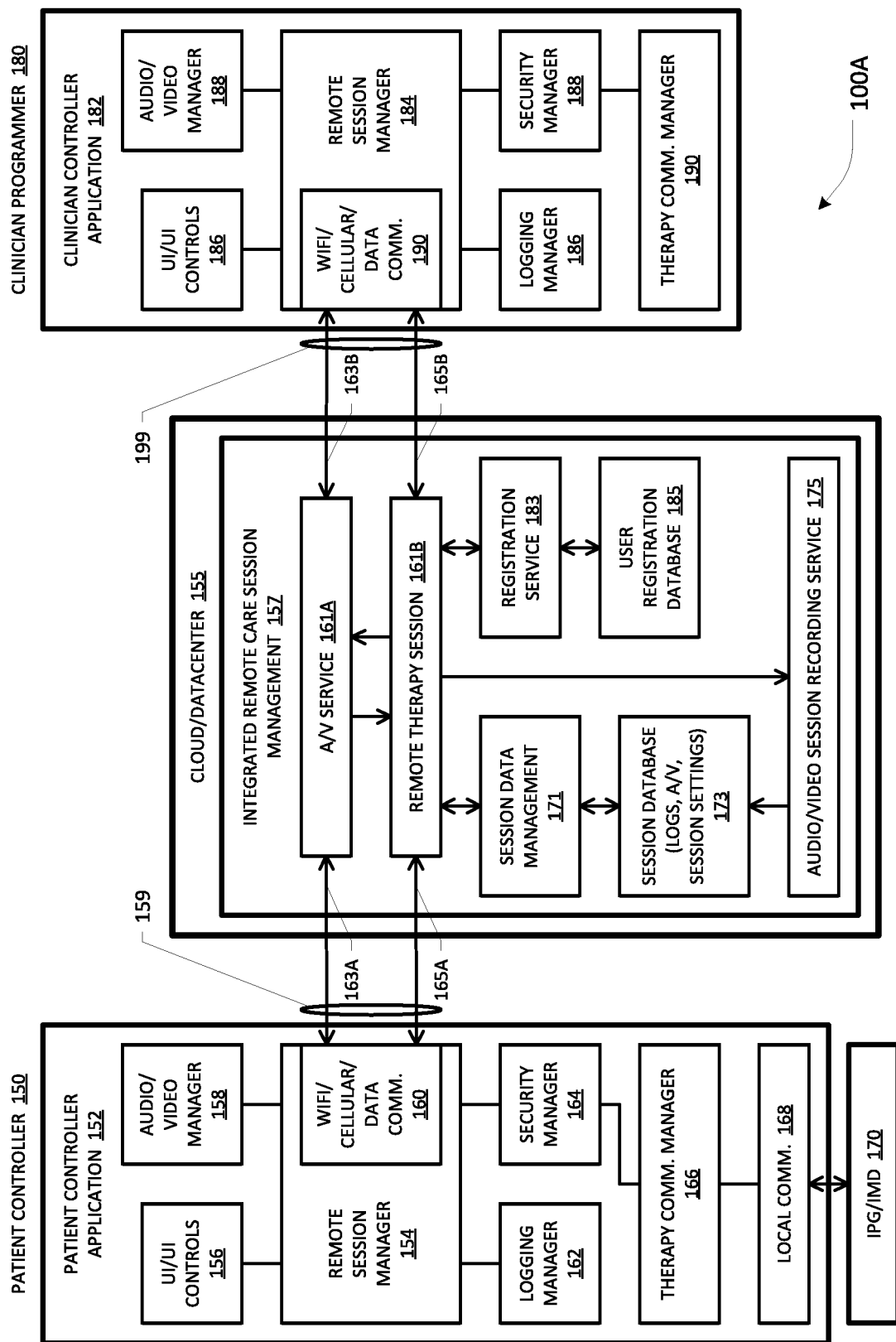
FIG. 1A depicts an example architecture of a system configured to support remote patient therapy as part of an integrated remote care service session according to one or more embodiments of the present patent disclosure.

In the description herein for embodiments of the present disclosure, numerous specific details are provided, such as examples of circuits, devices, components and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like set forth in reference to other embodiments herein. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some example embodiments described herein may relate to remote services including telehealth applications as well as remote care therapy applications particularly set forth with respect to an implantable pulse generator (IPG) or neuromodulator for providing therapy to a desired area of a body or tissue based on a suitable stimulation therapy application, such as a spinal cord stimulation (SCS) system or other neuromodulation systems. However, it should be understood that example embodiments disclosed herein are not limited thereto, but have broad applicability, including but not limited to remote care therapy applications involving different types of implantable devices such as neuromuscular stimulators and sensors, dorsal root ganglion (DRG) stimulators, deep brain stimulators, cochlear stimulators, retinal implanters, muscle stimulators, tissue stimulators, cardiac stimulators or pacemakers, gastric stimulators, and the like, as well as implantable drug delivery/infusion systems, implantable devices configured to effectuate real-time measurement/monitoring of one or more physiological functions of a patient's body (i.e., patient physiometry), including various implantable biomedical sensors and sensing systems. Further, whereas some example embodiments of remote care therapy applications may involve implantable devices, additional and/or alternative embodiments may involve external personal devices, e.g., wearable biomedical devices, that may be configured to provide therapy to the patients analogous to the implantable devices. Accordingly, all such devices may be broadly referred to as "personal medical devices," "personal biomedical instrumentation," or terms of similar import, at least for purposes of some example embodiments of the present disclosure.

Referring to FIG. 1A, depicted therein is an example architecture of a remote care service system 100A configured to support remote patient therapy as part of an integrated remote care service session according to one or more embodiments of the present patent disclosure. As used herein, a "remote care system" may describe a healthcare delivery system configured to support a remote care service over a network in a communication session between a patient and a clinician wherein telehealth or telemedicine applications involving remote medical consultations as well as therapy applications involving remote programming of the patient's IMD may be launched via a unified application interface facilitated by a network entity. In general, remote care therapy may involve any care, programming, or therapy instructions that may be provided by a doctor, a medical professional or a healthcare provider, and/or their respective authorized agents (including digital/virtual assistants), collectively referred to as a "clinician", using a suitable clinician device, with respect to the patient's IMD, wherein such therapy instructions are mediated, proxied or otherwise relayed by way of a controller device associated with the patient. As illustrated, the architecture of remote care system 100A includes a patient controller device 150 and a clinician controller device 180 (also referred to as a clinician programmer or clinician device), each having a corresponding remote care service application module, e.g., a patient controller application 152 and a clinician controller application 182, executed on a suitable hardware/software platform for supporting a remote care service that may be managed by a network entity 155. In some embodiments, the network entity 155 may comprise a datacenter or cloud-based service node (e.g., disposed in a public cloud, a private cloud, or a hybrid cloud, involving at least a portion of the Internet) operative to host a remote care session management service 157. In one arrangement, patient controller application 152 and clinician controller application 182 may each include a respective remote session manager 154, 184 configured to effectuate or otherwise support a corresponding communication interface 160, 190 with network entity 155 using any known or heretofore unknown communication protocols and/or technologies. In one arrangement, interfaces 160, 190 are each operative to support an AV channel or session 163A, 163B and a remote therapy channel or session 165A, 165B, respectively, with an AV communication service 161A and a remote therapy session service 161B of the remote care session management service 157 as part of a common bi-directional remote care session 159, 199 established therewith. In one arrangement, patient controller application 152 and clinician controller application 182 may each further include or otherwise support suitable graphical user interfaces (GUIs) and associated controls 156, 186, as well as corresponding AV managers 158, 188, each of which may be interfaced with respective remote session managers 154, 184 for purposes of one or more embodiments of the present disclosure as will be set forth in additional detail further below. Remote care session manager 154 of the patient controller application 152 and remote care session manager 184 of the clinician controller application may each also be interfaced with a corresponding logging manager 162, 186 for purposes of still further embodiments of the present disclosure. In one arrangement, remote care session manager 154 of patient controller application 152 is further interfaced with a security manager 164, which may be configured to facilitate secure or trusted communication relationships with the network entity 155. Likewise, remote care session manager 184 of clinician controller application 182 may also be interfaced with a security manager 188 that may be configured to facilitate secure or trusted communication relationships with the network entity 155. Each security manager 164, 188 may be interfaced with a corresponding therapy communication manager 166, 190 with respect to facilitating secure therapy communications between the clinician controller device 180 and the patient controller device 150. Therapy communication manager 166 of the patient controller application 152 may also interface with a local communication module 168 operative to effectuate secure communications with the patient's IPG/IMD 170 using a suitable short-range communications technology or protocol. In still further arrangements, security managers 164, 188 of patient and clinician controller applications 152, 182 may be configured to interface with the remote care session management service 157 to establish trusted relationships between patient controller device 150, clinician controller device 180 and IPG/IMD 170 based on the exchange of a variety of parameters, e.g., trusted indicia, cryptographic keys and credentials, inter alia.

In one arrangement, the integrated remote care session management service 157 may include a session data management module 171, an AV session recording service module 175 and a registration service module 183, as well as suitable database modules 173, 185 for storing session data and user registration data, respectively. As will be set forth in detail further below, at least part of the session data may include user-characterized data relating to AV data, therapy settings data, network contextual data, and the like, for purposes of still further embodiments of the present patent disclosure.

Skilled artisans will realize that the example remote care system architecture 100A set forth above may be advantageously configured to provide both telehealth medical consultations as well as therapy instructions over a communications network while the patient and the clinician/provider are not in close proximity of each other (e.g., not engaged in an in-person office visit or consultation). Accordingly, in some embodiments, a remote care service of the present disclosure may form an integrated healthcare delivery service effectuated via a common application user interface that not only allows healthcare professionals to use electronic communications to evaluate and diagnose patients remotely but also facilitates remote programming of the patient's IPG/IMD for providing appropriate therapy, thereby enhancing efficiency as well as scalability of a delivery model.

Additionally, the example remote care system architecture 100A may be implemented over various types of communication networks, e.g., homogenous networks, heterogeneous networks, hybrid networks, etc., which may be configured to provide patients with relatively quick and convenient access to diversified medical expertise that may be geographically distributed over large areas or regions, preferably via secure communications channels in some example embodiments as will be set forth in detail further below.

Figure 1B:
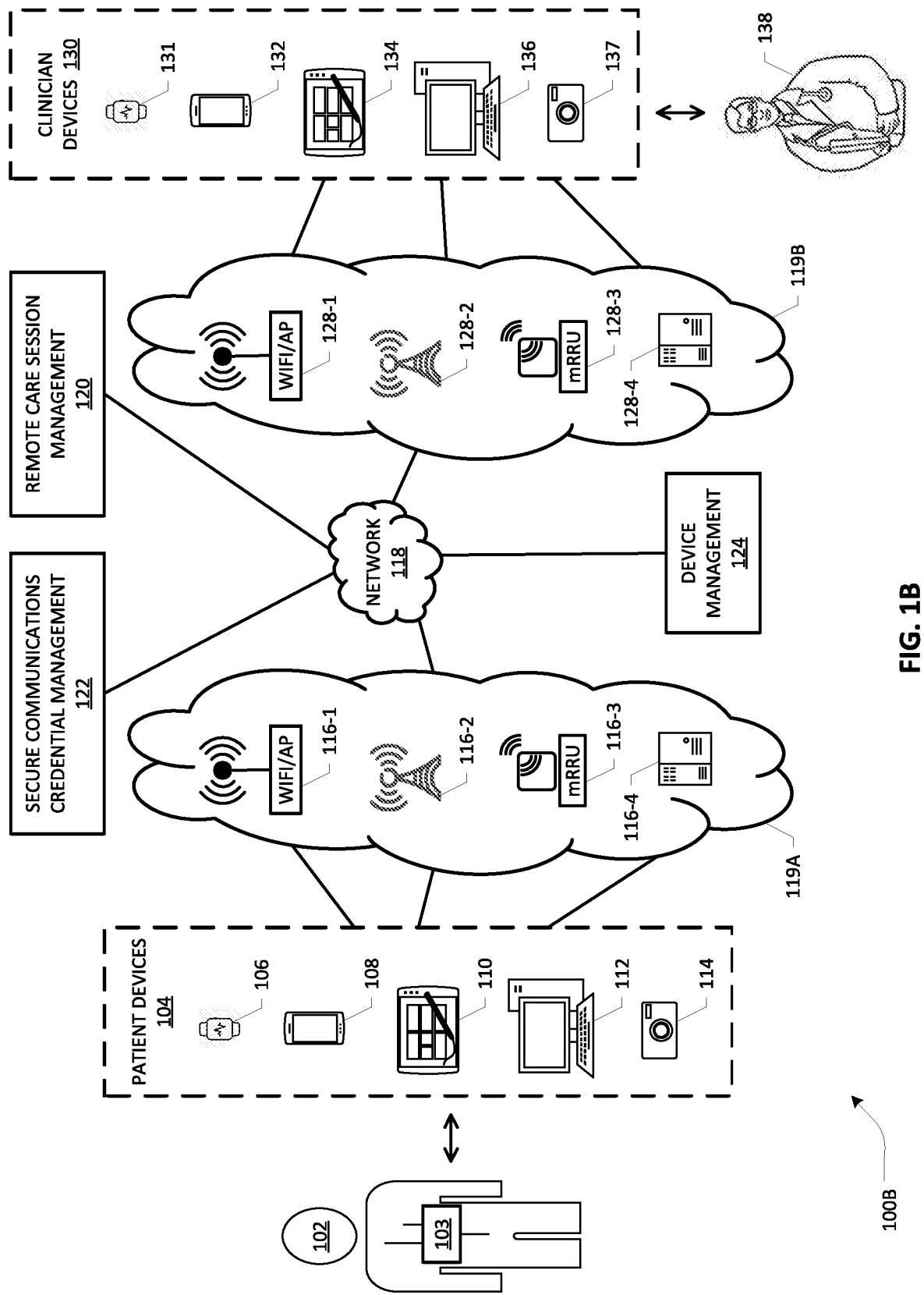
FIG. 1B depicts an example network environment wherein the remote care service architecture of FIG. 1A may be implemented according to a representative embodiment.

FIG. 1B depicts an example network environment 100B wherein the remote care service architecture of FIG. 1A may be implemented according to some embodiments. Illustratively, the example network environment 100A may comprise any combination or sub-combination of a public packet-switched network infrastructure (e.g., the Internet or worldwide web, also sometimes referred to as the "cloud", as noted above), private packet-switched network infrastructures such as Intranets and enterprise networks, health service provider network infrastructures, and the like, any of which may span or involve a variety of access networks, backhaul and core networks in an end-to-end network architecture arrangement between one or more patients, e.g., patient(s) 102, and one or more authorized clinicians, healthcare professionals, or agents thereof, e.g., generally represented as caregiver(s) or clinician(s) 138. Example patient(s) 102, each having one or more suitable implantable devices, e.g., IMD 103, may be provided with a variety of corresponding external devices for controlling, programming, otherwise (re)configuring the functionality of respective implantable device(s) 103, as is known in the art. Such external devices associated with patient(s) 102, referred to herein as patient devices 104, which are representative of patient controller device 150 shown in FIG. 1A, may comprise a variety of user equipment (UE) devices, tethered or untethered, that may be configured to engage in remote care sessions involving telehealth and/or therapy sessions according to some embodiments described below. By way of example, patient devices 104 may comprise smartphones, tablets or phablets, laptops/desktops, handheld/palmtop computers, wearable devices such as smart glasses and smart watches, personal digital assistant (PDA) devices, smart digital assistant devices, etc., any of which may operate in association with one or more virtual assistants, smart home/office appliances, smart TVs, external/auxiliary AV equipment, virtual reality (VR), mixed reality (MR) or augmented reality (AR) devices, and the like, which are generally exemplified by wearable device(s) 106, smartphone(s) 108, tablet(s)/phablet(s) 110, computer(s) 112, and AV equipment 114. As such, example patient devices 104 may include various types of communications circuitry or interfaces to effectuate wired or wireless communications, short-range and long-range radio frequency (RF) communications, magnetic field communications, etc., using any combination of technologies, protocols, and the like, with external networked elements and/or respective implantable devices 103 corresponding to patient(s) 102. Wth respect to networked communications, patient devices 104 may be configured, independently or in association with one or more digital/virtual assistants, smart home/premises appliances and/or home networks, to effectuate mobile communications using technologies such as Global System for Mobile Communications (GSM) radio access network (GRAN) technology, Enhanced Data Rates for Global System for Mobile Communications (GSM) Evolution (EDGE) network (GERAN) technology, 4G Long Term Evolution (LTE) technology, Fixed Wireless technology, $5^{th}$ Generation Partnership Project (5GPP or 5G) technology, Integrated Digital Enhanced Network (IDEN) technology, WMAX technology, various flavors of Code Division Multiple Access (CDMA) technology, heterogeneous access network technology, Universal Mobile Telecommunications System (UMTS) technology, Universal Terrestrial Radio Access Network (UTRAN) technology, All-IP Next Generation Network (NGN) technology, as well as technologies based on various flavors of IEEE 802.11 protocols (e.g., WiFi), and other access point (AP)-based technologies and microcell-based technologies such as femtocells, picocells, etc. Further, some embodiments of patient devices 104 may also include interface circuitry for effectuating network connectivity via satellite communications. Where tethered UE devices are provided as patient devices 104, networked communications may also involve broadband edge network infrastructures based on various flavors of Digital Subscriber Line (DSL) architectures and/or Data Over Cable Service Interface Specification (DOCSIS)-compliant Cable Modem Termination System (CMTS) network architectures (e.g., involving hybrid fiber-coaxial (HFC) physical connectivity). Accordingly, by way of illustration, an edge/access network portion 119A is exemplified with elements such as WiFi/AP node(s) 116-1, macro/microcell node(s) 116-2 and 116-3 (e.g., including micro remote radio units or RRUs, base stations, eNB nodes, etc.) and DSL/CMTS node(s) 116-4.

In similar fashion, clinicians and/or clinician agents 138 may be provided with a variety of external devices for controlling, programming, otherwise (re)configuring or providing therapy operations with respect to one or more patients 102 mediated via respective implantable device(s) 103, in a local therapy session and/or telehealth/remote therapy session, depending on implementation and use case scenarios. External devices associated with clinicians/agents 138, referred to herein as clinician devices 130, which are representative of clinician controller device 180 shown in FIG. 1A, may comprise a variety of UE devices, tethered or untethered, similar to patient devices 104, which may be configured to engage in telehealth and/or remote care therapy sessions as will be set forth in detail further below. Clinician devices 130 may therefore also include devices (which may operate in association with one or more virtual assistants, smart home/office appliances, VR/AR/MR devices, and the like), generally exemplified by wearable device(s) 131, smartphone(s) 132, tablet(s)/phablet(s) 134, computer(s) 136 and external/auxiliary AV equipment 137. Further, example clinician devices 130 may also include various types of network communications circuitry or interfaces similar to that of personal devices 104, which may be configured to operate with a broad range of technologies as set forth above. Accordingly, an edge/access network portion 119B is exemplified as having elements such as WiFi/AP node(s) 128-1, macro/microcell node(s) 128-2 and 128-3 (e.g., including micro remote radio units or RRUs, base stations, eNB nodes, etc.) and DSL/CMTS node(s) 128-4. It should therefore be appreciated that edge/access network portions 119A, 119B may include all or any subset of wireless communication means, technologies and protocols for effectuating data communications with respect to an example embodiment of the present disclosure.

In one arrangement, a plurality of network elements or nodes may be provided for facilitating an integrated remote care therapy service involving one or more clinicians 138 and one or more patients 102, wherein such elements are hosted or otherwise operated by various stakeholders in a service deployment scenario depending on implementation (e.g., including one or more public clouds, private clouds, or any combination thereof). According to some example embodiments, a remote care session management node 120 may be provided, generally representative of the network entity 157 shown in FIG. 1A, preferably disposed as a cloud-based element coupled to network 118, that is operative in association with a secure communications credentials management node 122 and a device management node 124, to effectuate a trust-based communications overlay/tunneled infrastructure in the network environment 100 whereby a clinician may advantageously engage in a telehealth session and/or a remote care therapy session with a particular patient via a common application interface and associated AV and therapy controls, as will be described further below.

Figure 2A:
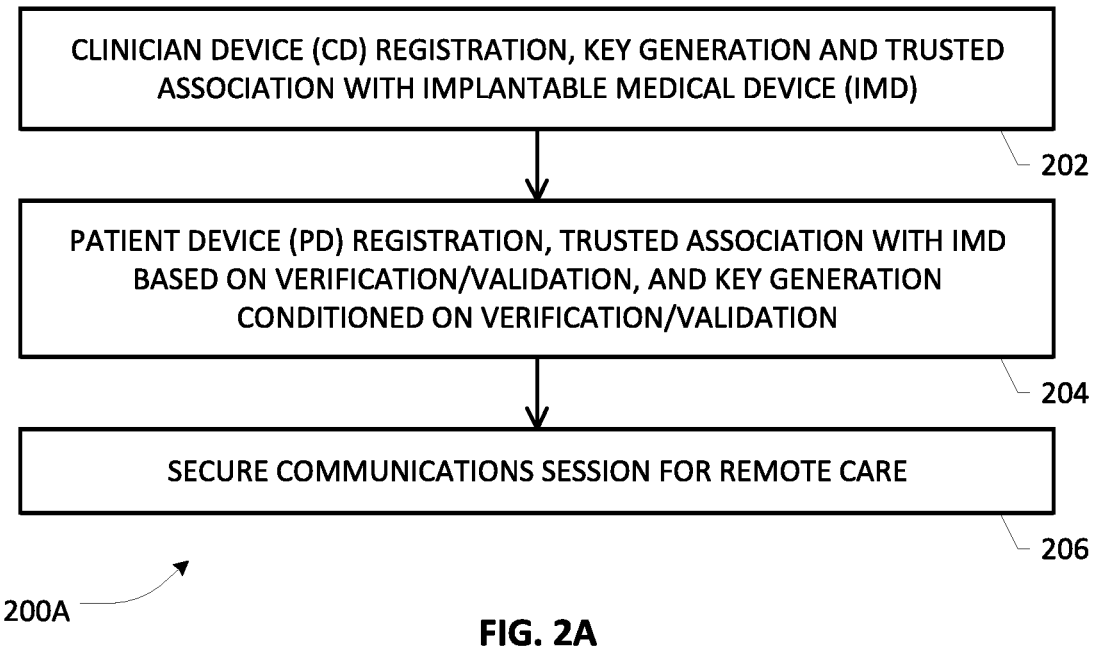
FIGS. 2A-2C depict flowcharts illustrative of blocks, steps and/or acts that may be (re)combined in one or more arrangements with or without additional flowcharts of the present disclosure for facilitating remote care therapy with respect to a patient having an implantable medical device (IMD) according to some embodiments.
Figure 2B:
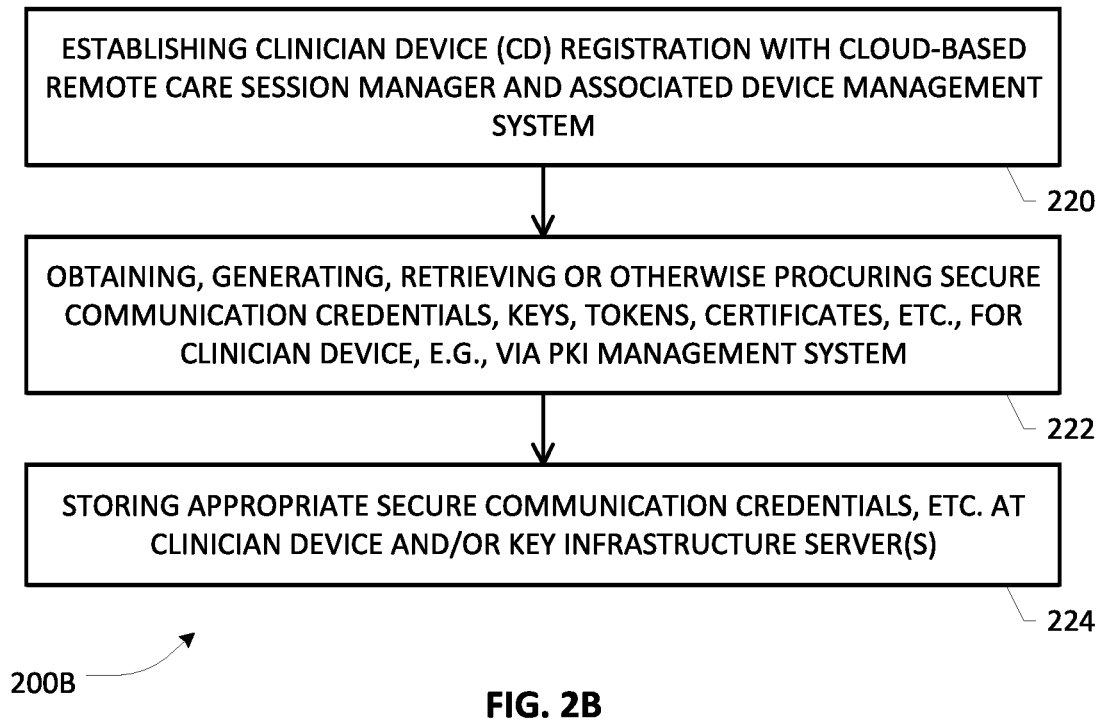
Figure 2C:
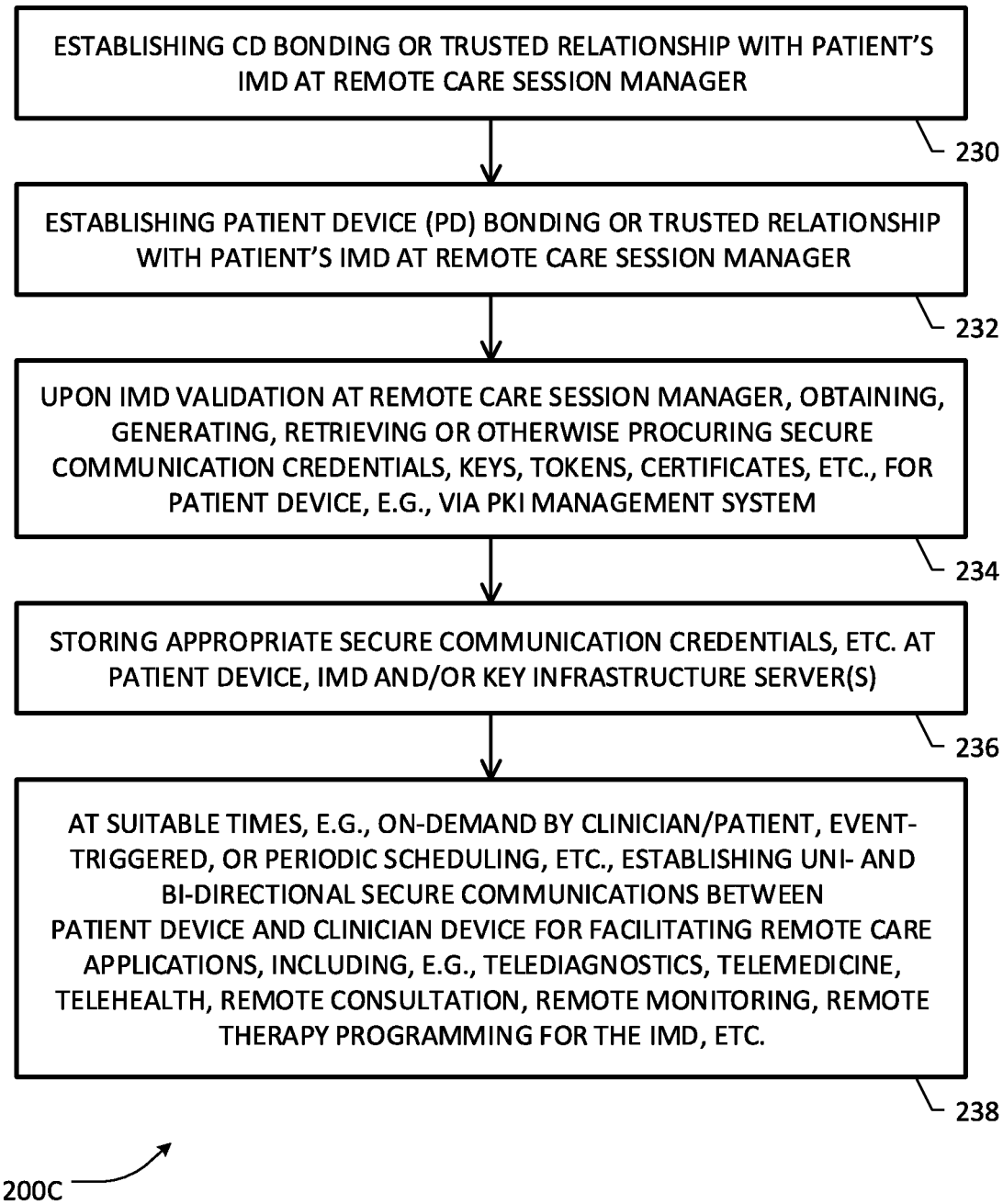

FIGS. 2A-2C depict flowcharts illustrative of blocks, steps and/or acts that may be (re)combined in one or more arrangements with or without additional flowcharts of the present disclosure for facilitating remote care therapy with respect to a patient having an IMD in some embodiments. Although some implementations herein describe remote care therapy delivery based on establishing trust associations involving a patient controller device, patient's IMD and a clinician programmer, it should be appreciated that embodiments of the present patent disclosure are not limited thereto. Some embodiments herein may therefore utilize certain unique information from a patient's IMD in association with a suitable key structure system (e.g., a public key infrastructure (PKI) system) operating as a secure credential management system with respect to a clinician device and a patent device for registration and generation of trust associations, preferably prior to engaging in a remote care and therapy/programming session therebetween. Example process 200A of FIG. 2A is representative of a scheme that may be practiced in effectuating a remote care therapy system via a network environment (e.g., network environment 100B shown in FIG. 1B) according to an example embodiment. At block 202, various operations relating to clinician device registration, encryption key generation and establishment of a trusted association between the clinician device and a patient's IMD are effectuated. At block 204, various operations relating to patient device registration and establishment of trusted association with the IMD based on verification/validation may be performed, which may be followed by encryption key generation conditioned on verification/validation operations. It will be appreciated that at least a portion of the operations set forth at blocks 202 and 204 may be performed in some embodiments while the clinician and the patient are in proximity of each other (e.g., at the clinician's office, the patient's home, etc., where there is little chance of unauthorized tampering with device communications between the clinician device and the IMD as well as between the patient device and the IMD). After the operations of blocks 202 and 204 are successfully completed, the patient and the clinician may go their separate ways (e.g., the patient may leave the clinician's office or return home, the clinician may leave the office or the patient's premises, etc.), whereby the clinician may be remotely located with respect to the patient. By virtue of the trusted associations established among the devices through the IMD, a secure communication session may be established at a later time, e.g., by the clinician operating the authorized clinician device and/or the patient operating the patient device, for providing/consuming remote care (block 206).

Example process 200B of FIG. 2B is representative of additional details with respect to some of the operations set forth above according to some embodiments. At block 220, a clinician device registers with a cloud-based remote care session manager node and/or associated device management system, such as, e.g., nodes 120, 124 and 155 set forth in FIGS. 1A/1B described above. Thereafter, one or more secure communication credentials, keys, tokens, certificates, etc., for the clinician device, may be obtained, generated, retrieved, generated or otherwise procured (block 222), e.g., using a PKI management system in some embodiments. At block 224, the secure communication credentials may be stored at the clinician device. Where public-key cryptographic keys are involved, such keys may also stored/managed via suitable certification/registration authorities.

Example process 200C of FIG. 2C is representative of additional details with respect to some of the operations set forth above in reference to FIG. 2A according to some embodiments. At block 230, a device bonding or trusted relationship between the clinician device and the patient's IMD may be established at the remote care session manager based on certain unique information obtained/retrieved from the IMD. At block 232, a device bonding or trusted relationship between the patient's device and the patient's IMD may be established at the remote care session manager. Upon performing suitable IMD validation operations at the remote care session manager for the patient device, one or more secure communication credentials, keys, tokens, certificates, etc., may be obtained, generated, retrieved, generated or otherwise procured, for the patient device (block 234). Similar to the key generation process for the clinician device set forth in FIG. 2B, the keys for the patient device may be obtained in association with a PKI management system in some example embodiments and such keys may be stored/managed at the patient device, key certification/registration authorities, or both. In some example embodiments, at least one or more private keys may also be stored in the patient's IMD, as set forth at block 236. Thereafter, uni- and/or bi-directional secure communications may be established remotely between the patient device and the clinician device (e.g., secure A/V communication channel for facilitating video conferences in addition to a secure remote therapy session for programming the IMD), wherein one or more remote care applications, e.g., diagnostics, telehealth/telemedicine consultation, remote monitoring, remote therapy programming for IMDs, and the like, may be effectuated. Skilled artisans will recognize that such secure communications may be launched by the clinician and/or the patient, e.g., as needed, on-demand, or effectuated responsive to (pre)configured mechanisms (e.g., triggered by reaching certain thresholds in a stimulation therapy), or based on periodic scheduling, and the like, generally set forth at block 238. Further, once a remote care therapy session is established between the patient and the clinician, it may be further modulated or intervened using suitable AV/therapy controls provided as part of GUIs at either patient and/or clinician controller devices according to some embodiments as will be set forth below.

Figure 3:
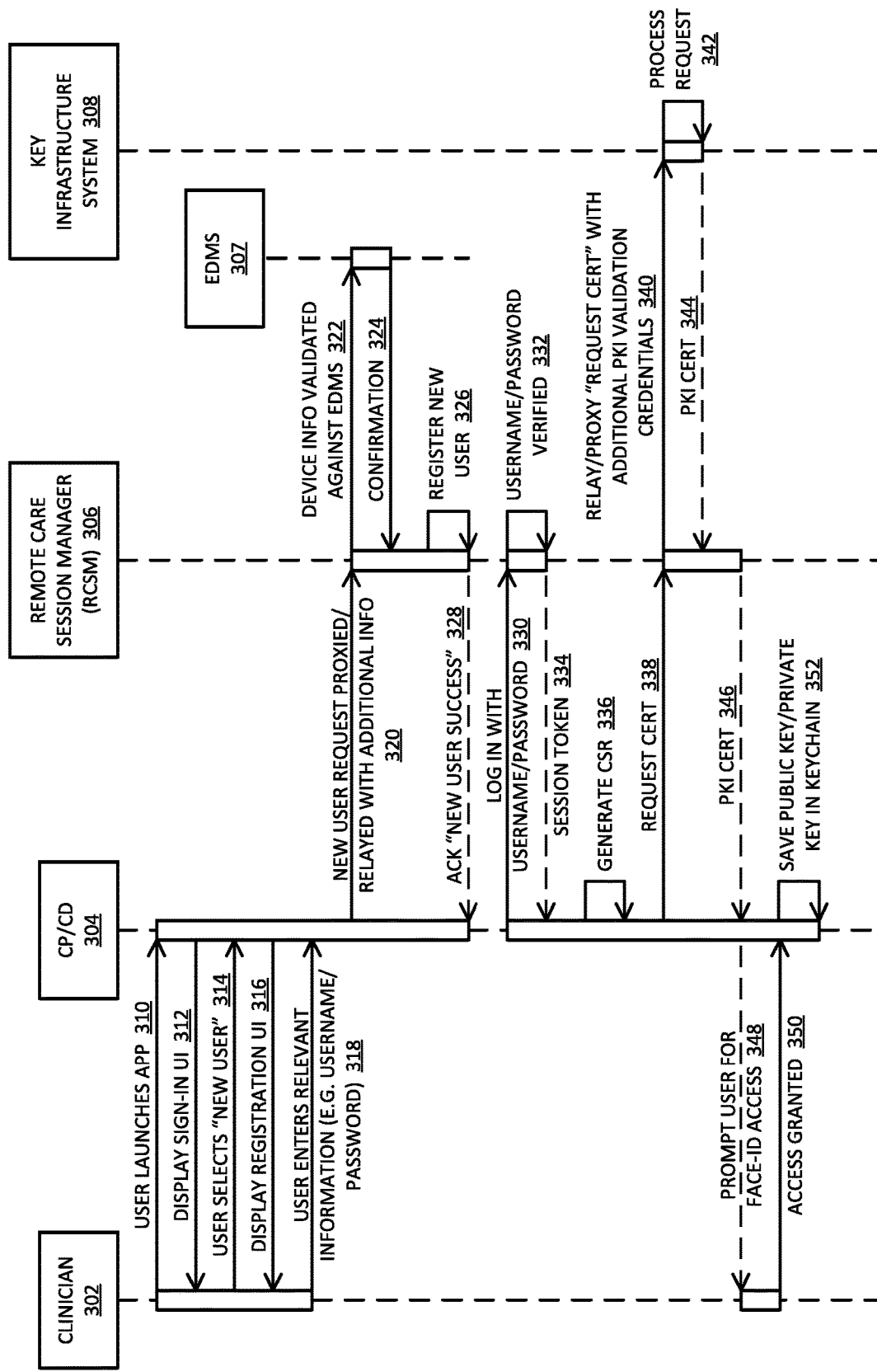
FIGS. 3-5 depict flow diagrams illustrative of example message/work flows for effectuating trusted associations among a clinician device, patient device and the patent's IMD via a remote care session manager for purposes of some embodiments.
Figure 4:
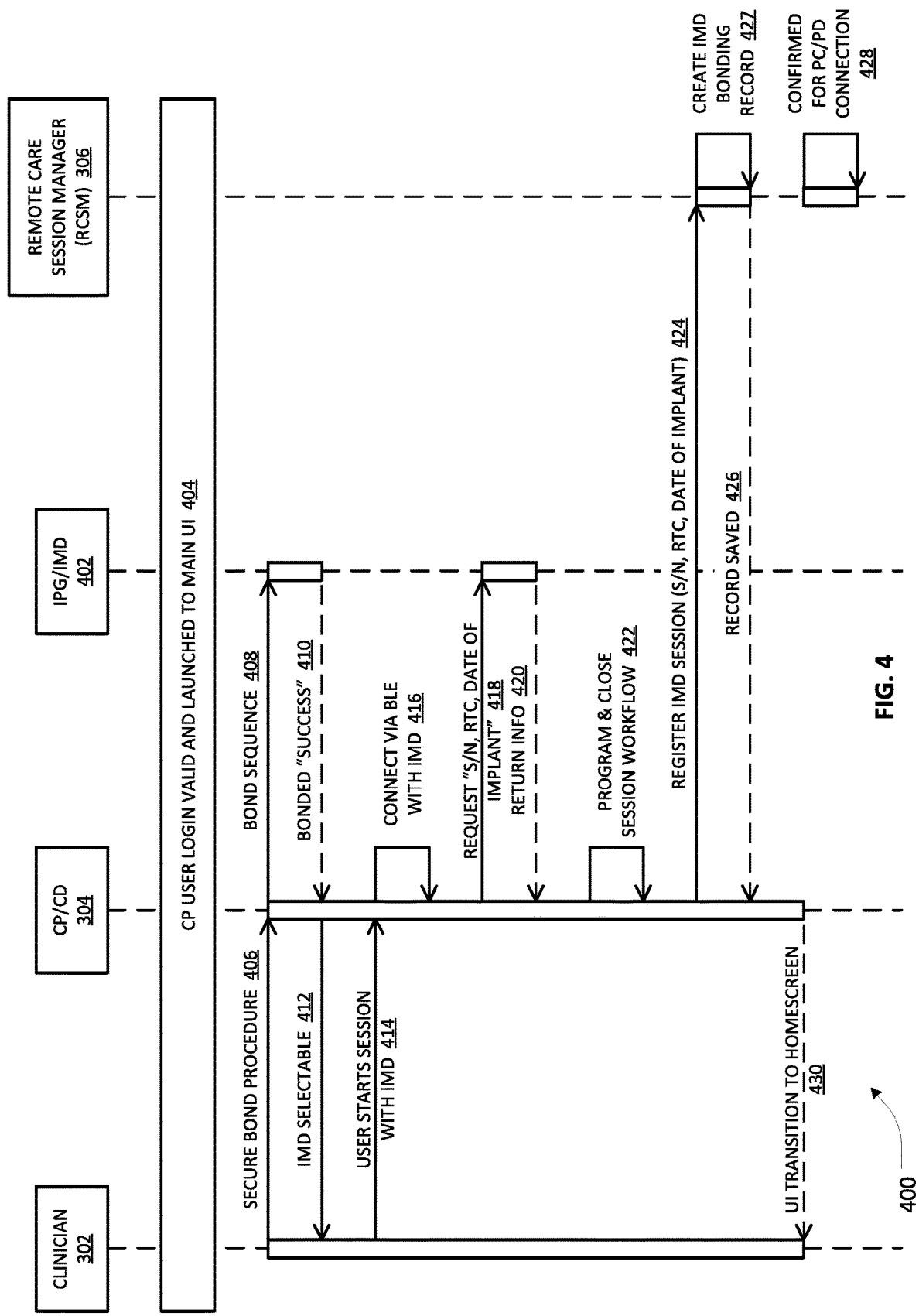
Figure 5:
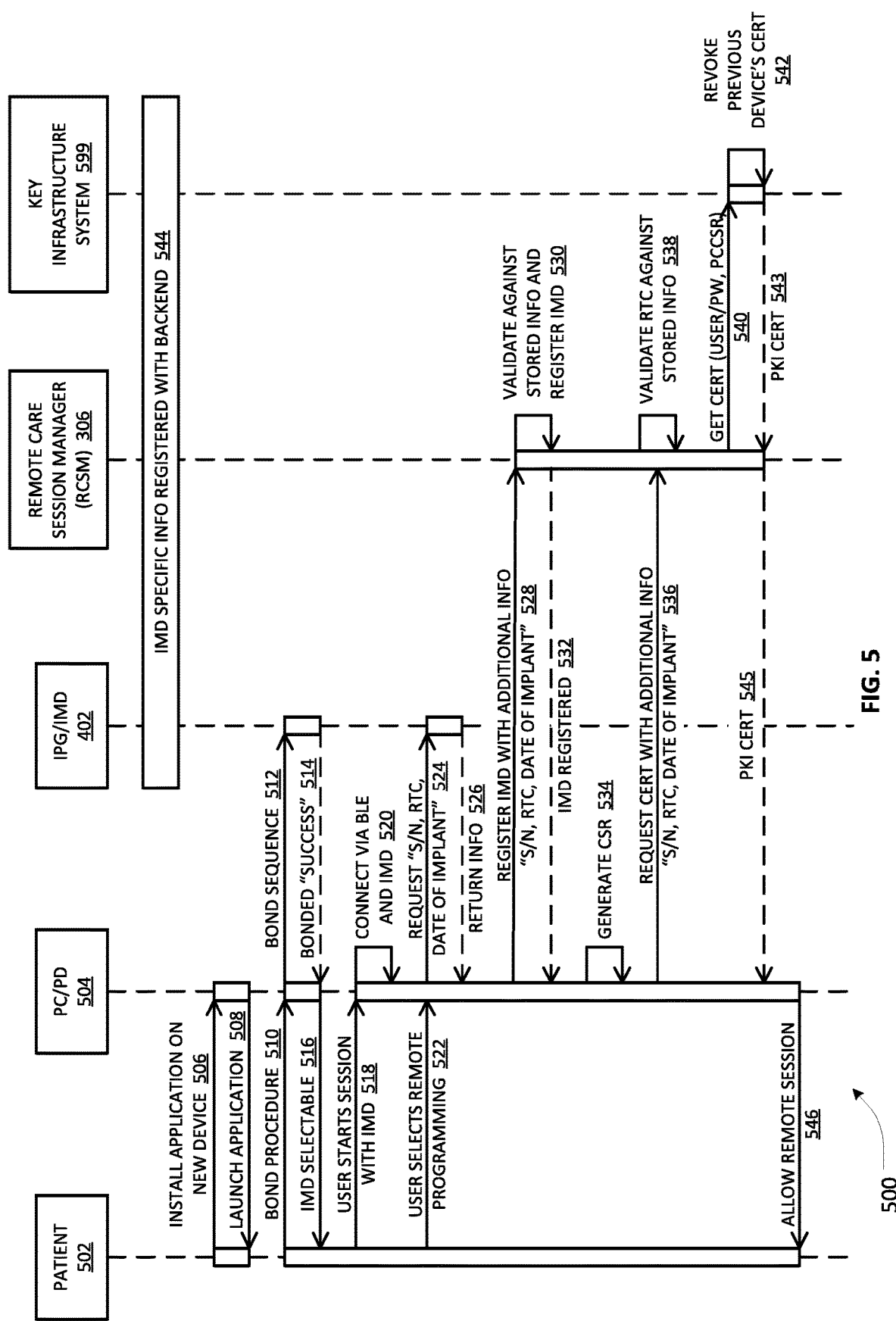

FIGS. 3-5 depict message flow diagrams illustrative of one or more message and/or work flows that exemplify additional details with respect to registering clinician and patient devices and effectuating trusted associations based on the patent's IMD via a remote care session manager for purposes of some embodiments of the present patent disclosure. Message/work flow 300 shown in FIG. 3 is representative of operations that may be undertaken by a clinician 302 who may be a new or current healthcare provider of one or more patients (not explicitly shown in this FIG.), where the clinician 302 may be allowed or otherwise engaged by a suitable healthcare entity, facility, organization or authority to provide remote care therapy with respect to such patient(s) under applicable service arrangements and/or regulations. Accordingly, at least a portion of the operations involving clinician 302 in this message flow diagram may comprise operations relative to initial enrollment/registration of clinician 302 and associated clinician programmer/device (CP/CD) 304. It will be realized that CP/CD 304 may comprise any type of computing/communications device (e.g., selected from and/or a combination of clinician devices 130 depicted in FIG. 1B), which may be configured to execute a special piece of software, code or program(s) (generally referred to as an "application" or "app"), which may be representative of and/or operative as clinician controller application 182 set forth in FIG. 1A in some example embodiments, to allow the clinician 302 to perform various preconfigured and/or (re)configurable healthcare-specific tasks via a suitable UI that may include graphics, video, audio, and/or text or command line interfacing. In general, such apps may be referred to as desktop applications or mobile apps depending on whether a desktop/laptop device or a handheld mobile device (e.g., a smartphone, a tablet/phablet, or a custom-built clinician programmer device) is configured to operate as CP/CD 304. Regardless of how CD/CP 304 is implemented, one or more suitable apps (e.g., an app suite) may be downloaded, installed, pre-configured, or otherwise provided with CP/CD 304 (e.g., either beforehand or at initial enrollment in some embodiments) for executing as part of an application software platform in association with the device Operating System (OS) environment, which execution may be effectuated when the application is launched by the clinician 302 or clinician's authorized agent, e.g., via appropriate voice/graphics/text input, as exemplified at work flow 310 in FIG. 3. Responsive thereto, a UI display may be presented to the clinician/agent 302 for facilitating input of appropriate user registration credentials (e.g., usernames, passwords, multi-factor authentication tokens etc.), by way of selecting a "New User" icon, software button or pull-down menu window in the UI display, as exemplified by work flow messages 312, 314, 316, 318 in FIG. 3. Upon entry of relevant user information with respect to the clinician/agent 302, CP/CD 304 relays or proxies a new user registration request to a remote care session manager (RCSM) 306 via a suitable network connection, as exemplified by message flow 320, wherein RCSM 306 may be disposed in a network environment or architecture as described above in reference to FIGS. 1A and 1B. In some example embodiments, additional device information associated with CP/CD 304 and/or the remote care application may be included in the relayed/proxied request, such as, e.g., device identity, application version data, and/or any hard-coded device data, etc. RCSM 306 may be provided as part of a cloud-based service architecture, e.g., Software as a Service (SaaS), Platform as a Service (PaaS), Infrastructure as a Service (IaaS) etc., operated/hosted by one or more datacenter services, healthcare providers, medical services providers, medical equipment manufacturers, healthcare insurance network operators, and the like, as noted previously. In some embodiments, RCSM 306 may be configured to validate the received device information against an enterprise device management system (EDMS) 307 associated therewith, e.g., pursuant to a suitable service level agreement or SLA, in order to ensure that only appropriately managed clinician devices are allowed to engage in remote care service enrollment. In one embodiment, EDMS 307 may be implemented via a mobile device lifecycle management system supported by a third-party service provider operative to deploy, configure, manage, support and secure mobile clinician devices through mobile device management (MDM) profiles installed on the devices, such as, e.g., CP/CD 304. In some embodiments, MDM software may be configured to facilitate asset inventory, over-the-air (OTA) configuration of application(s), remote troubleshooting, and remote lock and wipe capabilities to secure the devices and the sensitive patient data on them. In one implementation, MDM software operative in association with RCSM 306 may be provided as an application operating on the managed clinician devices that may be configured as part of a device- and platform-agnostic service, which centralizes the management, configuration and security of one or more clinicians and associated devices approved for providing remote care. In some embodiments, the functionalities and capabilities of RCSM and EDMS may be integrated as a tenant service within a datacenter platform configured as, e.g., a server farm having advantageous features such as failover, redundancy, hot-pluggability and high availability, among others.

Irrespective of whether RCSM 306 and EDMS 307 are integrated (e.g., tightly coupled or loosely coupled), appropriate validation message flow 322 and confirmation message flow 324 may be exchanged therebetween to validate and confirm the new user (i.e., clinician 302 and/or CP/CD 304) in some embodiments of the present patent disclosure. Responsive thereto, RCSM 306 is operative to register the clinician 302 and associated device CP/CD as a valid, authenticated and/or authorized user/provider, as exemplified by message flow 326. Thereafter, a suitable response or acknowledgement message may be generated by the remote care session manager 306 to CP/CD 304, as exemplified by message flow 328. Subsequently, a log-in operation may be effectuated in association with CP/CD 306 (e.g., substantially immediately after the registration acknowledgement message is received from RCSM 306 or after a time period has passed, and/or after certain preconfigured events and notifications have taken place) to log in with RCSM 306 using appropriate user credentials (e.g., the username and password combination, etc.) for commencing a session with respect to obtaining and/or generating secure communication credentials. Upon verification by RCSM 306, a session token may be provided to CP/CD 304. By way of illustration, these operations are exemplified by message flows 330, 332 and 334 in the message flow diagram 300 of FIG. 3. Responsive thereto, CP/CD 304 may be configured to generate or launch a certificate signing request (CSR) process, exemplified by message flow 336, with respect to one or more cryptographic keys, wherein a request for a digital certificate may be transmitted to RCSM 306, which may be propagated, relayed or otherwise proxied to a suitable key infrastructure system 308, as exemplified by message flows 338 and 340. In some embodiments, where an asymmetric cryptography system is implemented for securing communications (e.g., a key pair comprising a separate public key and a private key is used), the key infrastructure system 308 may comprise a PKI system, as noted previously. In a further embodiment, the proxied request 340 relayed to the key infrastructure system 308 may include additional PKI validation credentials depending on the configuration of RCSM 306 and/or profile management of clinician 302 and associated CP/CD 304. Responsive to processing the certificate request 340, the key infrastructure system 308 is operative to generate a digital certificate, which is propagated to CP/CD 304 via RCSM 306, as exemplified by message flows 342, 344 and 346. In some example embodiments, a further level of user authentication for access control may be required before the secure communication credentials (e.g., public/private keys, tokens, etc.) are stored in CP/CD 304.

For example, facial recognition and/or other forms of biometric identification may be required of the clinician 302 prior to access is granted and the keys are securely stored at CP/CD 304, as exemplified by flows 348, 350 and 352.

Wth respect to managing and maintaining the secrecy of private keys and facilitating assurance of public keys, some example embodiments may therefore involve providing suitable hardware, software and/or firmware as part of CP/CD 304 functionality, wherein a key pair combination may be generated and/or otherwise obtained, e.g., either in association with a certificate or certification authority (CA), or otherwise, such that the private key is stored at an private key store and the public key is provided in a CSR process identifying the requesting subject (e.g., clinician 302, CP/CD 304, or in combination) that may be processed by the CA and/or in association with a third-party registration authority (RA). Further, skilled artisans will recognize that several levels of certificates may be provided depending on the level of security or trust is required in a remote care therapy service, which in turn may necessitate providing different levels of identity credentials as part the CSR. Upon duly processing the CSR and verifying the identity of the requester (e.g., clinician 302, and/or CP/CD 304), a digital certificate may be issued to the requester, which may include requester identity credentials, expiration date, usage levels, certificate issuer information, etc.

While the public key of a subject entity may be stored on the digital certificate, the associated secret private key can be stored on the key owner's device (e.g., CP/CD 304) in some embodiments. However, such an arrangement may not be optimal because if a malicious party gains access to the device, s/he can unlawfully access the private key, thereby breaching or otherwise compromising the level of security and/or privacy required for remote care therapy services. In some embodiments, therefore, the private key may be stored on a secure removable storage or token that can only be accessed via further validation (e.g., a challenge-response mechanism). For example, CP/CD 304 may be provided with a suitable interface to facilitate a security token operative with a variety of interfacing technologies, e.g., Universal Serial Bus (USB), near-field communication (NFC), radio frequency identification (RFID), or Bluetooth, as well as audio/visual signature interfacing. It will be appreciated that such security measures may help reduce the likelihood that a clinician's device is compromised before attempting to "bond" with a patient's IMD (i.e., establishing a trusted association or relationship between the clinician's device and a patient's IMD via RCSM 306). In some example embodiments, establishing such inter-device relationships may be facilitated in a secure or trusted environment to help enhance the overall security of a remote care therapy service scenario.

Turning now to FIG. 4, message/work flow 400 depicted therein is representative of operations that may be undertaken by the clinician 302 preferably in the presence of a patient (not explicitly shown) having an IMD 402 for securely bonding with and registering IMD 402 RCSM 306 in order to facilitate remote care therapy at some point in the future. As one skilled in the art will recognize, the message/work flow 400 of FIG. 4 and the message/work flow 300 of FIG. 3 may be engaged by the clinician 302 at different times, although it is preferred that the message/work flow 300 takes place prior to the message/work flow 400. Further, whereas the message/work flow 300 of FIG. 3 may typically take place without the presence of a patient (e.g., remotely, because the patient's IMD is not involved), such message/work flow may also be engaged while in the presence or vicinity of the patient (e.g., locally, when engaging with the patient's IMD to perform at least a portion of the operations of the message/work flow 400). Illustratively, the message/work flow 400 may be engaged in one embodiment during an in-person or in-clinic visit (e.g., an initial patient visit with a new clinician or with an existing clinician when the patient has acquired a new/replacement IMD, etc.) while the patient having the IMD 402 is in the clinician's office or offsite at a medical care facility or even at the patient's home or some type of care facility or affiliate (e.g., a nursing home or eldercare facility). Generally, in one arrangement, the clinician 302 operating CP/CD 304 may already be validly logged in and engaged in suitable network connectivity with RCSM 308, as exemplified by log-in session 404. A secure "bonding" procedure 406 may be initiated by the clinician 402 via CP/CD 304, e.g., using suitable software menu options, pull-down menus, icons, or other mechanisms, etc., to cause a bonding sequence 408 to be launched between CP/CD 304 and the patient's IMD 402. In one arrangement, such secure bonding procedure may be facilitated by using a "triggering device" in the proximity or vicinity of IMD 402, as will be set forth in additional detail hereinbelow. Responsive to receiving a message or indication that the bonding sequence is successful, as exemplified by message flow 410, an indication 412 (e.g., visual, textual, tactile or audio/video) may be provided to the clinician 302 that IMD 402 is selectable for initiating a secure local communication session therewith via CP/CD 304. In one embodiment, such a local communication session between may be effectuated using without limitation, inter alia, Bluetooth Low Energy (BLE), NFC, Zigbee, and the like, as exemplified by message flows 414, 416. After establishing the communication channel between CP/CD 304 and IMD 402, a request for information may be generated to IMD 402, which in some embodiments may comprise a request for the IMD's serial number, time/date of when the IMD 402 is implanted in the patient (e.g., a timestamp indicative of first implantation and/or subsequent (re)implantations if performed), a measurement or read-out of any device, circuit or module configured to keep an accurate record of the current time and/or lapsed time, e.g., high precision event timers (e.g., based on hardware, software and/or firmware events), real-time clocks (RTCs), timestamp counters (TSCs), power management timers, programmable interval timers (PITs), etc., as well as other unique data, information, or indicia stored in the IMD 402 (e.g., one or more device-based cryptographic keys, IMD's device identifiers, etc.). In addition, depending on implementation, one or more biometric authentication data and/or a digest thereof uniquely associated with the patient (e.g., digital fingerprints, iris/retinal scans, facial recognition, voice recognition, etc.) as well as certain programmatically generated data (e.g., based on hash algorithms, etc.) performed on stored patient data, program/version identifiers associated with stored stimulation/therapy programs, and the like, may also be requested and/or obtained as part of the requesting process 418. Any combination or sub-combination of the foregoing data, without limitation, as well as any other personalized authentication indicia associated with a patient (e.g., based on genetic/chromosomal markers such as specific sequences of deoxyribonucleic acid or DNA, immunological/physiological markers, digital challenge-response patterns such as brain scan waveforms responsive to an audio/visual challenge, and the like), currently known or heretofore unknown, may be referred to herein as "trust indicia," which may be returned to the requesting CP/CD 304 in a secure local communication session. As will be set forth further below, any portion of such trust indicia may be utilized in registering an IMD and creating a trusted associative relationship involving the unique combination of a clinician programmer/device and a patient controller/device, and mediated via the corresponding IMD in some example embodiments of the present patent disclosure.

Responsive to receiving the requested data from IMD 402, the clinician 302 may operate CP/CD 304 to program IMD 402 (e.g., input appropriate therapy settings, etc.) and, in one embodiment, may close the secure local communication session as exemplified as message/work flows 420, 422. Thereafter, the clinician 302 may launch an IMD registration session via CP/CD 304, e.g., using pull-down menus, icons, or other mechanisms, etc., available as part of the downloaded remote care therapy app, with RCSM 306 by means of a network connection (e.g., a broadband connection effectuated via WiFi, 5G, LTE, CDMA/TDMA, WiMAX, DSL/CMTS, etc.) therewith, wherein a registration message including at least a portion of the trust indicia data may be transmitted to RCSM 306 as exemplified by message flow 424. Responsive thereto, RCSM 306 is operative to create and store a bonding relationship record 427 thereat, which in some embodiments may include the trust indicia data forwarded by CP/CD 304 as well as suitable identity/indication data corresponding to the clinician 302 and/or CP/CD 304, e.g., to indicate that clinician 302 and/or CP/CD 304 are trusted entities operative to engage in one or more therapy operations involving the patient's IMD 402. A response message 426 may be generated back to CP/CD 426 from RCSM 306 indicating the generation and storage of the IMD bonding relationship record. In an example embodiment, the UI display of CP/CD 304 may transition to a home screen to allow the clinician 302 to undertake further operations and/or close and exit the IMD registration process (e.g., engaging in local therapy administration, (re)configuration of program settings, etc.). Separately, RCSM 306 may be configured to maintain/remain in a state conditioned for accepting and/or engaging in further operations relative to creating a binding relationship between IMD 402 and a patient device or controller, as exemplified by work flow 428, which may take place, for example, at a later time at the discretion of the patient in a separate registration process. Skilled artisans will recognize, however, that in some example scenarios it may be more optimal for a patient to engage in such a registration procedure with RCSM 306 following the clinician's IMD registration process while still involved in an in-person consultation with the patient because the clinician 302 and/or agent may be able to assist the patient with the process in a more personal and/or helpful setting.

FIG. 5 depicts a message/work flow diagram 500 representing operations that may be undertaken by a patient 502 having an implantable pulse generator or other device, e.g., IMD 402, for registering a patient controller or device (PC/PD) 504 at RCSM 306 and associating it with IMD 402 via a trusted relationship established thereat. In general, the patient 502 may undertake the registration process with or without a clinician being present, as noted above. Further, whereas the message/work flow 400 of FIG. 4 and the message/work flow 500 of FIG. 5 may be engaged by the clinician 302 and the patient 502 at different times (or even in different places), it is preferred that the message/work flow 400 takes place prior to the message/work flow 500. In other words, an IMD registration process involving the clinician 302 registering the patient's IMD 402 and causing the storage of the IMD's trust indicia at RCSM 306 preferably takes place prior to the patient 502 engaging in the message/work flow 500 in some example embodiments of the present disclosure. Accordingly, such backend registration of IMD-specific data (i.e., trust indicia) is exemplified as set forth at work flow block 544 in FIG. 5. Initially, the patient 502 operating PC/PD 504 may install, download or otherwise acquire a medical therapy application or "app" (e.g., via a server push, client pull, etc.), which may be representative of and/or associated with patient controller application 152 set forth in FIG. 1A in some example embodiments, from an appropriate organization, healthcare entity, facility, affiliate or service provider. Such an application may be launched or caused to be executed to present a suitable UI having various selectable options to the patient 502 in relation to device initialization, registration, therapy options and modes, and the like, as exemplified by message/work flows 506 and 508 between the patient 502 and PC/PD 504. By selecting IMD bonding mode option, a secure bonding procedure or sequence may be engaged between PC/PD 504 and the patient's IMD 402, as exemplified by message/work flows 510 and 512. In one example embodiment, the secure bonding procedure engaged by the patient 502 via PC/PD 504 may be substantially similar to the clinician's secure bonding procedure 406 set forth above, which will be further described in additional detail hereinbelow. Upon receiving a confirmation 514 that the bonding with IMD 402 is successful, an indication 516 may be provided to the patient 502 that the patient's IMD 402 is selectable for commencing a local communication session therewith using appropriate local connectivity. As with the clinician's local communications with IMD 402 (i.e., engaged when the clinician 302 and the patient 502 in proximity of each other in an in-person consultation visit), the patient's local communications with IMD 402 may be effectuated via a variety of short-range communications technologies provided with PC/PD 504, e.g., BLE, NFC, etc., as exemplified by message/work flows 518 and 520, essentially in a secure manner because of the extremely low likelihood that a malicious attacker would be able to intrude into the patient's personal space without the patient's consent or knowledge.

Upon establishing a suitable local communications channel with IMD 402, the patient 502 may select a remote programming mode to cause the generation and transmission of a device data request to IMD 524 by PC/PD 504 as exemplified by message/work flows 522 and 524. In one example embodiment, the device data request 524 may comprise a request for at least a portion of the IMD trust indicia, which may include various types of device-specific information as noted above. Responsive to receiving the requested trust indicia in a response message 526 from IMD 402, PC/PD 504 may be caused to generate and transmit a device registration request 528 including at least a portion of the trust indicia to RCSM 306 via a suitable network connection using any type of telecommunications technologies as previously noted. Responsive to the device registration request, RCSM 306 is operative to validate the received trust indicia against the stored trust indicia recorded as part of the message/work flow 400 of FIG. 4 described above. Upon successful validation of the trust indicia transmitted from PC/PD 504, IMD 402 is registered and an association record may be established indicating a trusted relationship between IMD 402 and the patient 502 and/or corresponding PC/PD 504, as exemplified by work flow 530. Thereafter, a suitable response message 532 may be generated and transmitted to PC/PD 504 that IMD 402 is registered at RCSM 306.

Subsequent to successful registration of IMD 402, PC/PD 504 may engage in a CSR process 534 with respect to one or more cryptographic keys (e.g., similar to the CSR process 336 set forth in the message/work flow 300 of FIG. 3). Accordingly, a request 536 for a digital certificate may be transmitted to RCSM 306, wherein the request 536 may include at least a portion of the IMD trust indicia. Responsive to the certificate request 536, RCSM 306 is operative to verify at least a portion of the received IMD trust indicia against the corresponding portions of the stored IMD trust indicia for a further validation 538. In one embodiment, a received RTC value may be compared against the stored RTC value to verify that both values match after accounting for the passage of a certain known time period. As there are two separate validations being performed at RCSM 306, albeit at different times, as exemplified by work flows 530 and 538, they may be referred to as first and second validations, respectively, for at least some embodiments of the present disclosure. Upon confirming that the second validation 538 is successful, RCSM 306 may propagate or relay a certificate request 540 containing additional credentials, e.g., patient's username, password, etc., depending on the level of trust required in a remote care therapy service, as well as the CSR information to a suitable key infrastructure system 599, as exemplified by message flow 540. In some embodiments, the key infrastructure system 599 employed for obtaining/generating cryptographic keys and certificates with respect to the patient 502 and/or associated PC/PD 504 may be the same as the key infrastructure system 308 employed with respect to the clinician 302 and/or associated CP/CD 304 although it is not a necessary condition. Regardless of whether two separate key infrastructure systems are utilized, skilled artisans will appreciate that where PKI systems are used for facilitating key creation, key establishment, key storage, key archival and destruction, substantially similar cryptographic processes may take place with respect to both clinician-specific and patient-specific message/work flows. Accordingly, the description set forth hereinabove with respect to the relevant portions of FIG. 3 is also equally applicable with respect the cryptographic and certificate request process of FIG. 5, mutatis mutandis. For example, some example embodiments may therefore involve providing suitable hardware, software and/or firmware as part of PC/PD 504 functionality for generating and/or obtaining a public key—private key pair combination in association with a suitable CA/RA, wherein the private key may be stored in a secure private key storage area of PC/PD 504, IMD 402 or some other trusted entity, although not all embodiments require such functionality.

In one example embodiment, if the patient 502 and/or associated PC/PD 504 was issued a previous certificate, it may be revoked by a suitable CA/RA of the key infrastructure system 599 prior to issuing a valid public key certificate, which may be propagated or otherwise relayed back PC/PD 504 as exemplified by message/work flows 542, 543 and 545. Responsive to obtaining secure communication credentials, PC/PD 504 may be configured to provide an indication 546 that the patient 502 is allowed to launch a remote care therapy session with the clinician 302, e.g., which can be either substantially immediately or at the patient's discretion, or at a subsequent time in a dynamically configured event-triggered manner.

In view of the foregoing description, it should be appreciated that devices associated with clinicians and patients for (re)programming, (re)configuring or otherwise manipulating therapy programs, settings and/or sensing functionalities of an IMD, such as CP/CD 304 and PC/PD 504, for example, may be characterized as external devices, which may be designated as a first external device, a second external device, and so on, depending on the context and/or implementation scenario. Further, as noted elsewhere in the present patent disclosure, a patient may be provided with a plurality of external devices operative with one or more IMDs of the patient (e.g., having a first IMD for SCS therapy, a second IMD for DRG therapy, a third IMD for DBS therapy, etc.), whereas the clinicians may likewise be provided with a plurality of external devices, each of which may be configured to interoperate with one or more patients and/or one or more IMDs for providing remote care therapy operations with respect to one or more therapy applications. Regardless of the specific mix of clinician devices, patient devices and IMDs deployed in a particular remote care service scenario at network level, some embodiments of the present disclosure may be configured to provide a trusted association for each device triplet of a first external device (e.g., a clinician device), a second external device (e.g., a patient device) and an IMD of the patient using the IMD trust indicia as set forth herein in order to facilitate a respective remote care service session, wherein a cloud-based RCSM may be advantageously configured to serve the entire network of the deployed devices.

Figure 9A:
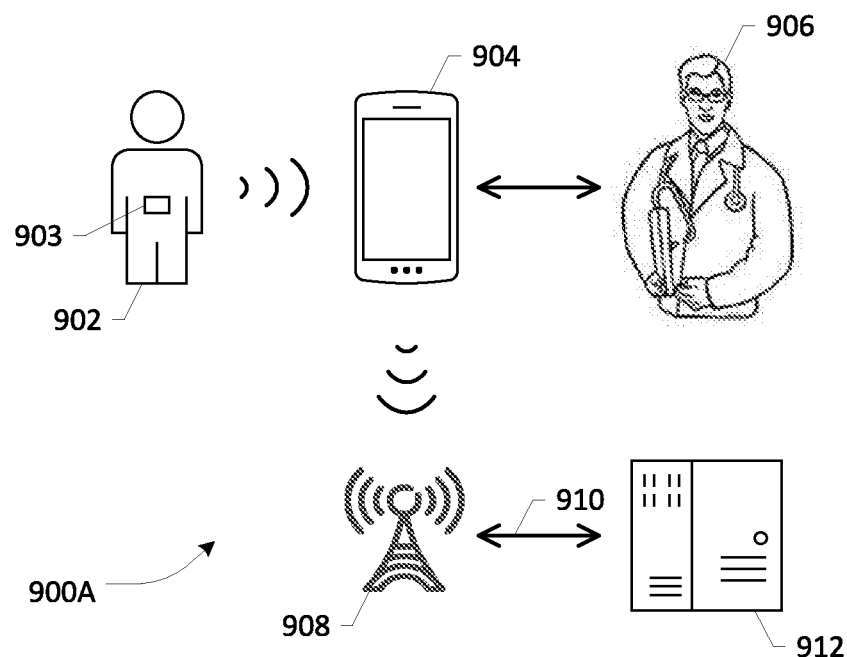
FIGS. 9A and 9B illustrate representative scenarios for facilitating therapy interactions between a patient's IMD and one or more external devices for purposes of an example embodiment of the present disclosure.
Figure 9B:
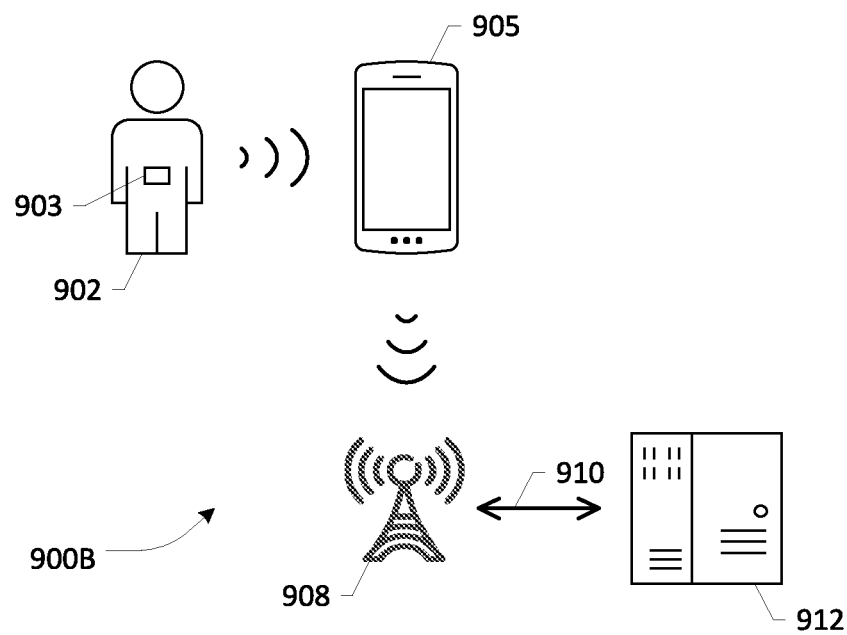

FIGS. 9A and 9B illustrate representative scenarios for facilitating therapy operations and associated interactions between a patient's IMD and one or more external devices relative to some example embodiments of the present disclosure. In particular, FIG. 9A depicts a system-level scenario 900A in which an IMD may be programmed by a clinician programmer device operating as a first external device according to some embodiments. FIG. 9B similarly depicts a system-level scenario 900B in which an IMD may be configured to communicate with a patient controller/device operating as a second external device. Further, clinician programmer devices and patient controller devices may be configured to communicate with one or more network entities, e.g., including but not limited to, remote care service manager nodes, remote device management servers, etc., according to some embodiments.

With respect to the scenario 900A of FIG. 9A, an IMD 903 is illustratively shown as implanted within a patient 902 at a suitable place proximate to a tissue/organ region of the patient 902 intended for therapy/monitoring. At appropriate times, IMD 903 is operative to communicate with a first external device, e.g., clinician controller or programmer/device 904, which is operated by a clinician or authorized agent, collectively shown as clinician 906. The programming clinician 906 utilizes one or more UI screens/windows of external device 904 to define or control a therapy provided to patient 902 mediated by the IMD 903. The clinician(s) 906 may define or set one or more therapy parameters provided as part of a therapy application. For example, without limitation, the clinician 906 may define pulse amplitudes, pulse frequencies or rates, inter-pulse time durations, pulse patterns, pacing delays, and/or a variety of other therapy parameters depending upon the IMD 903 and the intended therapy for patient 902.

During a programming session, programming data may be communicated from clinician programmer device 904 to one or more network entities, e.g., remote device management servers and/or remote care service management entities, collectively referred to as node(s) or server(s) 912, via a suitable network infrastructure 908, 910. Preferably, the set of programming data may be subjected to authorization and validation processes to ensure that only programming data from authorized clinicians will accepted by the IMD 903 of patient 902. Suitable security algorithms may be employed to validate and authorize communication between clinician programmer device 904 and servers 912, such as communication of user/clinician identifiers, passwords, device identifiers, network identifiers, security/cryptographic keys, digital certificates, location data, and/or the like.

Servers 912 may also assist in validation and creation of the programming data. For example, servers 912 may compare the programming data submitted by a clinician/agent, e.g., clinician 906, for review by one or more automated validation processes created to optimize therapies based on previously determined clinical data. If there is a discrepancy or a possible improvement, servers 912 may communicate suggested changes to the clinician(s) 906 operating device 904. Also, servers 912 may offer application services, either in association with other network entities or independently, to assist the programming process. For example, servers 912 may serve in association with one or more UE screens effectuated at device 904 using a suitable protocol (e.g., HTML) to permit the clinician(s) 906 to define, modify, intervene or otherwise modulate the therapy for patient 902 using appropriate GUIs as will be set forth further below.

When the given set of programming data is suitably defined, server(s) 912 may generate data to permit the programming data to control the therapeutic operations of the implanted medical device of patient 902. For example, if server(s) 912 determine that clinician programmer device 904 is being operated by a properly identified clinician with proper programming permissions, server(s) 912 may generate authorization and/or validation data to accompany the programming data in some embodiments. Server(s) 912 may communicate the authorization/validation data to clinician programmer device 904 via network infrastructure 908, 910. Clinician programmer device 904 communicates the programming data and the authorization/validation data to IMD 903 of patient 902, which may be configured to analyze the authorization/validation data. If the authorization/validation data is determined by IMD 903 to be valid, the IMD may conduct therapy operations (e.g., generating electrical pulses for application to tissue of the patient, delivery of pharmaceuticals, and/or the like) according to the programming data.

As used herein, validation data is data that provides information to ascertain the integrity of the programming data and/or whether the programming data was generated by a properly authorized clinician or other user for purposes of some of the embodiments of the present disclosure. Validation data may be generated by generating a value from therapeutic settings and/or programming metadata using a checksum, digest, or other suitable function. The function may include application of one or more cryptographic keys or the result of the function may be varied by application of one or more cryptographic keys. The respective keys used for cryptographic processing may include keys selected according to public-key cryptography or asymmetric cryptography (e.g., RSA (Rivest-Shamir-Adleman) cryptography and Elliptic Curve Cryptography (ECC)), and the like, although other cryptographic keys and techniques may also be used in additional or alternative implementations.

Wth respect the example scenario 900B of FIG. 9B, a patient controller/device 905 associated with patient 902 is operative as a second external device, which in turn may communicate with server(s) 912. Patient 902 may utilize device 905 for one or more of a variety of tasks relating to telehealth consultations, allowing/approving remote therapy operations, interrupting the therapy when desired, IMD maintenance, etc. For example, patient 902 may interact with device 905 to check the status of the patient's IMD 903 (battery level, existing operating mode, etc.). Also, IMD 903 may be configured to monitor physiological signal or processes of the patient 902, which may be stored locally within IMD 903 and/or in the external device 905. For example, patient controller device 905 may communicate with IMD 903 periodically or upon detecting certain triggered events to access stored physiological data, which may be communicated in a remote therapy/monitoring session to a networked entity and/or an authorized clinician. The patient controller device 905 may display a suitable indication of the patient's condition (e.g., heart rate, glucose level, neurological activity, etc.) using audio, visual, textual means. The accessed physiological or other patient data may also be communicated to one or more external servers, e.g., servers 912, which may be accessed by the clinician while engaged in a remote therapy and/or telehealth session with the patient 902 in accordance with some embodiments. The physiological data may be analyzed to monitor the patient's condition, for example, to identify if the patient is experiencing undesired physiological conditions, e.g., cardiac conditions such as episodes of tachycardia, arrhythmias, and other conditions. Automated processing may occur to identify relevant medical conditions, e.g., based on artificial intelligence (AI) and/or machine learning (ML) techniques in association with "Big Data" analytics. Alerts to the patient 902 and/or to the patient's medical professionals may be provided by the patient controller device 905 and/or server(s) 912 if warranted by the physiological data in some implementations.

Also, depending upon the type of IMD 903, patient 902 may interact with external device 905 via suitable GUIs to control one or more aspects of the patient's therapy. For example, some neuromodulation devices frequently include multiple stimulation programs, and depending upon the patient's experience of pain at any given time, the patient may switch between available programs to select the program that provides the most suitable pain relief. Also, patient controller device 905 may enable patient 902 to control stimulation amplitude (for certain neurostimulation devices). For example, patient 902 may enter relevant information via one or more UI screens to control stimulation depending on patient's pain condition, activity level, etc. Further, IMD 903 may automatically employ different therapy settings when the patient 902 is asleep or when the patient is active. In other arrangements, IMD 903 may modify operations depending upon the intake or ingestion of pharmaceutical agents by patient 902. The patient 902 may enter relevant information via external device 905 to indicate such events. Still further, patient 902 may opt to stop, pause, or temporarily suspend a remote therapy session while maintaining AV connectivity with the clinician in some embodiments as will be set forth further below.

In some embodiments, a historical record of all such interactions, modifications, reconfigurations, etc., with respect to IMD 903 and patient device 905 may be maintained and transmitted to servers 912, along with any user-labeled data, which may be AV data, network performance data, therapy settings data, etc. indicative of either patient's and/or clinician's characterization of the data during therapy sessions. Clinicians may access such data either from servers 912 or from patent controller device 905 or from IMD 903 via a networked session with the patient 902 for facilitating/enhancing a remote care therapy consultation. For example, In a remote care therapy scenario, a clinician may not only be able to monitor and evaluate the patient based on a number of real-time variables such as, e.g., patient's facial features, physiological conditions, patient's responses to questions, etc., but also access the historical record of patient interactions with the IMD and utilize that information in providing appropriate therapy, wherein the communications between the patient and the clinician are advantageously protected. Accordingly, skilled artisans will recognize that the foregoing example scenarios 900A, 900B may be combined in a variety of more comprehensive use case scenarios wherein different aspects of the present disclosure may be practiced in different combinations for purposes of one or more embodiments according to the teachings herein. Further, some of the embodiments may be practiced after performing the requisite work flows relating to device registration and establishment of trusted associations as set forth in FIGS. 3-5 described hereinabove, although it is not requirement as noted previously.

Figure 10:
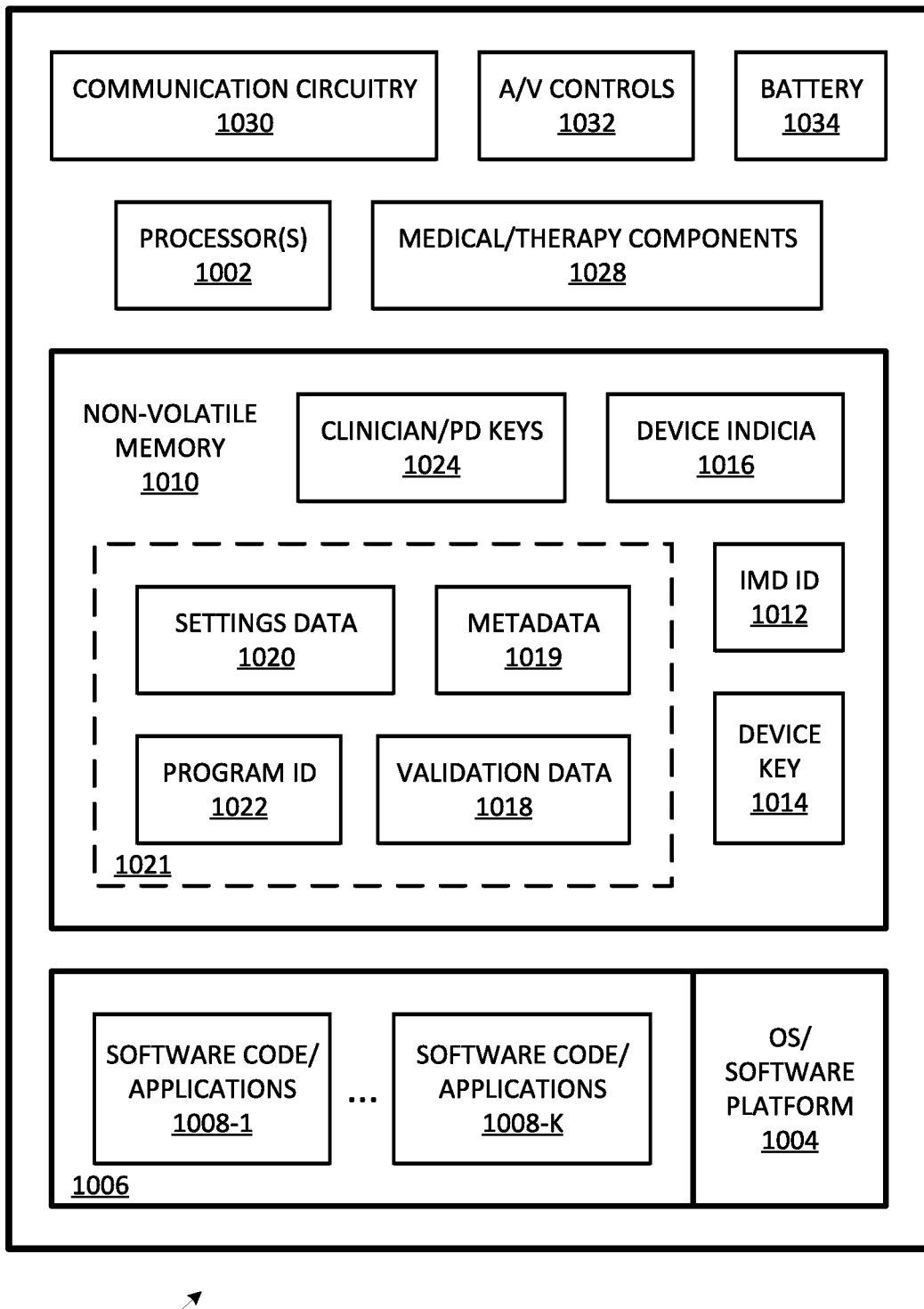
FIG. 10 depicts a block diagram of a personal or patient medical device according to some example embodiments.
Figure 11:
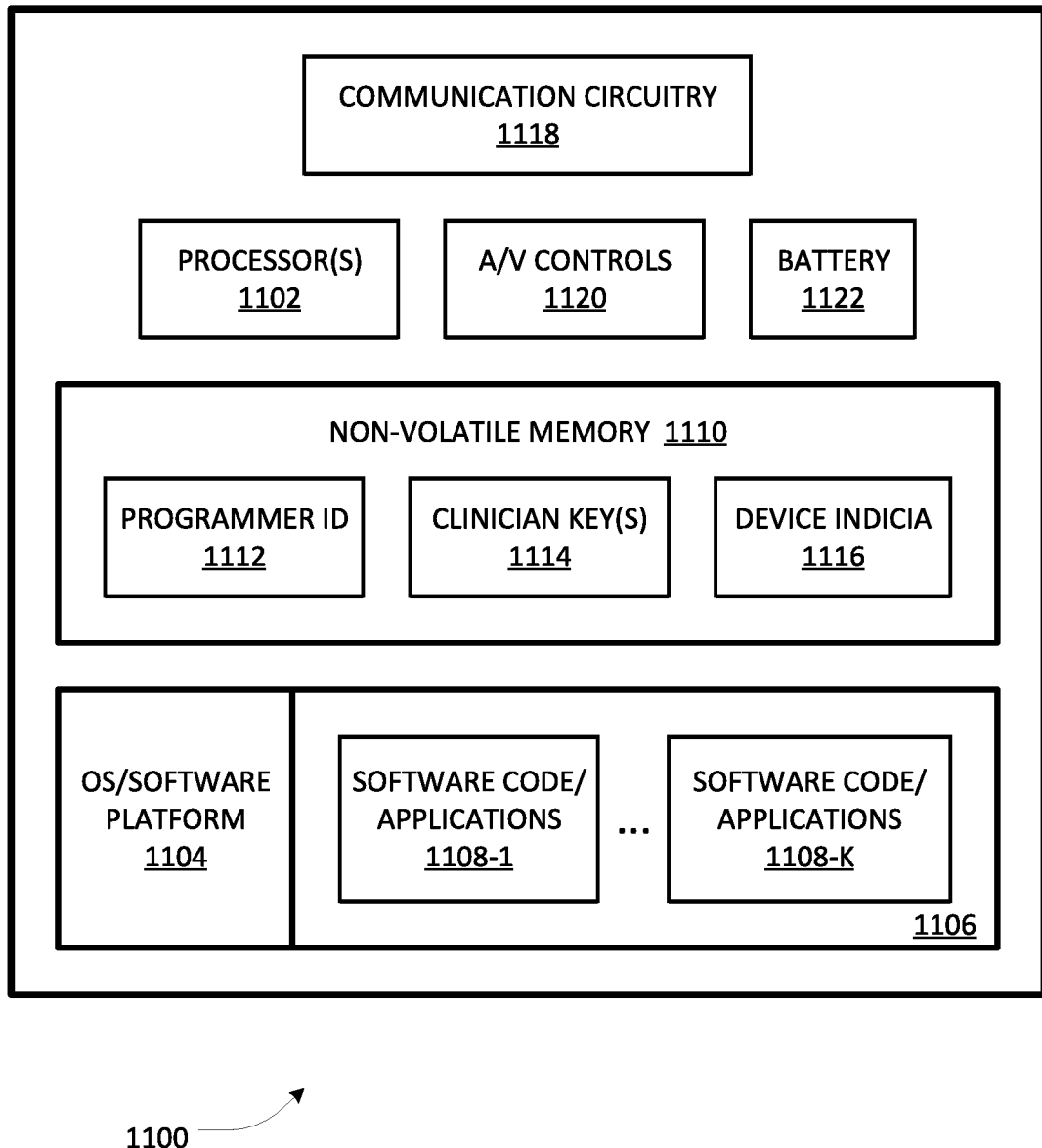
FIG. 11 depicts a block diagram of a clinician controller device according to some example embodiments.

FIGS. 10 and 11 depict block diagrams of a patient medical device 1000 and a clinician device 1100, respectively, that may be configured to operate according to some example embodiments of the present disclosure. In some implementations, at least portions of medical device 1000 may be arranged as an implantable medical device. In other arrangements, different portions of device 1000 may be configured so as to operate as a patient controller device. In general, device 1000 preferably includes one or more processors or controllers 1002 to control overall device operations, including operations relating to one or more medical therapy components 1028 to provide appropriate therapy to the patient and/or to monitor or measure one or more physiological conditions of the patient based on suitable hardware/software modules, all being powered by a power supply, e.g., battery 1034. In one arrangement, device 1000 may include suitable communications circuitry 1030 to conduct communication sessions with an external device (e.g., clinician device 1100 described in detail below and/or a patient device) after implantation using any known or heretofore unknown short-range communications technologies, e.g., involving communication protocols that may include but not limited to inductive communication protocols, BLE, NFC, Zigbee, UHF RFID, Bluetooth, and the like. In one arrangement, communications circuitry 1030 of device 1000 may also include circuitry to conduct communication sessions with networked devices over a network using appropriate technologies as set forth above in reference to FIGS. 1A and 1B. Further, device 1000 may include one or more OS platforms 1004 and one or more software applications 1008-1 to 1008-N depending on configuration, collectively referred to as device software environment 1006, which may be operative to effectuate a patient controller application, e.g., application 152, for facilitating integrated telehealth and remote care therapy sessions as noted above. Device 1000 may include one ore more memory modules 1010 including, e.g., non-volatile memory modules, to store executable instructions and data. In one arrangement, the stored data may include a device identifier 1012, one or more device keys 1014 and one or more device trust indicia 1016. For example, device key storage 1014 may store one of a pair of asymmetric encryption keys with the other key stored by a remote server, e.g., a PKI server or other server. The pair of keys for a given device 1000 may be used to securely create and employ validation data according to some embodiments. Although device identifier 1012 is shown as stored in memory 1010, device identifier 1012 may be retained elsewhere in device 1000. For example, many device components (e.g., processors, integrated circuits, wireless communication circuitry, and the like) include identifiers that are hard-encoded in the components and are readily retrievable. In one embodiment, the identifiers of such subcomponents may be used, taken alone or in some combination, as the medical device identifier in lieu of a value stored in memory of device 1000. Memory 1010 may also include storage for additional software code to control certain aspects of device 1000, which may include code or program instructions to implement operations relating to remote care therapy applications according to the embodiments herein, e.g., therapy modulation, data labeling/ record generation, etc.

Device 1000 may include one or more instances of programming data 1021 in memory 1010 that may be configured to define how device 1000 conducts therapeutic or medical operations according to some embodiments. In some embodiments, each instance of programming data 1021 may include a program identifier 1022. Also, each instance of programming data 1021 may include a field for device identifier data (not specifically shown), which may be compared against the device identifier 1012 to ensure that the programming data 1021 is intended for use by the specific device 1000. Further, each instance of programming data 1021 may include settings data 1020, e.g., comprising various device parameters that define the therapeutic or medical operations to be provided by device 1000. For example, in an embodiment involving a neurostimulation device for chronic pain, the settings data may include an electrode configuration for delivery of electrical pulses, a stimulation pattern identifier (tonic stimulation, burst stimulation, noise stimulation, and/or the like), pulse parameters, one or more frequency parameters, cycling parameters, timing parameters, and/or the like. Still further, each instance of programming data 1021 may be accompanied with its respective metadata 1019, which may include data that identifies the physician or clinician that created or programmed the settings data. In some embodiments, the metadata 1019 may include an identifier of the clinician programmer device that was used to create the settings data, the date of creation, the data of last modification, the physical location where programming occurred, and/or any other relevant data. Each instance of programming data 1021 may also include appropriate validation data 1018. For example, the validation data may be used by device 1000 to ensure that the settings data is intended for device 1000 and is properly authorized to control/configure the device operations. In some embodiments, validation data may be created using a checksum algorithm, a cryptographic hash function, and/or similar suitable processing, as note previously. For example, some of the programming data 1021 may be represented by a plurality of characters in respective strings, wherein each character in sequence may be applied to a hash function or suitable function to generate an output hash value or similar value which may be verified by known checksum functions and/or modular sum operations. Furthermore, the checksum value or other relevant data may be encrypted with a suitable cryptographical key (e.g., the corresponding key of the key pair used for device 1000). The encrypted data may then be stored in device 1000 as the validation data in some embodiments. A separate storage area 1024 may be provided for securely storing applicable CD/PD keys used for securing communications with respect to remote care therapy sessions according to some embodiments. Where device 1000 is configured as a patient controller device, it may also include appropriate AV controls 1032 operative with suitable GUIs for purposes of some example embodiments of the present disclosure.

Example clinician device 1100 may include one or more processors 1102, communications circuitry 1118 and one or more memory modules 1110, operative in association with one or more OS platforms 1104 and one or more software applications 1108-1 to 1108-K depending on configuration, cumulatively referred to as CD software environment 1106, and any other hardware/software/firmware modules, all being powered by a power supply, e.g., battery 1122. Example OS platforms may include, without limitation, iOS, Android, Chrome OS, Blackberry OS, Ubuntu, Sailfish OS, Windows, Kai OS, etc. In some embodiments, at least a portion of the software applications may include code or program instructions configured to execute various operations relative to device registration and establishment of trusted associations at a remote care session manager or server, which may be executed in association with and/or as part of a clinician controller application, e.g., application 182 as set forth in FIG. 1A. Memory modules 1110 may include non-volatile memory configured to store relevant data and software code (not specifically shown) to control overall operation of device 1100. Memory 1110 may include storage 1112 to store a programmer identifier (e.g., a serial number) of device 1100 used during programming sessions (e.g., local programming or remote session programming). Also, memory 1110 may store one or more clinician keys 1114 and one or more device indicia 1116 for use during programming and/or remote care therapy as discussed herein. Communications circuitry 1118 may include wireless and/or wireline communication capabilities, inductive communication capabilities, to effectuate IMD communications as well as networked communications as set forth hereinabove. Similar to device 1000, clinician device 1100 may also include appropriate AV controls 1122 operative with suitable GUIs for purposes of some example embodiments of the present disclosure, which may include, e.g., therapy modulation, data labeling/record generation, etc.

Figure 12:
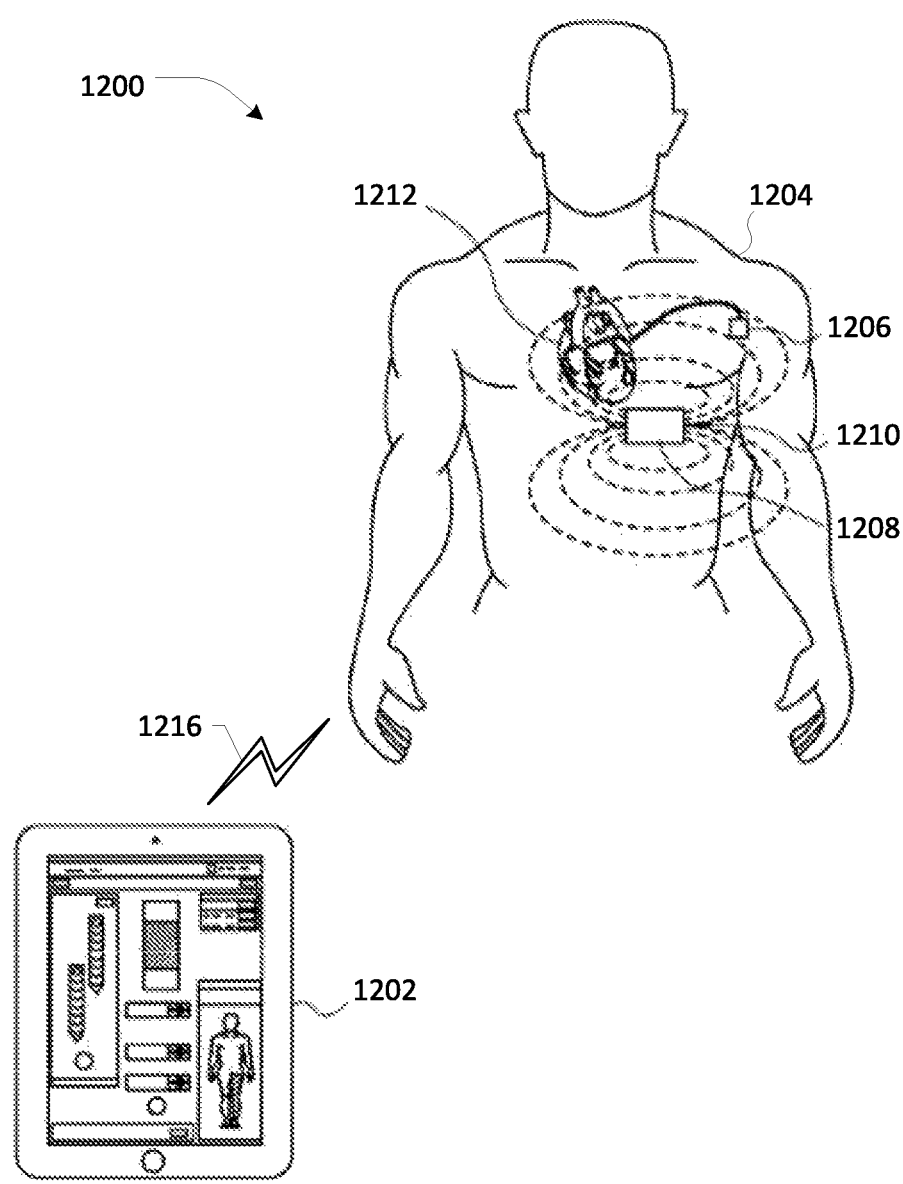
FIG. 12 depicts a block diagram of a system for initiating a bi-directional communication link for purposes of an example embodiment of the present disclosure.

FIG. 12 depicts a block diagram of a system 1200 as a non-limiting example for effectuating initial bonding associations between an external device and an IMD via a local bi-directional communication link when they are in proximity of each other in some embodiments of the present disclosure. By way of illustration, system 1200 is representative of a scenario to provide a pairing and/or bonding procedure between two devices using a proximate triggering device, e.g., when a patient device (e.g., PC/PD 504) or a clinician device (e.g., CP/CD 304) is within the vicinity or presence of a patient having the IMD. In general operation, the triggering device may be configured to emit or transmit an activation field, which may be detected by the IMD. When the activation field is detected by the IMD, the IMD may enter or transition into a communication initialization mode corresponding to a preconfigured pairing and/or bonding procedure involving known or heretofore unknown communication protocols. For example, the pairing and/or bonding procedure may be defined by a wireless protocol (e.g., Bluetooth, BLE, ZigBee, etc.). The pairing and/or bonding procedure may include exchanging information to generate passkeys in both the IMD and an external device to establish a communication link. A technical effect of this embodiment is to strengthen pairing and/or bonding procedures for wireless protocols by providing proximity detection based on the triggering device and the activation field for the pairing and/or bonding procedure of available wireless protocols. Another technical effect of positioning the triggering device proximate to the IMD, thereby the patient, is awareness of the patient and proximity protection against the IMD initiating a communication link from an untrusted or unauthorized external device.

Illustratively, system 1200 is exemplified with an IMD 1206, a triggering device 1208 (e.g., a magnet, an inductive communication circuit, an NFC circuit, an electric motor, etc.), and an external device 1202, which may be operative as a clinician device or a patient device according to an embodiment. IMD 1206 may be implanted within a patient 1204 (e.g., proximate to the patient's heart 1212, proximate to the spinal cord, proximate to or within the brain, or proximate to some other tissue/organ of interest). Additionally or alternatively, IMD 1206 may have components that are external to the patient 1204. For example, IMD 1206 may include a wearable/external pulse generator (EPG) for providing appropriate stimulation pulses operative to be transmitted to one or more regions via IMD 1206.

The triggering device 1208 is operative to produce or generate an activation field 1210. IMD 1206 may be configured to detect the activation field 1210 when the IMD is passed through and/or placed within the activation field 1210. The activation field 1210 from the triggering device 1208 may comprise at least one of a magnetic field, NFC transmission, RFID transmission, an inductive telemetry signal, or a vibration scheme resulting in displacement of a position of the IMD 1206. The activation field 1210 may be defined by an effective distance or area from the triggering device 1208 where the activation field 1210 may be detected by IMD 1206. Optionally, the triggering device 102 may continually produce or emit the activation field 1210. For example, the activation field 1210 may include a magnetic field generated by a magnet of the triggering device 102. Additionally or alternatively, the activation field 1210 may be activated by a user. For example, the activation field 1210 may include an NFC transmission generated by an NFC circuit of the triggering device 1208, which is activated by the user when positioned proximate to the IMD 1206.

When the activation field 1210 is detected by the IMD 1206, the IMD 1206 may be programmed and/or configured to enter into a select communication initialization mode corresponding to the activation field 1210 generated from the triggering device 1208. The select communication initialization mode may comprise a subset of a plurality of communication initialization modes defined by the wireless protocol to establish a bi-directional communication link 1216 between the IMD 1206 and the external device 1202. For example, the communication initialization mode may correspond to a defined pairing and/or bonding procedure. Optionally, the communication initialization mode may comprise transitioning the IMD 1206 from a sleeping and/or power saving state by activating a radio frequency (RF) circuit (not specifically shown in this FIG.). Additionally or alternatively, the IMD 1206 may determine which communication initialization mode is selected based on a field characterization of the activation field, such as, e.g., a strength, frequency, phase and/or select characteristic value of the activation field 1210. For instance, the IMD 1206 may identify a magnetic field strength and/or flux of the activation field 1206 at a first value corresponding to a communication initialization mode for initiating the pairing and/or bonding procedure between the IMD 1206 and the external device 1202. In another example, the IMD 1206 may detect a magnetic field strength and/or flux of the activation field 1210 at a second value corresponding to a communication initialization mode for activating the RF circuit of the IMD 1206 for reestablishing the bi-directional communication link 1216 with a previously bonded and/or paired external device 1202.

The external device 1202 may be configured to establish the bi-directional communication link 1216 with the IMD 1206 so as to facilitate the external device 1202 to receive measurements from the IMD 1206 and/or to program or send instructions to the IMD 1206. As noted previously, the bi-directional communication link 1216 may use any standard wireless protocols. Additionally, some example embodiments may involve establishing the bi-directional communication link 1216 using certain healthcare-specific communications services including, e.g., Medical Implant Communication Service, Wireless Medical Telemetry Service, Medical Device Radiocommunications Service, Medical Data Service, etc. The external device 1202 may be located within a home of the patient, a hospital, an automobile, at an office of the patient/clinician, or the like. Accordingly, the example system 1200 may be implemented as a secure bonding procedure within the context of the message/work flows of FIGS. 4 and 5 in some example embodiments of the present disclosure. Whereas the IMD 1206 is particularly exemplified as a cardiac medical device in the system 1200, it should be understood that IMD 1206 is broadly representative of any type, category or class of implantable bioinstrumentation devices as noted previously. Additional details regarding the initiation of a bi-directional communication link between two devices using a proximate triggering device may be found in U.S. Pat. No. 9,288,614, entitled "SYSTEMS AND METHODS FOR INITIATING A COMMUNICATION LINK BETWEEN AN IMPLANTABLE MEDICAL DEVICE AND AN EXTERNAL DEVICE", which is incorporated by reference herein. It should be appreciated that although a trigger-based pairing bonding procedure between two medical devices has been set forth above, it is not a requirement for purposes of some example embodiments of the present patent disclosure.

Turning now to FIGS. 6A-6D, depicted therein are flowcharts illustrative of blocks, steps and/or acts that may be (re)combined in one or more arrangements with or without additional flowcharts of the present disclosure for facilitating remote care therapy in some example embodiments. Example process 600A of FIG. 6A may be commenced by registering a first external device (e.g., a clinician controller device) with a remote care session manager disposed in a network (block 602). At block 604, secure communication credentials are obtained/generated for the first external device using a key infrastructure system. At block 606, a trusted association is established between the first external device and a patient's IMD at the remote care session manager when the first external device and the patient are in proximity of each other. At block 608, a trusted association is established between the IMD and a second external device (e.g., a patient controller device) at the remote care session manager when the second external device and the patient are in proximity of each other. At block 610, secure communication credentials are obtained/generated for the second external device using the key infrastructure system. Thereafter, a secure communications session may be launched between the first and second external devices to effectuate one or more telehealth and/or remote care therapy operations relative to the patient, wherein the first external device is remote from the second external device and the second external device is in proximity of the patient, such remote care therapy operations being mediated between the first external device and the IMD of the patient (block 612). As will be set forth further below, the remote care therapy operations may be modulated or otherwise intervened by a patient and/or clinician and/or by way of programmatic control in some embodiments.

Figure 6A:
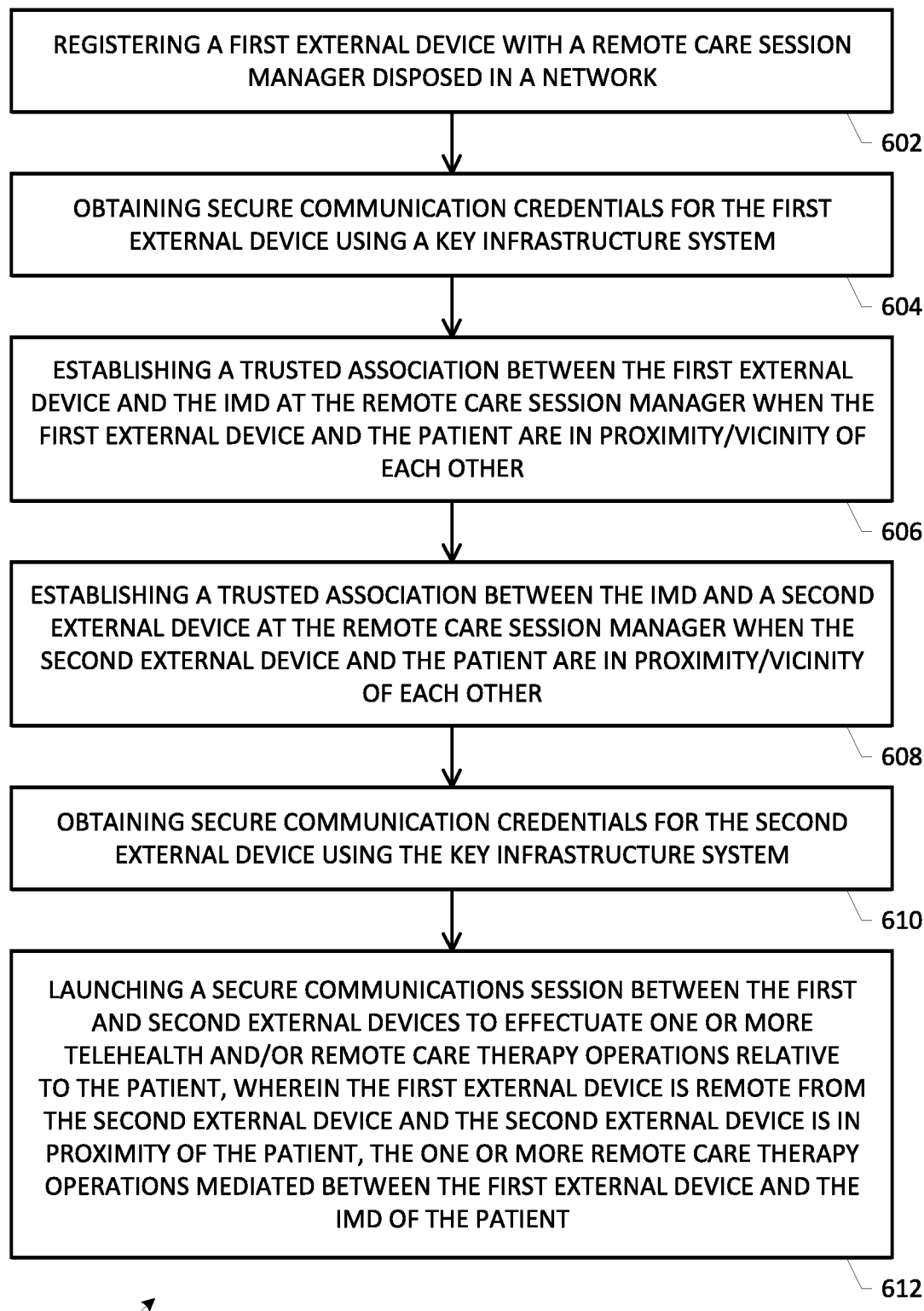
FIGS. 6A-6D depict flowcharts illustrative of blocks, steps and/or acts that may be (re)combined in one or more arrangements with or without additional flowcharts of the present disclosure for facilitating remote care therapy according to some embodiments.
Figure 6B:
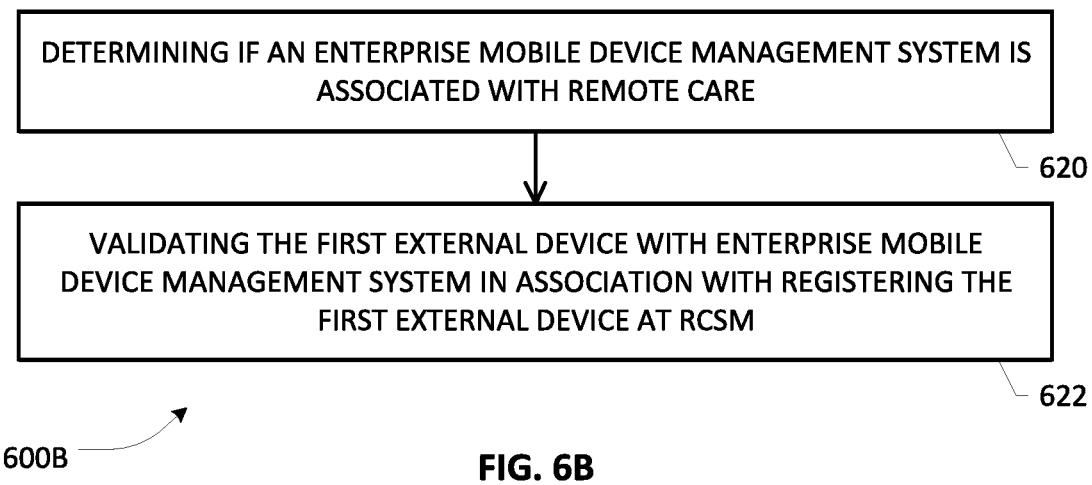
Figure 6C:
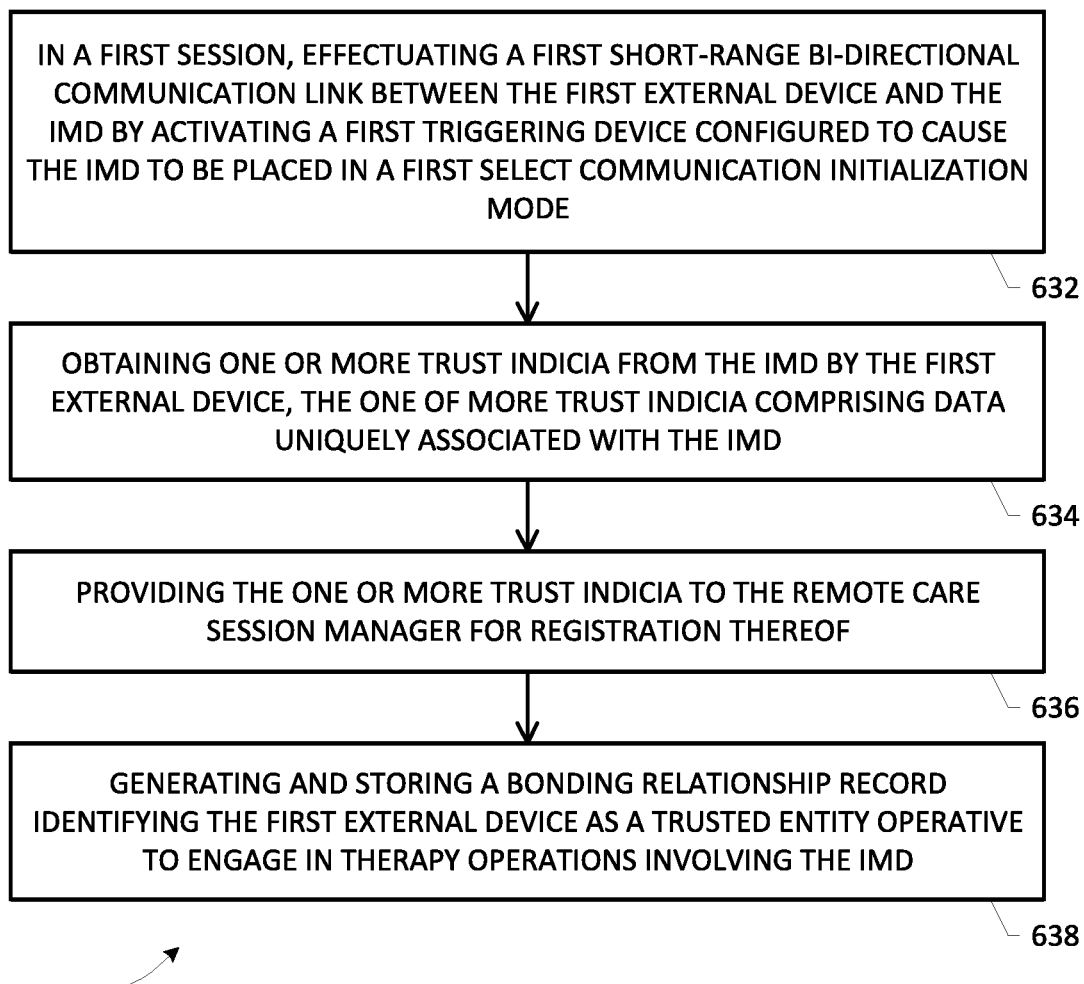

Example process 600B of FIG. 6B involves determining if an enterprise device management is associated with remote care therapy services in some embodiments, as set forth at block 620. If so, the first external device is validated with the enterprise device management system before registering the first external device in association with the remote care session manager (block 622). Example process 600C of FIG. 6C is representative of a trust association establishment process with respect to the first external device and the patient's IMD in some embodiments. In a first session, when the devices are in close proximity, a first short-range bi-directional communication link may be effectuated between the first external device and the IMD by activating a first triggering device configured to cause the IMD to be placed in a first select communication initialization mode (block 632). At block 634, one or more trust indicia are retrieved or otherwise obtained from the IMD by the first external device, wherein the one or more trust indicia comprises data uniquely associated with the IMD. As noted previously, various pieces of data or information may be provided to operate as such trust indicia. At block 636, at least a portion of trust indicia may be transmitted to the remote care session manager for registration of the IMD therewith. At block 638, a bonding relationship record may be created and stored that includes suitable information for identifying or otherwise indicating the first external device as a trusted entity operative to engage in therapy operations involving the IMD.

Figure 6D:
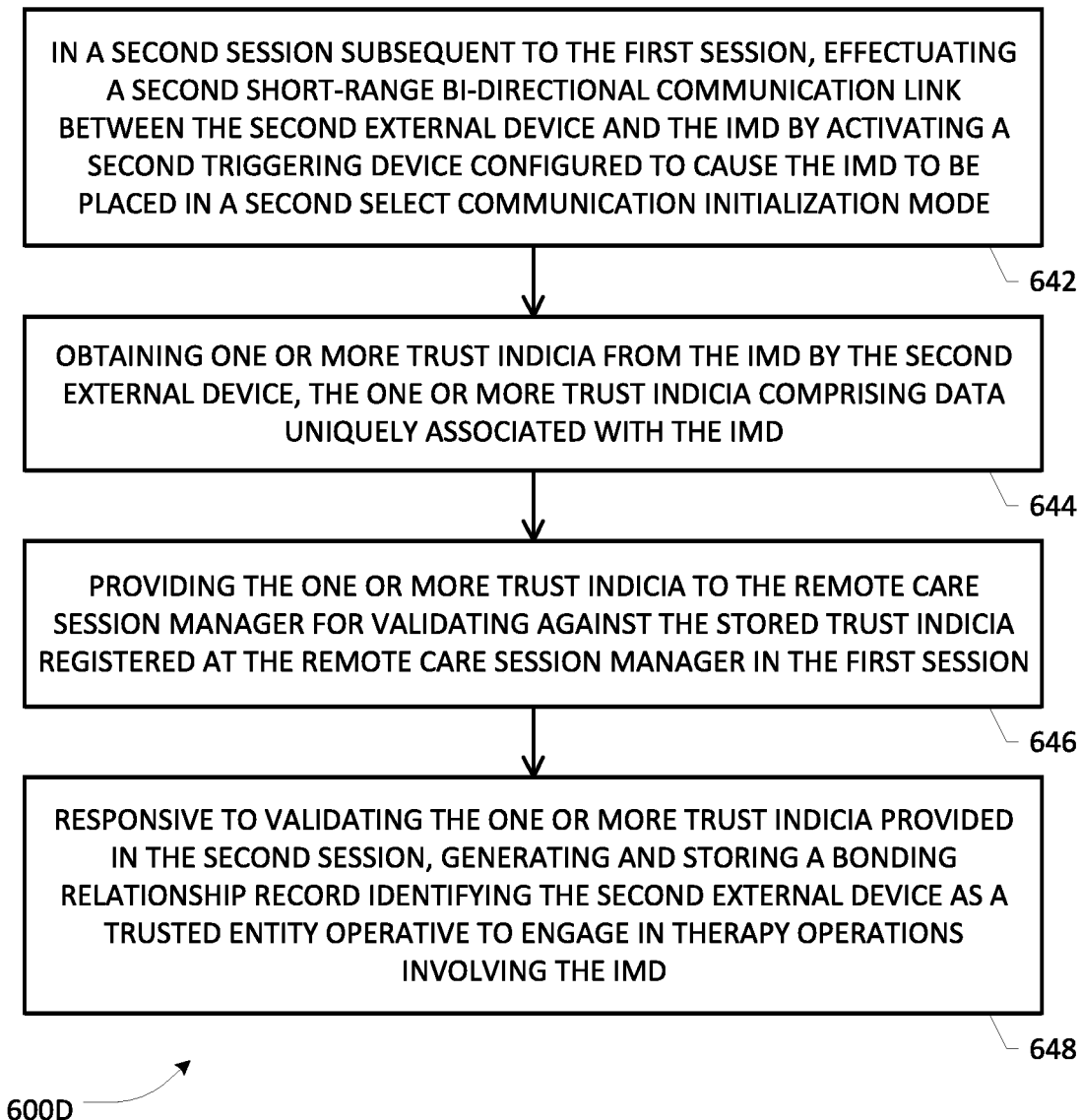

Example process 600D of FIG. 6D is representative of a trust association establishment process with respect to the second external device and the patient's IMD in some embodiments. In a second session subsequent to the first session, a second short-range bi-directional communication link may be effectuated between the second external device and the IMD by activating a second triggering device configured to cause the IMD to be placed in a second select communication initialization mode (block 642). In some example embodiments, different types of triggering devices and/or technologies may be used with respect to the respective secure bonding processes of the first and second external devices. At block 644, one or more trust indicia are retrieved or otherwise obtained from the IMD by the second external device, wherein the one or more trust indicia comprises data uniquely associated with the IMD. At block 646, at least a portion of the trust indicia is transmitted to the remote care session manager for validating against the stored trust indicia registered at the remote care session manager in the first session. Responsive to validating the one or more trust indicia provided in the second session, a bonding relationship record may be generated and stored at the remote care session manager for identifying/indicating the second external device as a trusted entity operative to engage in therapy operations involving the IMD.

Figure 7:
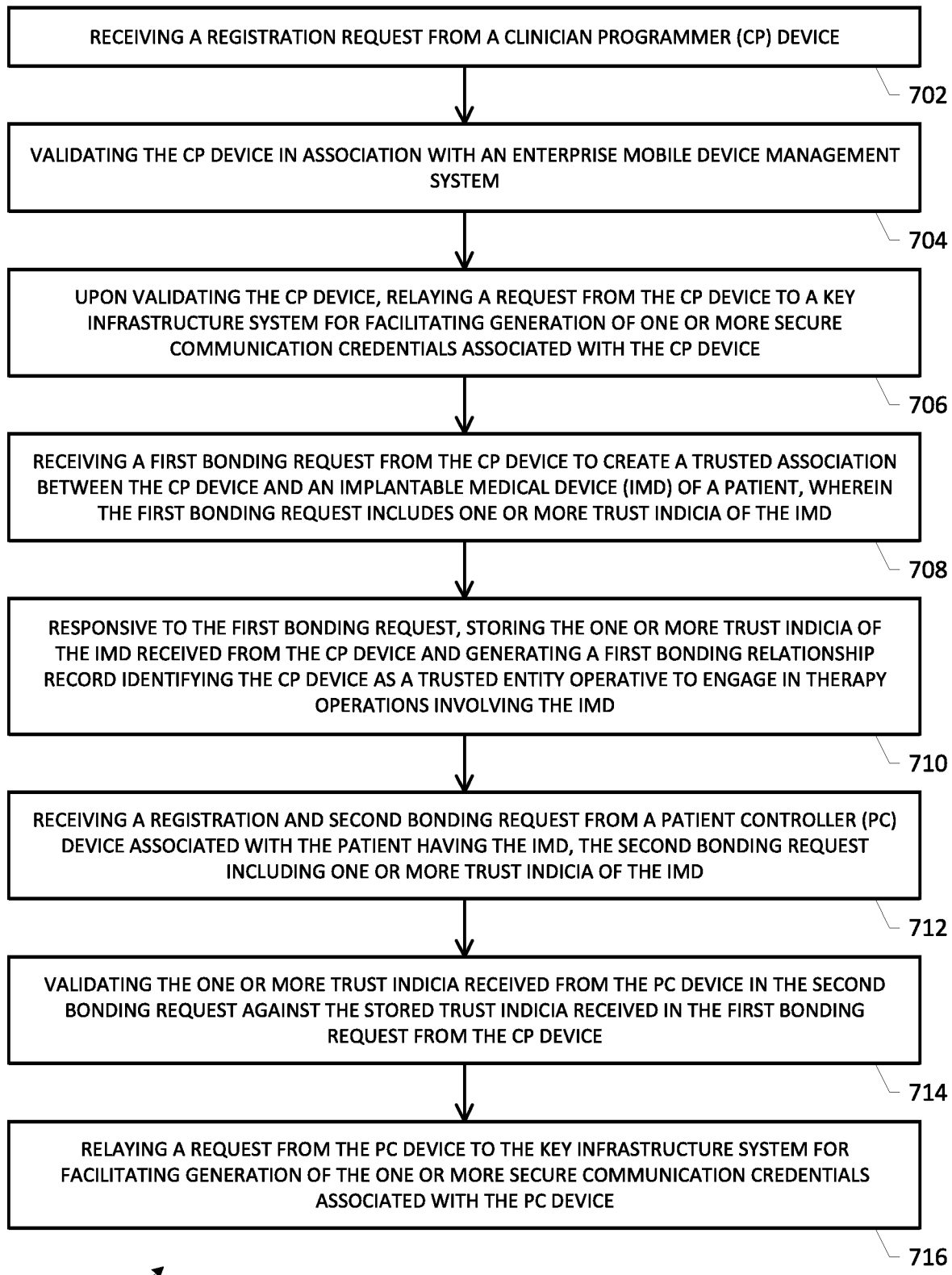
FIG. 7 depicts a flowchart illustrative of blocks, steps and/or acts that may be implemented at a remote care session manager for purposes of an example embodiment.

FIG. 7 depicts a flowchart illustrative of a process 700 comprising various blocks, steps and/or acts that may take place at a remote care session manager in some example embodiments of the present disclosure. At block 702, a registration request is received from a clinician programmer (CP) device (i.e., a first external device). At block 704, the CP device is validated by the remote care session manager, preferably or optionally in association with an enterprise mobile device management system. At block 706, upon validating the CP device, a request from the CP device is relayed to a key infrastructure system for facilitating generation of one or more secure communication credentials associated with the CP device. At block 708, a first bonding request is received from the CP device to create a trusted association between the CP device and an IMD of a patient, wherein the first bonding request includes one or more trust indicia of the IMD. Responsive to the first bonding request, the remote care session manager stores the one or more trust indicia of the IMD received from the CP device and generates a first bonding relationship record identifying the CP device as a trusted entity operative to engage in therapy operations involving the IMD (block 710). At block 712, a registration and second bonding request is received from a patient controller (PC) device (e.g., a second external device) associated with the patient having the IMD, the second bonding request including one or more trust indicia of the IMD. At block 714, the remote care session manager is operative to validate the one or more trust indicia received from the PC device in the second bonding request against the stored trust indicia received in the first bonding request from the CP device. Thereafter, upon successful validation, a request from the PC device is relayed to the key infrastructure system for facilitating generation of one or more secure communication credentials associated with the PC device (at block 716).

Skilled artisans will recognize that some of the blocks, steps and/or acts set forth above may take place at different times (i.e., asynchronously), and possibly with intervening gaps of time and/or at different places, as noted elsewhere in the present patent application. Accordingly, it should be appreciated that the process flows (as well as the message/work flows set forth in FIGS. 3-5) may be interleaved with one or more sub-processes comprising other IMD<=>patient or IMD<=>clinician interactions (e.g., local therapy sessions), which may alter, modify or otherwise reconfigure the processes and message/work flows of the present disclosure in some embodiments.

FIG. 8A-8E depict flowcharts illustrative of a remote care therapy scenario that may be implemented in a system architecture and network environment shown in FIGS. 1A and 1B, wherein an integrated remote care session may be established between a patient and a clinician operating respective controller devices according to some example embodiments of the present disclosure. As will be set forth further below, patient/clinician controller devices may be provided with appropriate application software to effectuate suitable GUIs on respective devices for facilitating a remote care session including a secure AV session/channel and a therapy session/channel as part of a common application interface. Process flow 800A of FIG. 8A may commence with a patient launching a therapy application executing on the patient controller/device to initiate a secure communications channel with a remote clinician (block 802), e.g., by selecting a "Remote Care" option from a pull-down menu, clicking on an icon on the UI display screen, or via a voice command, etc. In one embodiment, the patient may be ushered into a virtual waiting room, which may be realized in a UI screen window of the patient/clinician controller/device (block 804). At block 806, the clinician responds to the waiting patient, e.g., via a secure AV communication channel of the remote care session. At block 808, one or more physiological/biological variables (stored or real-time) may be provided to the clinician via secure communications (e.g., facilitated via a Transport Layer Security (TLS)-based path based on the encryption keys). In some embodiments, data may be encrypted using the clinician's public key, and optionally signed by using the patient's private key. At block 810, the clinician evaluates the patient in view of the physiological/biological data, telemedicine/video consultation, audio/visual cues and signals regarding patient's facial expressions, hand movement/tremors, walking, gait, ambulatory status/stability, and other characteristics to arrive at appropriate medical assessment. Depending on such telehealth consultation/evaluation, the clinician may remotely adjust therapy settings for secure transmission to the patient device, which may be securely transmitted via encrypted communications (e.g., encrypted using the patient's public key, and optionally signed by using the clinician's private key). In a further scenario, a remote clinician proxy or agent may be executed at or in association with the patient controller/device upon launching a remote session, wherein the proxy/agent is operative to effectuate or otherwise mediate the transmission of any therapy settings to the patient's IMD, either in real-time or at some point in the future depending upon programmatic control. After completing the therapy and consultation, the remote care session may be terminated, e.g., either by the clinician and/or the patient, as set forth at block 812.

Figure 8A:
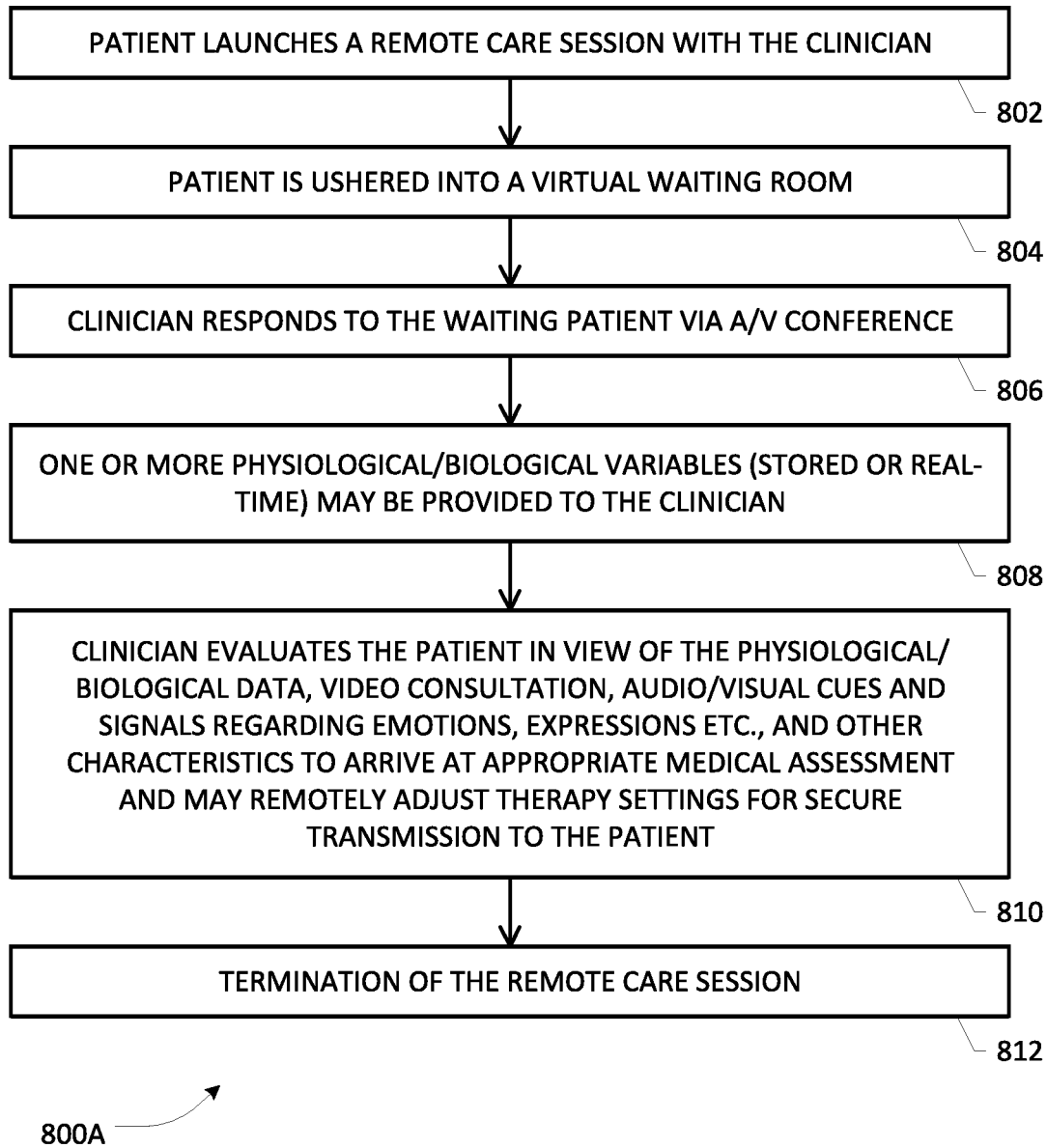
Figure 8B:
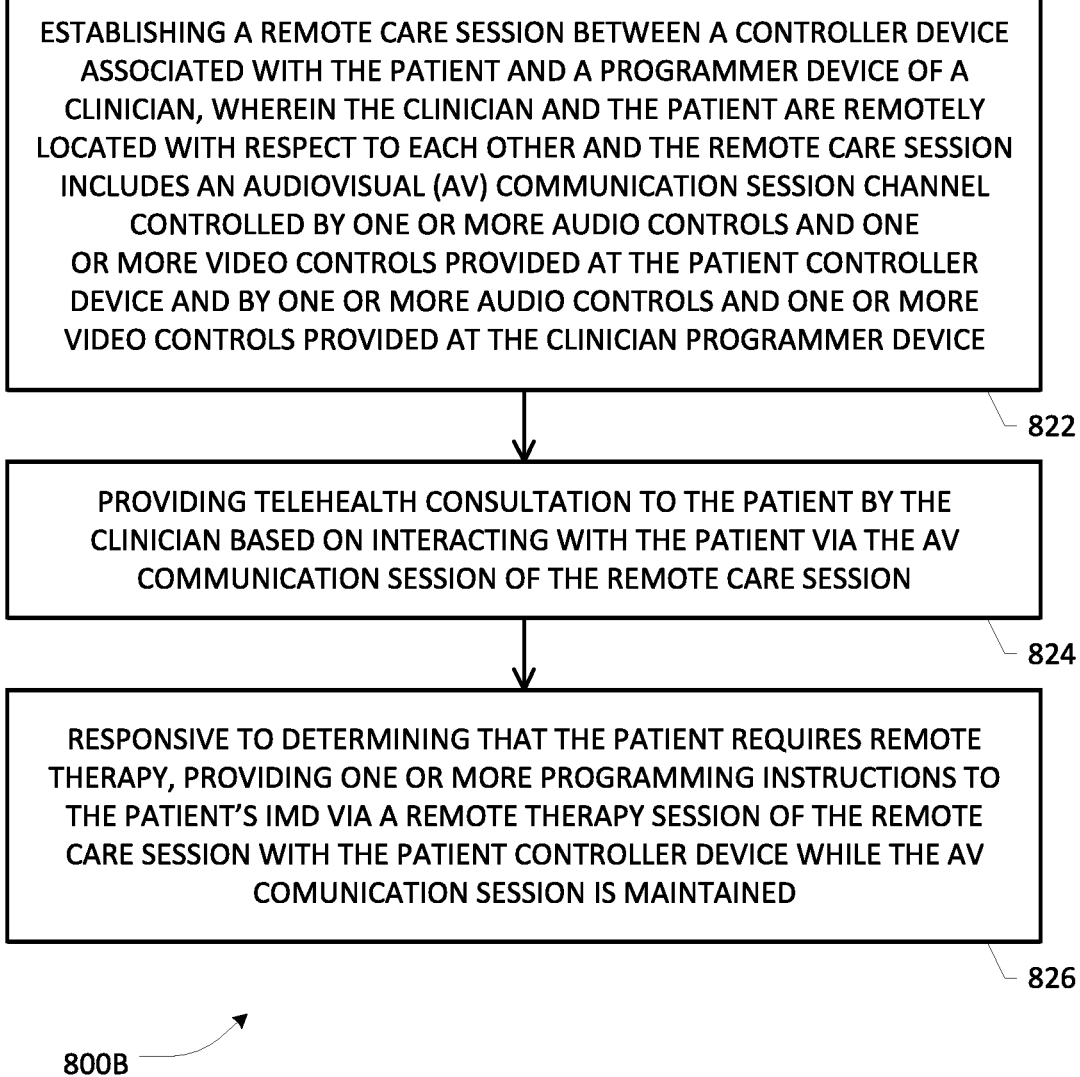

Process flow 800B of FIG. 8B is illustrative of an embodiment of a high level scheme for delivering healthcare to a patient via an integrated remote care session. At block 822, a remote care session between a controller device associated with the patient and a programmer device associated with a clinician may be established, wherein the clinician and the patient are remotely located with respect to each other and the remote care session includes an AV communication session controlled by one or more A/V controls provided at the patient controller device and the clinician programmer device. As noted above, an example remote care session may be launched after device registration, establishment of trusted associations among the devices, installation of credentials for secure communications, etc. have already taken place according to some embodiments. At block 824, various telehealth consultation services may be provided to the patient by the clinician based on interacting with the patient via the AV communication channel of the remote care session as previously noted. Responsive to determining that the patient requires remote therapy, one or more remote programming instructions may be provided to the patient's IMD via a remote therapy session or channel of the remote care session with the patient controller device while the AV communication session is maintained (block 826).

In some implementations, the foregoing methodology may be modified, refined, altered and/or augmented in various ways according to the teachings of the present disclosure. In one embodiment, an example remote care session may be established between the patient controller device and the clinician programmer device after the patient has activated a suitable GUI control provided as part of a GUI associated with the patient controller device and the clinician has activated a corresponding GUI control provided as part of a virtual waiting room displayed on a GUI associated with the clinician controller device, as set forth at block 832 of process flow 800C depicted in FIG. 8C. In another embodiment, remote programming instructions may be provided to the patient's IMD via the remote therapy session only after verifying that remote care therapy programming with the patient's IMD is compliant with regulatory requirements of one or more applicable local, regional, national, supranational governmental bodies, non-governmental agencies, and international health organizations, as set forth at block 842 of process flow depicted in FIG. 8D. In a still further variation, various levels of remote control of a patient's controller and its hardware by a clinician controller device may be provided. For example, suitable GUI controls may be provided at the clinician controller device for remotely controlling a camera component or an auxiliary AV device associated with the patient controller device by interacting with a display of the patient's image on the screen of the clinician controller device, e.g., by pinching, swiping, etc., to pan to and/or zoom on different parts of the patient in order to obtain high resolution images, as set forth at block 852 of process flow 800E depicted in FIG. 8E. Additional details regarding some of the foregoing variations will be set forth below for purposes of further embodiments of the present disclosure.

Figure 13:
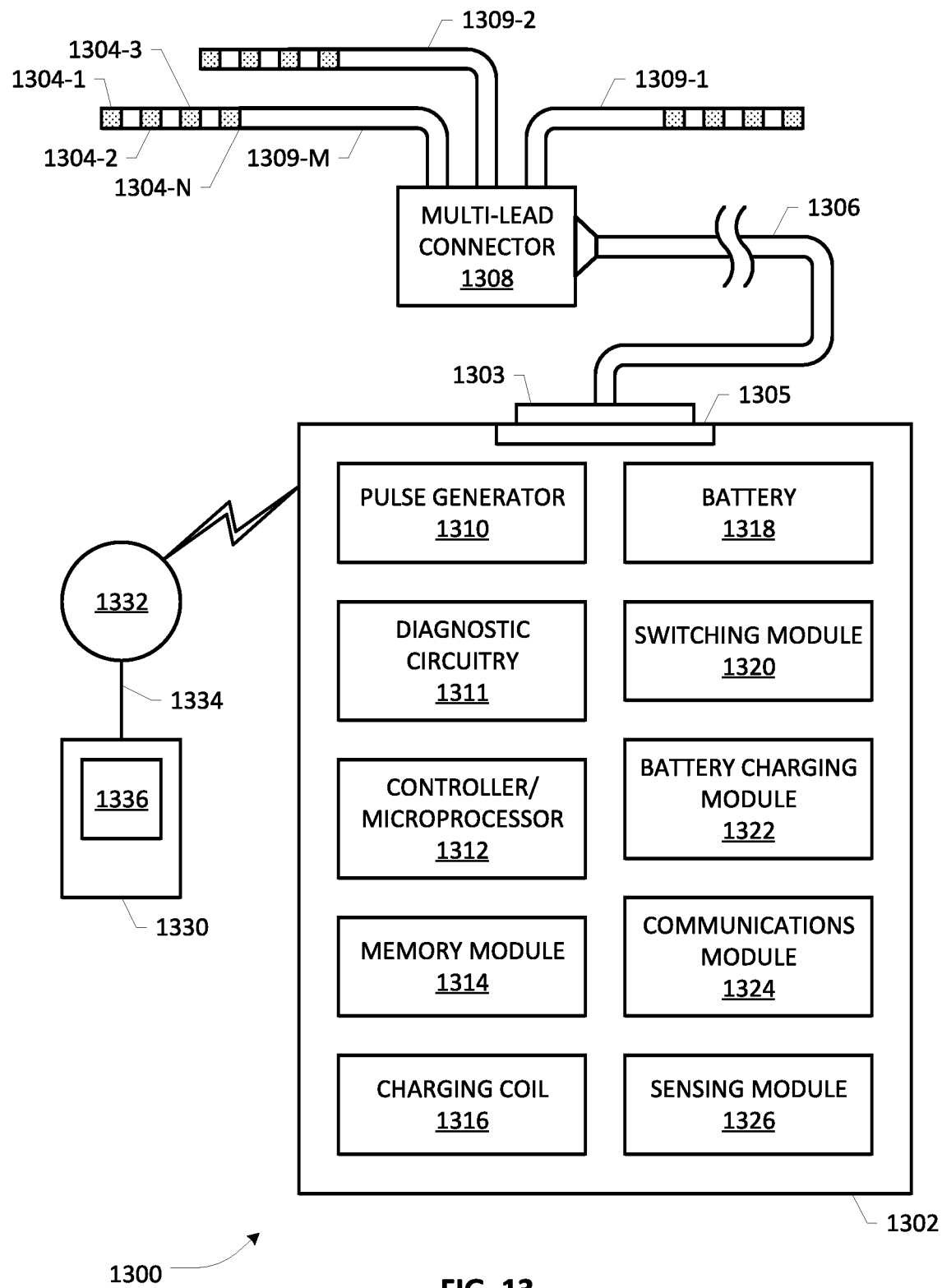
FIG. 13 depicts a block diagram of an IMD and associated system that may be configured for facilitating a remote care therapy application for purposes of an example embodiment of the present disclosure.

Turning to FIG. 13, depicted therein is a block diagram of a therapy system 1300 having an IMD 1302 that may be configured for a remote therapy application for purposes of an example embodiment of the present disclosure. In general, therapy system 100 may be adapted to stimulate spinal cord tissue, peripheral nerve tissue, deep brain tissue, DRG tissue, cortical tissue, cardiac tissue, digestive tissue, pelvic floor tissue, or any other suitable biological tissue of interest within a patient's body, as previously noted. IMD 1302 may include a diagnostic circuit module 1311 adapted to effectuate various diagnostics with respect to the state/condition of one or more stimulation electrodes and sensing electrodes of an implantable lead system as well as other bio/physiological sensors integrated or otherwise operative with IMD 1302. In one example embodiment, IMD 1302 may be implemented as having a metallic housing or can that encloses a controller/processing block or module 1312, pulse generating circuitry 1310, a charging coil 1316, a power supply or battery 1318, a far-field and/or near field communication block or module 1324, battery charging circuitry 1322, switching circuitry 1320, sensing circuitry 1326, a memory module 1314, and the like. Controller/processor module 1312 typically includes a microcontroller or other suitable processor for controlling the various other components of IMD 1302. Software/firmware code may be stored in memory 1314 of IMD 102, which may be integrated with the controller/processor module 1312, and/or other suitable application-specific storage components (not particularly shown in this FIG.) for execution by the microcontroller or processor 1312 and/or other programmable logic blocks to control the various components of the device for purposes of an embodiment of the present patent disclosure.

In one arrangement, IMD 1302 may be configured to couple to one or more stimulation leads 1309-1 to 1309-M using an implantable multi-lead connector 1308 operative to receive corresponding stimulation leads 1309-1 to 1309-M at their respective proximal ends for securely engaging and providing electrical connectivity with respect to each stimulation lead's distal end having a plurality of stimulation electrodes. By way of illustration, stimulation lead 1309-M is exemplified with stimulation electrodes 1304-1 to 1304-N, which may be implanted near or adjacent to the patient's target tissue. Stimulation leads 1309-1 to 1309-M may comprise percutaneous leads, paddle leads, etc., wherein the electrodes may comprise ring electrodes, segmented or split electrodes, planar electrodes, and the like. Preferably, a single lead cable 1306 may be provided for electrically connecting the multi-lead connector 1308 to IPG 102 via a suitable connector interface or socket 1303 that may be mated to an interface receptacle or header portion 1305 of IMD 1302. In general, electrical pulses are generated by the pulse generating circuitry 1310 under the control of processing block 1312, and are provided to the switching circuitry 1320 that is operative to selectively connect to electrical outputs of IMD 1302, wherein one or more stimulation leads 1309-1 to 1309-M and/or one more stimulation electrodes 1304-1 to 1304-N per each lead may be energized according to a therapy protocol, e.g., by the patient (via a local session) and/or a clinician (via a local or remote session) using a corresponding external device, e.g., device 1330. Further, external device 1330 may also be configured to charge/recharge the battery 1318 of IMD 1302 (although a separate recharging device could alternatively be employed), in addition to accessing memory 1314, and/or (re)programming IMD 1302 with respect to the stimulation set parameters including pulsing specifications while implanted within the patient. In alternative embodiments, however, separate programmer devices may be employed for charging and/or programming the IMD 1302 device and/or any programmable components thereof. A connector or "wand" 1334 may be electrically coupled to the external device 1330 through suitable electrical connectors (not specifically shown), which may be electrically connected to a telemetry component 1332 (e.g., inductor coil, RF transceiver, etc.) at the distal end of wand 1334 through respective communication links that allow bi-directional communication with IMD 1302 in a local session scenario. Optionally, in some embodiments, the wand 1334 may comprise one or more temperature sensors for use during charging operations.

In an example scenario, a user (e.g., a doctor, a medical technician, or the patient) may initially communicate with IPG 1302 by placing the wand 1334 proximate to the IMD 1302. Preferably, the placement of the wand 1334 allows the telemetry system to be aligned with the far-field and/or near field communication circuitry 1324 of IMD 1302 for facilitating bonding operations, programming operations, and the like. The external device 1330 preferably provides one or more user interfaces 1336 (e.g., touch screen, keyboard, mouse, buttons, scroll wheels or rollers, or the like), allowing the user to operate IMD 1302. The external device 1330 may be controlled by the user through the user interface 1336, allowing the user to interact with IMD 102, including, e.g., effectuating programmatic control for facilitating diagnostic measurements, dynamically configuring electrodes for different therapy schemes, etc. Further, the user interface 1336 may permit the user to move electrical stimulation along and/or across one or more of the leads 1309-1 to 1309-M using different lead electrode combinations selected from electrodes, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME", which is incorporated herein by reference. Optionally, the user interface 1336 may permit the user to designate which electrodes 1304-1 to 1304-N of a particular lead are to stimulate (e.g., emit current pulses, in an anode state, in a cathode state), or not selected to stimulate (i.e., remain inactive or floating, i.e., "unused"), with respect to a potential stimulation target, to measure/sense tissue electrical parameters, or the like. As used herein "stimulation" refers to the application of an electrical signal to a target body tissue, regardless of the effect that signal is intended to produce. Additionally or alternatively, the external device 1330 may access or download the electrical measurements from the memory 1314 acquired by the sensing circuitry 1326.

In some implementations, the external device 1330 may permit operation of IMD 1302 according to one or more SCS programs or therapy applications to treat the patient. Each SCS program may include one or more sets of stimulation parameters of the pulse including pulse amplitude, stimulation level, pulse width, pulse frequency or inter-pulse period, pulse repetition parameter (e.g., number of times for a given pulse to be repeated for respective stimulation sets or stimsets during execution of program), biphasic pulses, monophasic pulses, etc. IMD 1302 modifies its internal parameters in response to the control signals from the external device 1330 to vary the stimulation characteristics of the stimulation therapy transmitted through the lead system 1309-1 to 1309-M to the tissue of the patient. Example neurostimulation (NS) systems, stimsets, and multi-stimset programs are set forth in U.S. Pat. No. 7,228,179, entitled "METHOD AND APPARATUS FOR PROVIDING COMPLEX TISSUE STIMULATION PATTERNS", and International Patent Publication Number WO 2001/093953, entitled "NEUROMODULATION THERAPY SYSTEM", which are incorporated hereinabove by reference.

Skilled artisans will recognize that at least some functionalities and components of IMD 1302 and at least some functionalities and components of device 1000 of FIG. 10 may be combined for purposes of an example embodiment involving remote care therapy. Likewise, at least some functionalities and components of device 1330 may be combined with at least some functionalities and components of device 1100 of FIG. 11 in an embodiment involving remote care therapy. Accordingly, various types of therapy operations exemplified above may be effectuated by a clinician via a secure remote session involving the clinician's device 1330, patient's device (not shown in this FIG.) and the patient's IPG/IMD 1302 according to example embodiments of the present disclosure, which in some use case scenarios may involve one or more message/work flows and processes set forth previously in the present patent application.

Figure 14:
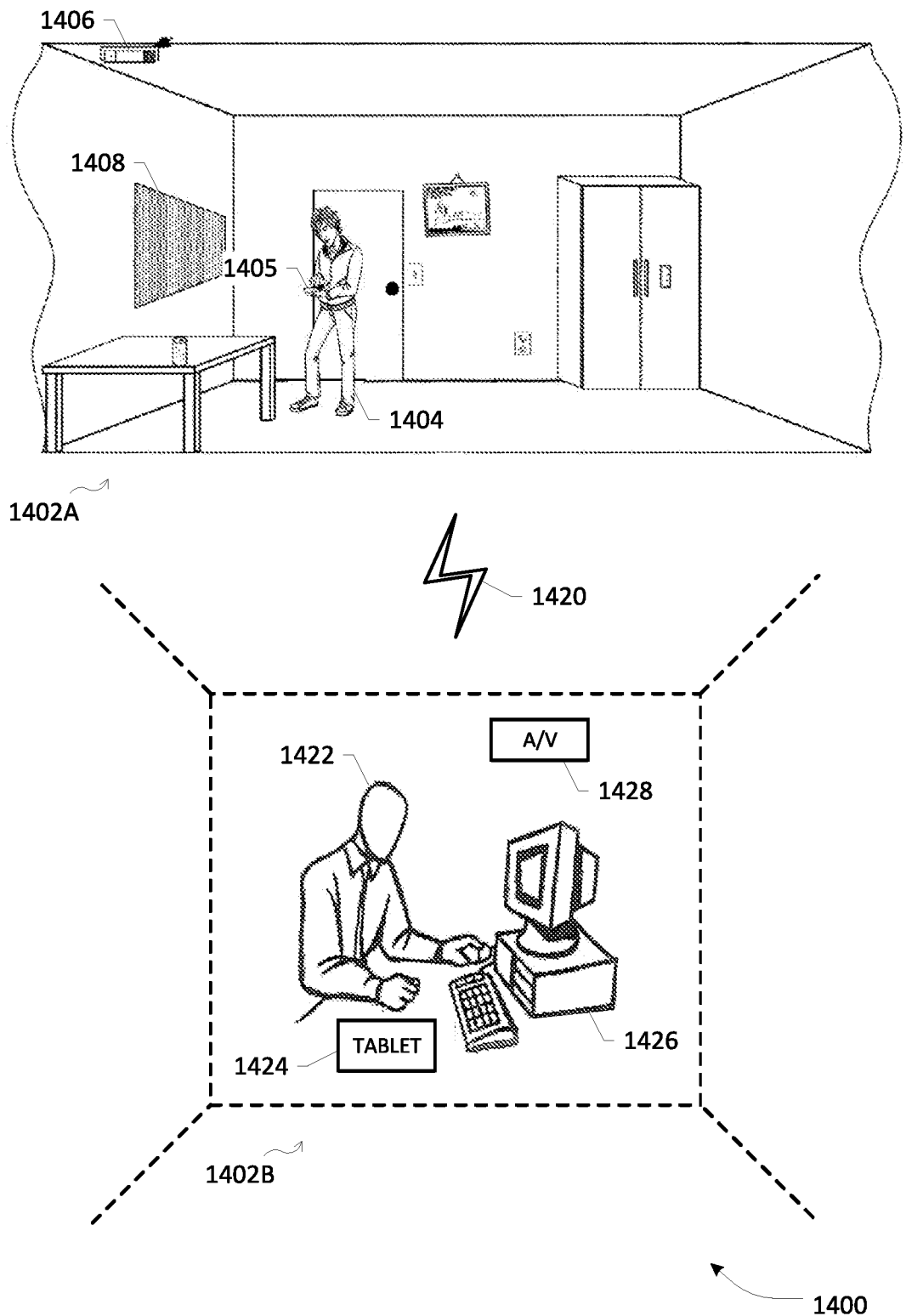
FIG. 14 depicts example patient and clinician environments, each having respective controller devices and optional auxiliary AV equipment for purposes of an embodiment of the present disclosure.

FIG. 14 depicts an example remote care environment 1400 comprising patient and clinician environments 1402A, 1402B, respectively, wherein one or more example embodiments of the present disclosure may be practiced. By way of illustration, patient and clinician environments 1402A, 1402B are exemplified as rooms, each having respective controller devices and optional auxiliary AV equipment, although different environments with respect to the locations of patient 1404 and 1422 are also possible within the ambit of certain embodiments herein. Patient 1404 located in environment 1402A may use a patient controller 1405 in association with monitor 1408 and auxiliary AV equipment 1406 for engaging in a remote care session with clinician 1422 via a suitable communication link 1420. Clinician 1422 located in environment 1402B may use a clinician programmer 1424 in association with medical/computer equipment 1426 and auxiliary AV equipment 1428 disposed therein.

Figure 15:
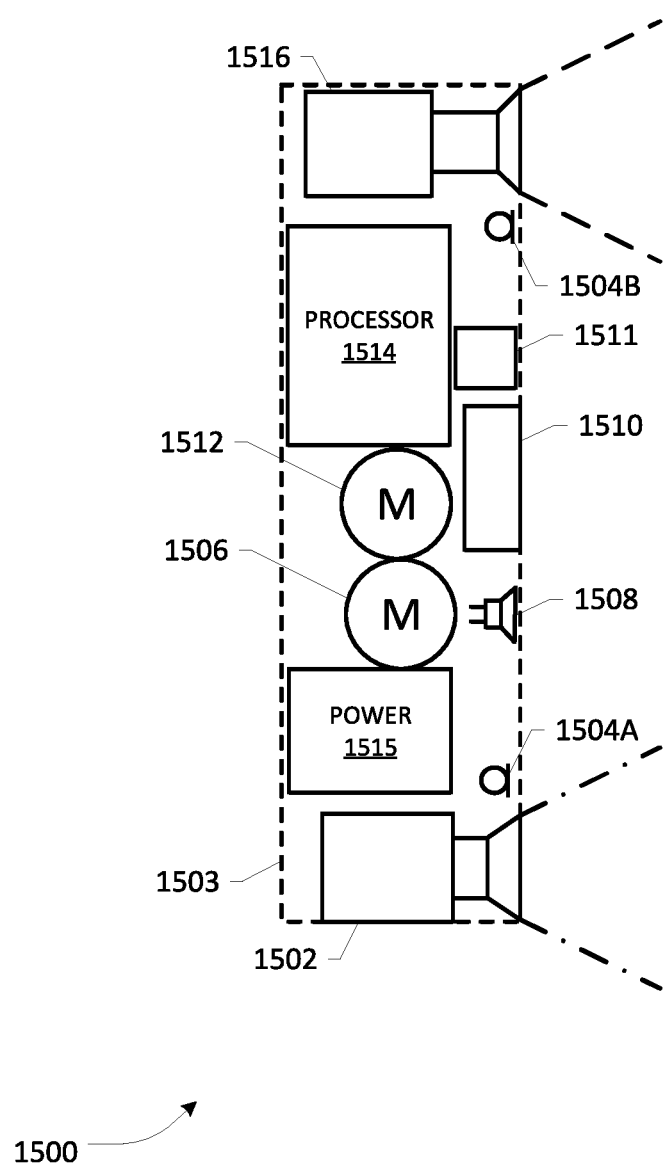
FIG. 15 is a block diagram of an optional AV device operative with a clinician controller device and/or a patient controller device for purposes of an embodiment of the present disclosure.

FIG. 15 is a block diagram of an optional AV device 1500 operative with a clinician controller device and/or a patient controller device for purposes of an embodiment of the present disclosure. In some arrangements, AV device 1500 may be configured to scan at least a portion of an environment, e.g., environments 1402A/1402B and any objects therein. In some arrangements, AV device 1500 may also be configured to provide MR/VR/AR output, such as images, sounds, overlays, and the like, with respect to a remote care session established between a patient and a clinician. A chassis 1503 may contain a number of AV-related components, range-finding components, object recognition components, presence detectors, etc. For example, camera 1502, projector 1516, microphones 1504A/B and speaker 1508 may provide auxiliary AV functionality with respect to an ongoing remote care session. Range finder 1510 and other transducers 1511 may also be provided to determine where, or if, a user (i.e., a patient or a clinician) is positioned within the user's environment and/or with respect to the objects within the environment. Actuators may be provided to displace or move the chassis 1503 or components therein such as the projector 1516 and/or the camera 1502 in different directions in a 3D coordinate system. For example, a pan motor 1512 and a tilt motor 1506 may be provided (e.g., powered by power supply 1515) to scan different portions of the user environment at different levels of granularity such that different parts of a patient's body may be focused. Likewise, zoom control provided with the camera 1502 may be actuated to zoom in on a particular part or parts of the patient that may be of interest to the clinician. A computing device and associated AV signal processing circuitry 1514 may be provided to control the overall functionality of AV equipment 1500 operative in response to user input provided via appropriate GUI controls of the patient controller device and/or the clinician programmer device with respect to the AV communications of a remote care session in some example embodiments.

Figure 16B:
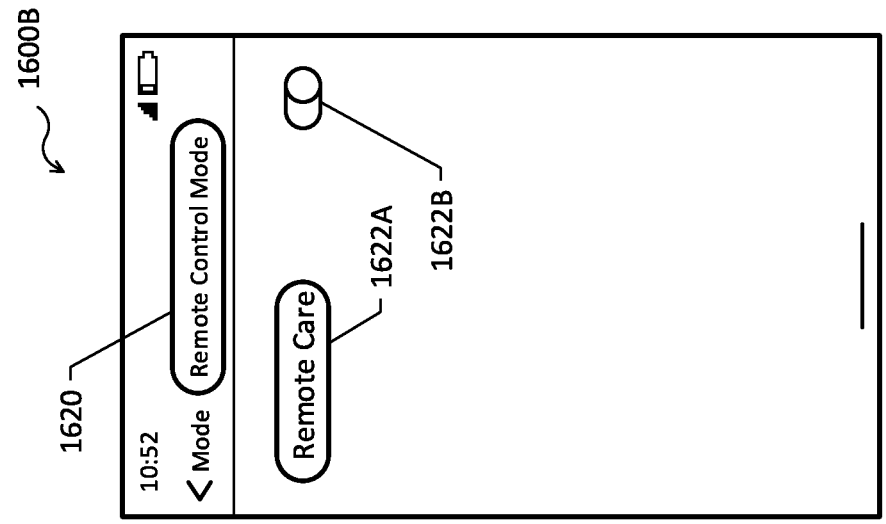
FIGS. 16A-16C depict representations of an example user interface and associated dialog boxes provided with a patient controller device for selecting different therapy service modes and for facilitating controls with respect to an AV communication session and a remote therapy session in an integrated remote care service application for purposes of an embodiment of the present disclosure.
Figure 16A:
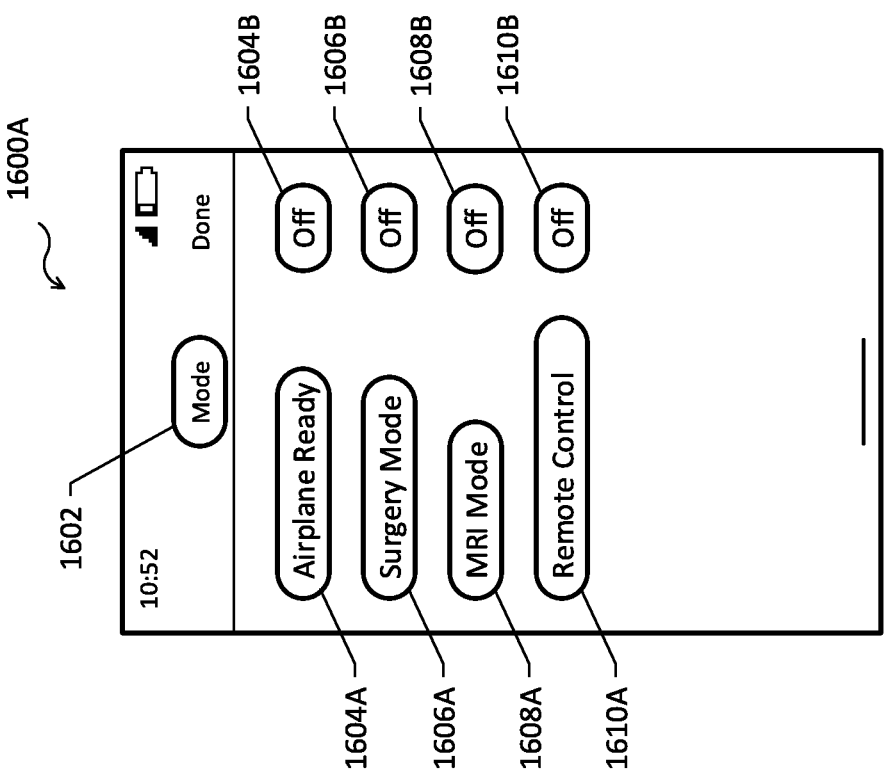
Figure 16C:
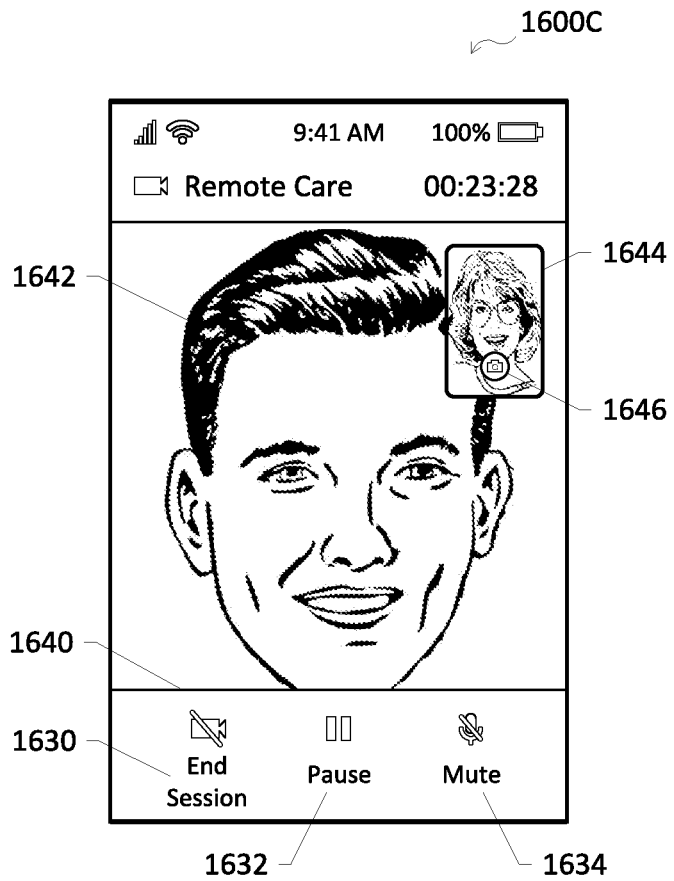

FIGS. 16A-16C depict representations of an example user interface and associated dialog boxes or windows provided with a patient controller device, e.g., as a touch screen display of device 150, for selecting different therapy service modes and for facilitating controls with respect to an AV communication session and a remote therapy session as part of an integrated remote care service application for purposes of an embodiment of the present disclosure. In some example implementations, a patient controller device may be provided with one or more non-transitory tangible computer-readable media or modules having program code stored thereon for execution on the patient controller device as part of or in association with a patient controller application for facilitating remote therapy and telehealth delivery in an integrated session having a common application interface. A code portion may be provided for displaying a mode selector icon on a GUI display screen of the patient controller device, wherein the mode selector icon is operative for accepting input by the patient to launch a remote care session with a clinician having a clinician programmer device. A code portion may be provided for displaying one or more audio controls and one or more video controls for facilitating an AV communication session or channel associated with the remote care session after the remote care session is established between the patient controller device and the clinician controller device. Such AV controls may be represented as suitable icons, pictograms, and the like, e.g., a video/camera icon for controlling a video channel, a microphone icon for controlling an audio channel, a speaker icon for volume control, as well as control icons operative with respect to picture-in-picture (PIP) display regions, and the like. For example, video controls may be operative to effectuate a first display window and a second display window on the GUI display for respectively presenting an image of the clinician and an image of the patient in a PIP display mode. Yet another code portion may be provided for displaying one or more remote care therapy session controls in an overlay panel presented on the GUI display, wherein the one or more remote care therapy session controls are operative with respect to starting and ending a remote care therapy session by the patient as well as facilitating a temporary intervention or interruption of the therapy session while the AV communication session is maintained. As noted above, an example remote care therapy session may involve providing one or more programming instructions to the patient's IMD as part of the remote care session, and temporary intervention of the remote therapy may only suspend the remote programming of the patient's IMD although the AV communication session between the patient and the clinician remains active. In further embodiments, one or more code portions may be provided with the patient controller application to effectuate tactile controls with respect to different portions, fields, regions or X-Y coordinates of an active GUI display window that may be configured to interact with the functionality of the AV controls and/or therapy session controls. In still further embodiments, one or more code portions may be provided with the patient controller application to effectuate one or more data labeling buttons, icons, pictograms, etc., as part of the GUI display of the patient controller device, wherein the one or more data labeling buttons are operative to accept input by the patient corresponding to a subjective characterization of audio and/or video quality of the AV communications and/or other aspects of the therapy by the patient during the remote care session.

As illustrated, FIGS. 16A and 16B depict example GUI screens 1600A and 1600B of a patient controller device that allow user input with respect to various mode settings, including the activation and deactivation of allowing a remote control programming (i.e., therapy) session to be conducted. GUI screen 1600A includes a mode selector 1602 that may be activated to show various mode settings which in turn may be selected, enabled or otherwise activated by using associated tactile controls. For example, modes such as "Airplane Ready" 1604A, "Surgery Mode" 1606A, "MRI Mode" 1608A, "Remote Control Mode" 1610A, each having a corresponding swipe button 1604B-1610B are depicted. GUI screen 1600B illustrates a display that may be effectuated upon selecting or allowing Remote Control 1620 wherein a Remote Care Mode 1622A may be selected or enabled for activating remote therapy using a corresponding swipe button 1622B. A patient may therefore selectively permit the activation of remote therapy (i.e., remote programming of the IMD), whereby if activated and connected, a clinician can securely change or modify the therapy settings of the patient's IMD by effectuating appropriate therapy setting controls and associated GUIs provided at a controller device as will be set forth below.

FIG. 16C depicts an example GUI display screen 1600C of the patient controller device during a remote care session, wherein an image of the clinician 1642 and an image of the patient 1644 may be presented in a PIP display region. In one display mode, the patient's image 1644 may be presented as a smaller offset or overlay image and the clinician's image 1642 may be presented as a main, larger image. In some embodiments, the patient image window 1644 may be moved around the UI screen by "dragging" the image around the viewing area of the clinician image window 1642. An image swap control 1646 may be provided to swap the PIP display regions in another display mode, whereby the patient's image 1644 may be presented as the main, larger image whereas the clinician's image 1642 may be presented in a smaller overlay window.

In some embodiments, a control panel 1640 may also be presented as part of the GUI screen 1600C, wherein various AV communication session controls and remote therapy session controls may be displayed as suitable icons, pictograms, etc., in a consolidated GUI display as noted above. A video session icon 1630 may be activated/enabled or deactivated/disabled to selectively turn on or off the video channel of the session. A microphone icon 1634 may be activated/enabled or deactivated/disabled to selectively turn on or off the audio channel of the session. A pause/resume icon 1632 may be activated/enabled or deactivated/disabled to selectively pause or suspend, or resume the remote therapy session involving remote programming of the patient's IMD. In some implementations, activating or deactivating the video session icon 1630 may also be configured to turn on or off the remote therapy session. In some implementations, separate remote therapy session controls (e.g., start control, end control, etc. in addition to pause and resume controls) may be provided that are operative independent of the AV communication session controls. Still further, data labeling buttons may also be provided in a separate overlay or window of the GUI screen 1600C (not shown in this FIG.) to allow or otherwise enable the patent to input a subjective characterization of the AV data and therapy experience data as noted previously.

Figure 17B:
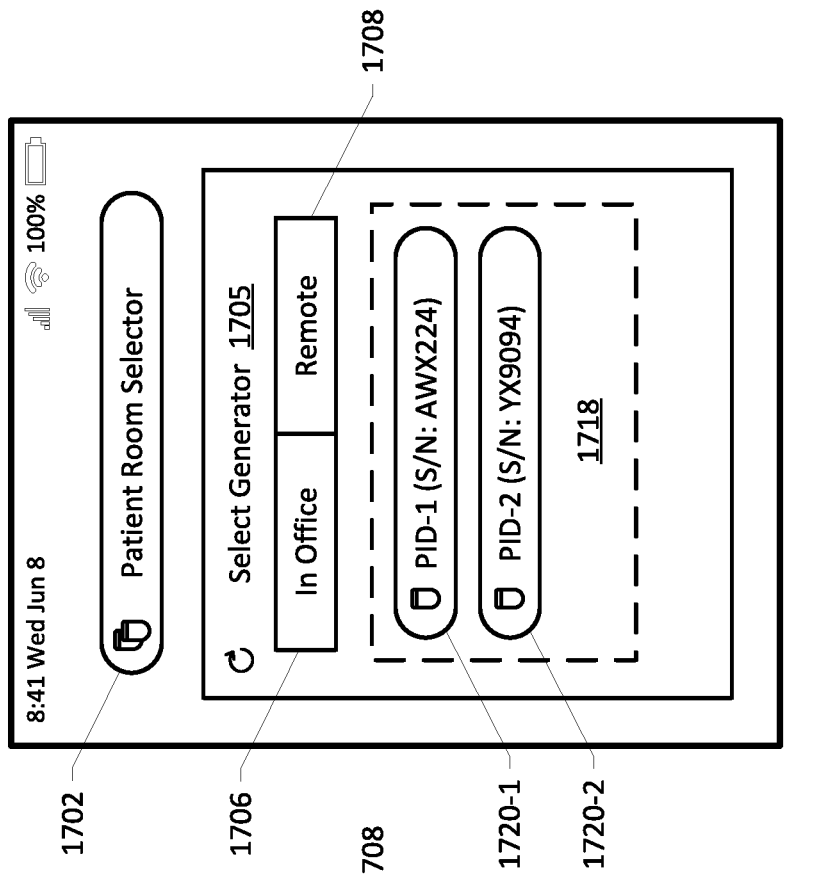
FIGS. 17A and 17B depict representations of an example user interface and associated dialog boxes provided with a clinician controller device for selecting different therapy service modes for purposes of an embodiment of the present disclosure.
Figure 17A:
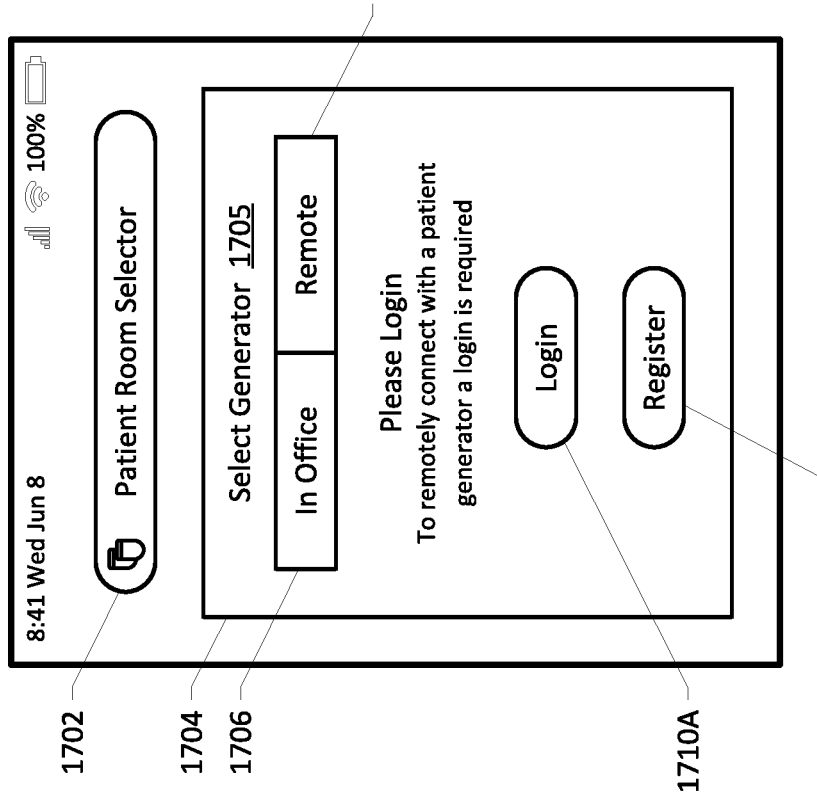

FIGS. 17A and 17B depict representations of an example user interface and associated dialog boxes or windows provided with a clinician controller/programmer device, e.g., as a touch screen display of device 180, for selecting different therapy service modes and for effectuating remote therapy operations in an integrated remote care service application according to some example embodiments of the present disclosure. Preferably, the GUI of the clinician device may be optimized or resized to provide a maximum display window for the presentation of a patient's image during remote therapy while allowing the presentation of appropriate remote care therapy session and setting controls as well as AV communication session controls such that high quality video/image information may be advantageously obtained by the clinician, which can help better evaluate the patient's response(s) to the applied/modified therapy settings and/or the clinician's verbal, textual, and/or visual requests to perform certain tasks as part of remote monitoring. Accordingly, in some example embodiments, the clinician device may be provided with one or more non-transitory tangible computer-readable media or modules having program code stored thereon for execution on the clinician device as part of or in association with a clinician controller application for facilitating remote therapy and telehealth delivery in an integrated session having a common application interface that effectuates an optimized GUI display within the form factor constraints of the device. In one arrangement, a code portion may be provided for displaying a virtual waiting room identifying one or more patients, each having at least one IMD configured to facilitate a therapy, wherein the virtual waiting room is operative to accept input by the clinician to select a patient to engage in a remote care session with a patient controller device of the selected patient. A code portion may be provided for displaying one or more audio controls and one or more video controls for facilitating an AV communication session associated with the remote care session after the remote care session is established between the patient controller device and the clinician programmer device. Roughly similar to the GUI presentation at a patient controller device, various AV session controls may be represented as suitable icons, pictograms, etc. as part of a GUI display of the at the clinician programmer device. Further, example video controls may be configured to effectuate a first display window (i.e., a clinician image window) and a second display window (i.e., a patient image window) on the GUI display for respectively presenting an image of the clinician and an image of the patient. A code portion may be provided for displaying one or more remote care therapy session and setting controls, wherein the one or more remote care therapy setting controls are operative to facilitate one or more adjustments with respect to the patient's IMD settings in order to provide appropriate therapy to the patient as part of a remote therapy component of the remote care session. Preferably, the code portion may be configured to provide the AV communication session controls as well as the remote care therapy session and setting controls in a consolidated manner so as to facilitate the display thereof in a minimized overlay panel presented on the GUI screen while maximizing the second display window such that an enlarged presentation of the patient's image is effectuated during the remote care session. In some embodiments, the remote care therapy setting controls may be configured to expand into additional graphical controls for further refining one or more IMD settings depending on the implementation and/or type(s) of therapy applications the clinician programmer device is configured with. For example, such remote care therapy setting controls may comprise icons or pictograms corresponding to, without limitation, one or more of a pulse amplitude setting control, a pulse width setting control, a pulse frequency setting control, a pulse firing delay control, a pulse repetition parameter setting control, a biphasic pulse selection control, a monophasic pulse section control, a tonic stimulation selection control, a bust stimulation selection control, a lead selection control, an electrode selection control, and a "Stop Stimulation" control, etc., at least some of which may be presented in a set of hierarchical or nested pull-down menus or display windows. In still further embodiments, a code portion may be provided for displaying one or more data labeling buttons as part of the GUI display of the clinician programmer device, similar to the GUI embodiments of the patient controller device described above, wherein the one or more data labeling buttons are operative to accept input by the clinician corresponding to a subjective characterization of AV quality, therapy response capture, and other aspects of therapy programming during the remote care session.

GUI screen 1700A depicted in FIG. 17A is representative of a "login" screen that may be presented at the clinician device upon launching the clinician controller application for facilitating a clinician to select a service mode, e.g., a remote care service mode or an in-office care service mode. A "Patient Room" selector menu option 1702 may be operative to present a "generator" window 1705 that includes an "In-Office" patient option 1706 or a "Remote" patient option 1708, wherein the activation or selection of the Remote patient option 1708 effectuates one or more windows or dialog boxes for facilitating user login, registration, authentication/authorization and other security credentialing services, as exemplified by windows 1710A, 1710B. Upon validation, the clinician may be presented with a virtual waiting room 1718 identifying one or more remote patients as exemplified in GUI screen 1700B of FIG. 17B. Each remote patient may be identified by one or more identifiers and/or indicia, including, without limitation, personal identifiers, respective IMD identifiers, therapy identifiers, etc., subject to applicable privacy and healthcare laws, statutes, regulations, and the like. Accordingly, in some embodiments such identification indicia may comprise, inter alia, patient names, images, thumbnail photos, IMD serial numbers, etc., collectively referred to as Patient ID (PID) information, as illustrated by PID-1 1720-1 and PID-2 1720-2. In some embodiments, a time indicator may be associated with each remote patient, indicating how long a remote patient has been "waiting" (e.g., the time elapsed since launching a remote care session from his/her controller device). In some embodiments, a priority indicator may also be associated with remote patients, wherein different priorities may be assigned by an intervening human and/or AI/ML-based digital agent. Furthermore, patients may have different types of IMDs to effectuate different therapies and a patient may have more than one IMD in some cases. An example embodiment of virtual waiting room 1718 may therefore include a display of any combination of remote patients and their respective IMDs by way of suitably distinguishable PIDs having various pieces of information, wherein the PIDs may be individually selectable by the clinician for establishing a remote care session that may include remote therapy programming or just telehealth consultations.

Figure 18A:
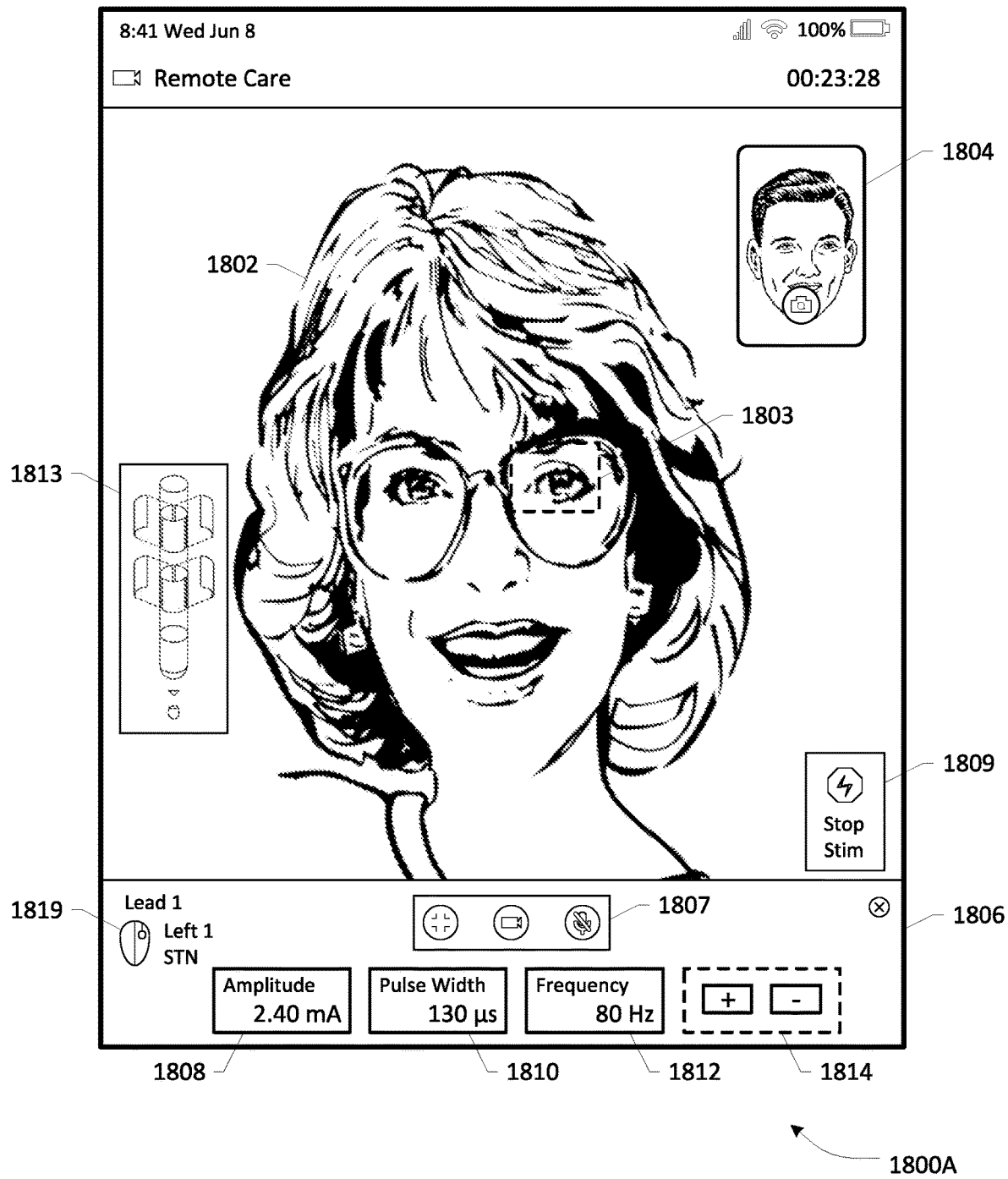
FIGS. 18A and 18B depict representations of an example user interface provided with a clinician controller device for facilitating controls with respect to an AV communication session and a remote therapy session in an integrated remote care service application for purposes of an embodiment of the present disclosure.
Figure 18B:
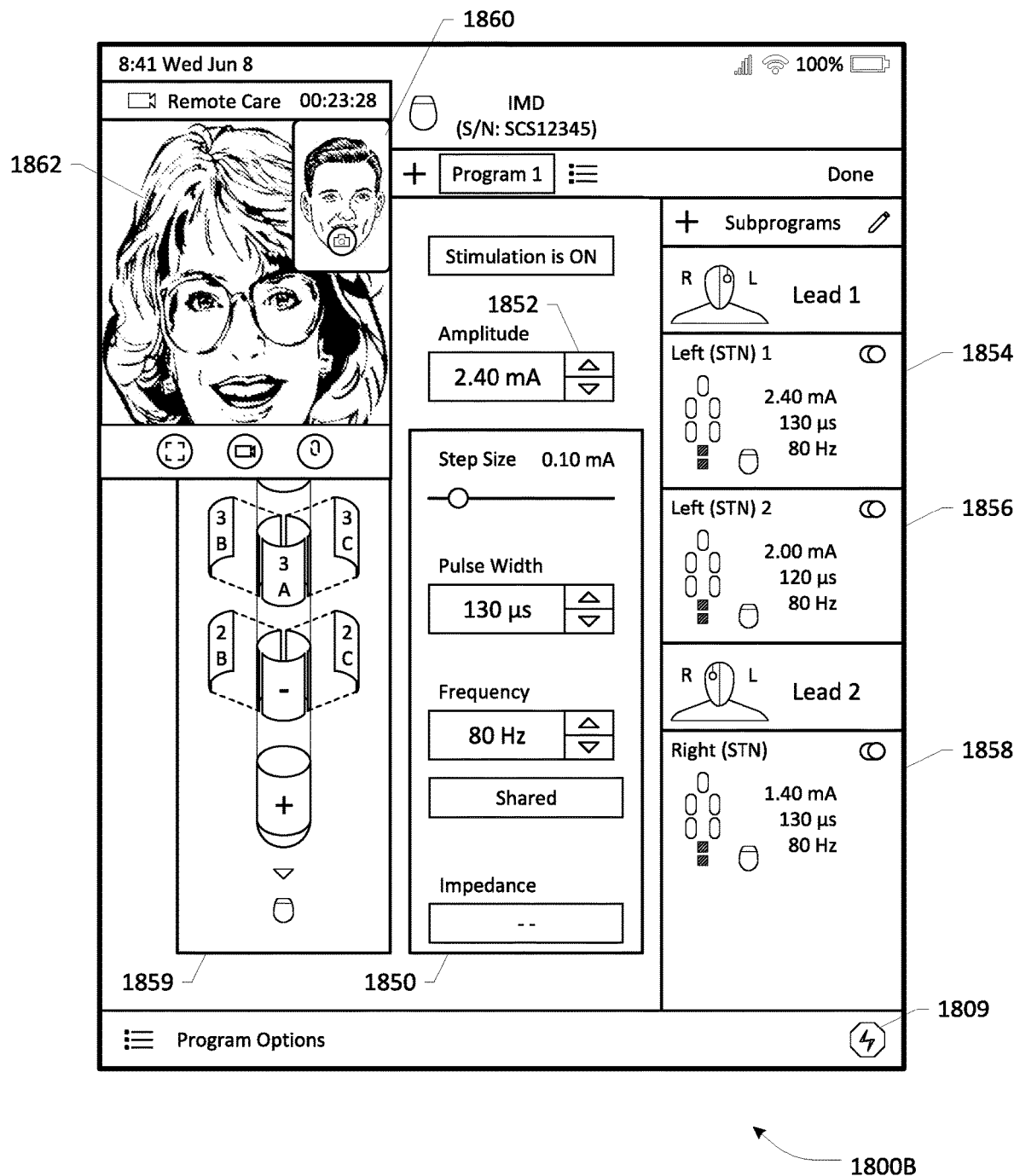
Figure 19A:
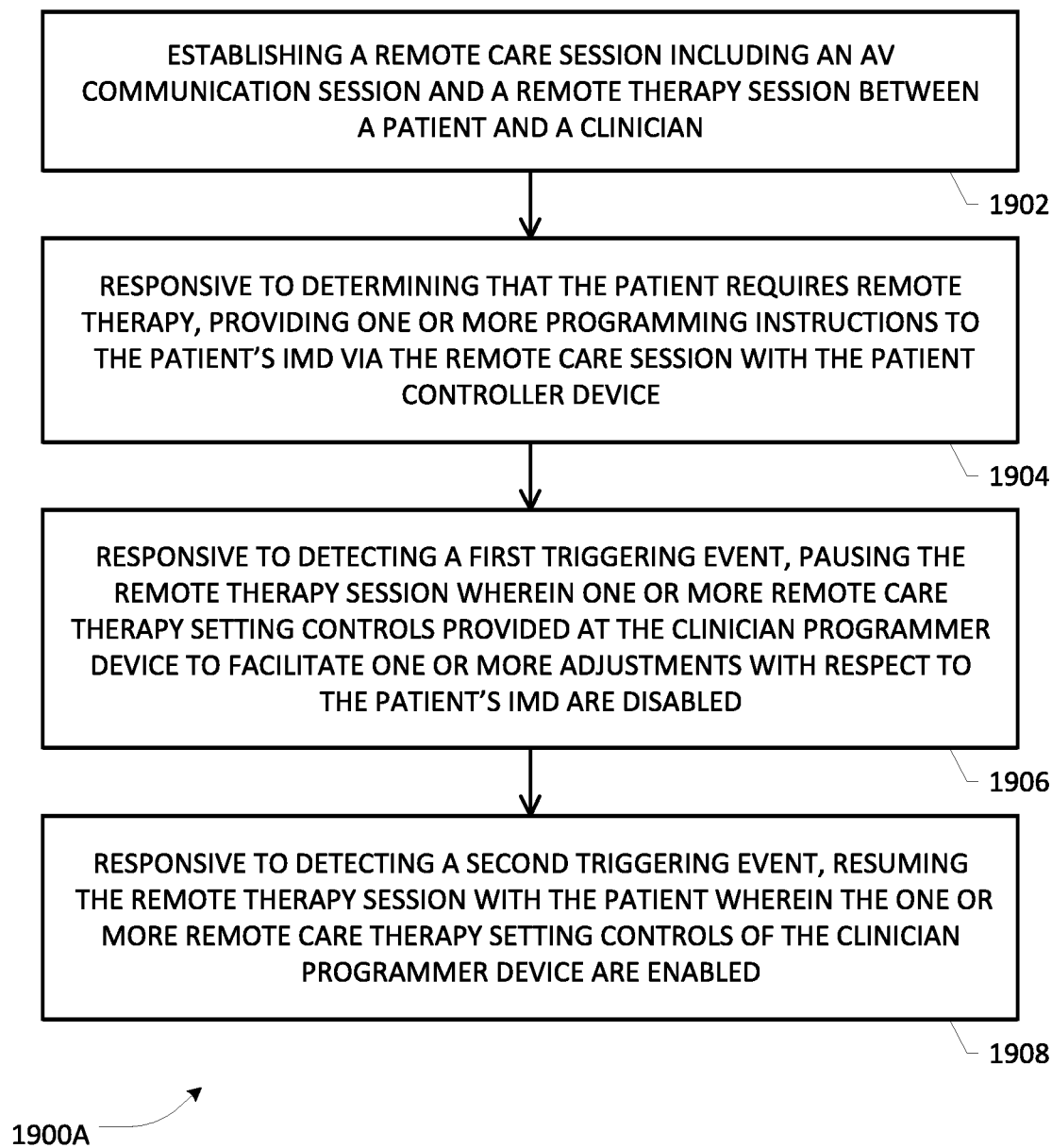

FIGS. 18A and 18B depict representations of an example user interface provided with a clinician controller device for facilitating controls with respect to an AV communication session and a remote therapy session in an integrated remote care service application for purposes of an embodiment of the present disclosure. As illustrated, GUI screen 1800A depicted in FIG. 18A is representative of a display screen that may be presented at the clinician device after establishing that remote therapy programming is to be effectuated for a selected remote patient. In accordance with the embodiments set forth herein, GUI screen 1800A is arranged so that the patient's video image is presented in an optimized or resized/oversized display window 1802 while the clinician's video image is presented in a smaller display window 1804 along with a compact control icon panel 1806 to maximize the level of detail/resolution obtained in the patient's image. Furthermore, the smaller clinician image window 1804 may be moved around the UI screen by "dragging" the image around the viewing area of the patient's image window 1802 to allow more control of the positioning of the display windows so that the patient's image view is unimpeded and/or optimized at a highest possible resolution. It will be appreciated that such high level video quality is particularly advantageous in obtaining more reliable cues with respect to the patient's facial expressions, moods, gestures, eye/iris movements, lip movements, hand movements tremors, jerks, twitches, spasms, contractions, or gait, etc., that may be useful in diagnosing various types of motor/neurological disorders, e.g., Parkinson's disease.

Control panel window 1806 may include a subpanel of icons for AV and/or remote care session controls, e.g., as exemplified by sub-panel 1807 in addition to a plurality of icons representing remote therapy setting controls, e.g., pulse amplitude control 1808, pulse width control 1810, pulse frequency control 1812, increment/decrement control 1814 that may be used in conjunction with one or more therapy setting controls, along with a lead selection indication icon 1819. Skilled artisans will recognize that the exact manner in which a control panel window may be arranged as part of a consolidated GUI display depends on the therapy application, IMD deployment (e.g., the number of leads, electrodes per lead, electrode configuration, etc.), and the like, as well as the particular therapy settings. Additional control icons relating to stimulation session control, e.g., Stop Stimulation icon 1809, as well as any other icons relating to the remote care session such as lead/electrode selection 1813, may be presented as minimized subpanels adjacent to the control panel window 1806 so as not to compromise the display area associated with the patient' image display 1802.

In some embodiments, a code portion may be provided as part of the clinician controller application to effectuate a transitioning of the resized display GUI screen 1800A to or from a more expanded, icon-rich GUI screen 1800B in a different display mode as illustrated in FIG. 18B. For example, GUI screen 1800B may be configured such that the clinician's and patient's video images are presented in smaller windows 1860, 1862, with most of the rest of the display region being populated by various icons, windows, pull-down menus, dialog boxes, etc., for presenting available programming options, lead selection options, therapy setting options, electrode selection options, and the like, as represented by panels 1850-1859. In some embodiments, the video UI panels and related controls associated with clinician/patient video image windows 1860/1862 may be moved around the GUI screen 1800B by "dragging" the images around the display area. Still further, the positioning of the video UI panels and related controls associated with clinician/patient video image windows 1860/1862 may be stored as a user preference for a future UI setup or configuration that can be instantiated or initialized when the controller application is launched. Regardless of the exact implementation, however, the rest of the GUI screen 1800B may be populated with each of the individual therapy settings such as the amplitude, pulse width, and frequency of the stimulation signal can be adjusted, in addition to effectuating the selection of a particular implanted lead (e.g., Lead 1, Lead 2) as well as the corresponding configuration of the selected lead (i.e., the selection and polarity of the electrodes of each implanted lead being used during stimulation. As can be appreciated, it is contemplated that a clinician device may be configured to utilize either of the programming GUI screens 1800A, 1800B. Additionally, the clinician device may be programmed to be able to toggle between the two GUI embodiments by pressing or otherwise activating zoom/collapse buttons that may be provided on respective screens.

In some further embodiments, a clinician device may be provided with additional functionality when utilizing or operating in the resized display GUI screen 1800A mode. By way of a suitable inputting mechanism at the clinician device, e.g., by pressing or double-tapping a particular portion of the patient's image, or by scrolling a cursor or a pointing device to a particular portion of the patient's image, etc., the clinician can remotely control the AV functionality of the patient controller device, e.g., a built-in camera or an auxiliary AV device such as AV equipment 1500, to zoom in on and/or pan to specific portions of the patient's body in order to obtain close-up images that can enable better diagnostic assessment by the clinician. In such embodiments, zooming or enlarging of a portion of the patient's image, e.g., eye portion 1803, may be effectuated by either actual zooming, i.e., physical/optical zooming of the camera hardware, or by way of digital zooming (i.e., by way of image processing).

In some embodiments, both optical and digital zooming of a patient's image may be employed. In still further embodiments, the patient controller device and/or associated AV equipment may be panned and/or tilted to different portions of the patient's body to observe various motor responses and/or conditions while different programming settings may be effectuated in a remote therapy session, e.g., shaking and tremors, slowed movement or bradykinesia, balance difficulties and eventual problems standing up, stiffness in limbs, shuffling when walking, dragging one or both feet when walking, having little or no facial expressions, drooling, muscle freezing, difficulty with tasks that are repetitive in nature (like tapping fingers or clapping hands or writing), difficulty in performing everyday activities like buttoning clothes, brushing teeth, styling hair, etc.

In still further embodiments, separate remote therapy session intervention controls (e.g., pause and resume controls) may be provided in addition to stimulation start and termination controls, which may be operative independent of or in conjunction with AV communication session controls, in a manner similar to the patient controller GUI embodiments set forth hereinabove. Still further, data labeling buttons or controls may also be provided in a separate overlay or window of the GUI screens 1800A/B (not shown in FIGS. 18A/B) to allow or otherwise enable the clinician to provide different types of data labels for the AV data and therapy settings data in some additional embodiments described further below.

FIGS. 19A-19D depict flowcharts illustrative of blocks, steps and/or acts that may be (re)combined in one or more arrangements with or without additional flowcharts of the present disclosure for facilitating remote care therapy intervention according to some example embodiments wherein a user-initiated intervention and/or an automated, programmatically controlled intervention may be effectuated. Process flow 1900A of FIG. 19A may commence with establishing a remote care session including an AV communication session/channel and a remote therapy session/channel between a patient and a clinician in a manner similar to some of the embodiments described above (block 1902). At block 1904, a determination may be made, e.g., by the clinician, that the patient requires remote therapy, and responsive thereto, one or more programming instructions may be provided to the patient's IMD via the remote therapy session of the remote care session, which is mediated by way of the patient controller device in a manner similar to some of the embodiments set forth above. At block 1906, responsive to detecting a first triggering event, the remote therapy session may be paused, suspended, or otherwise temporarily ceased, wherein one or more remote care therapy setting controls provided at the clinician programmer device to facilitate one or more adjustments with respect to the patient's IMD may be disabled. At block 1908, responsive to detecting a second triggering event subsequent to the first triggering event, the remote therapy session with the patient may be resumed wherein the one or more remote care therapy setting controls of the clinician programmer device may be enabled. In some embodiments, the clinician may be notified (e.g., by way of a suitable GUI display window) when the patient pauses therapy by activating a pause control (e.g., operative as a first triggering event), wherein all controls except the AV communications may be disabled until the patient resumes therapy by activating a resume control (e.g., operative as a second triggering event). Such pause and resume control may be effectuated using one or more icons presented as part of the patient controller's GUI, e.g., pause/resume 1632, exemplified in FIG. 16C, or by way of voice or gesture commands.

In some additional or alternative embodiments, regardless of how the first and/or second triggering events are caused or effectuated, the AV communication session may also be paused while the remote therapy is in a pause mode due to a triggering event. Subsequently, upon resuming the remote therapy due to the occurrence of a second triggering event, the AV communication session may also be resumed, as set forth at block 1920 of process flow 1900B depicted in FIG. 19B. In one configuration wherein manual intervention is implemented, a first triggering event may be caused or effectuated to pause the remote therapy programming by activating a first one of a plurality of remote therapy session controls provided at the patient controller device or at the clinician programmer device, as set forth at block 1930 of process flow 1900C depicted in FIG. 19C. In similar fashion, a second one of the plurality of remote therapy session controls provided at the patient controller device or at the clinician programmer device may be manually activated to cause a second triggering event (e.g., a resume control) to resume the remote therapy programming, as set forth at block 1940 of process flow 1900D depicted in FIG. 19D. A non-exhaustive list of usage scenarios involving manual intervention from the standpoint of a patient may include, inter alia, the patient needing to answer the door, having to use the bathroom, attending to some urgent activity, etc., which may be situation-dependent based on the patient's environment. Likewise, a similar list of manual intervention usage scenarios may also be implemented from the standpoint of a clinician in some embodiments. In view of the foregoing, it should be appreciated that myriad variations and independent combinations of therapy and/or AV session modulations may be achieved in accordance with the teachings herein. For example, similar to the scenario set forth in FIG. 19B, an embodiment may be configured to allow to still have an AV session but the therapy communications may be prevented while in that state. In another scenario, both AV communications and therapy communications may be paused (independently) until either or both are resumed (independently).

Figure 20:
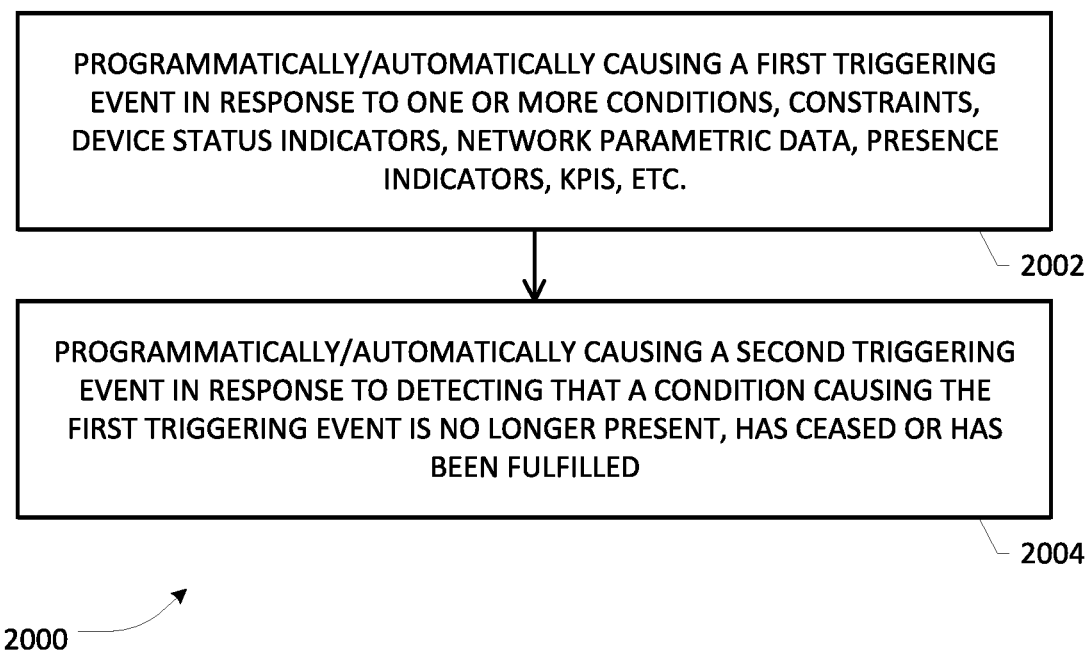
FIG. 20 depicts a flowchart illustrative of blocks, steps and/or acts that may be (re)combined in one or more arrangements with or without additional flowcharts of the present disclosure for facilitating remote care therapy intervention according to still further embodiments.

FIG. 20 depicts a flowchart illustrative of blocks, steps and/or acts that may be (re)combined in one or more arrangements with or without additional flowcharts of the present disclosure for facilitating remote care therapy intervention according to still further embodiments wherein knowledge-based therapy session intervention may be implemented either independently or in combination with a manual intervention scheme. Process flow 2000 sets forth automatically or programmatically causing a first triggering event to pause a remote therapy session in response to detecting, monitoring, observing or otherwise obtaining one or more device conditions, third-party triggering events, constraints, device status indicators, network parametric data, presence indicators, network key performance indicators or KPIs, etc., as set forth at block 2002. A non-exhaustive list of such conditions, status indicators, KPIs, etc. may include incoming phone/video calls, emails, prioritized message notifications, whether the user (i.e., the clinician or the patient) is within a field of view or FoV of the camera or auxiliary AV equipment, whether the user is within the respective environment and/or within a certain distance from the respective controller device, low battery status of either the patient or clinician controller devices, network bandwidth conditions, QoS of A/V communication channels, signal-to-interference or signal-to-noise conditions associated with the network connection used in effectuating the remote care session, device resources, and so on. At block 2004, a second triggering event may be automatically or programmatically caused in response to detecting or determining that a condition causing the first triggering event is no longer present, has ceased or has been fulfilled, whereby the paused remote therapy session may be resumed. In some embodiments, AI/ML techniques may be implemented in conjunction with Big Data analytics for intelligently controlling remote therapy intervention depending on the contextual situation of the patient and/or the clinician. For example, although a clinician may not be within the FoV of the camera, it is possible that the clinician is not outside the clinician's room, and therefore the remote therapy session need not be paused. On the other hand, it may be preferable that when a patient is not in the FoV, therapy be suspended. Some example embodiments may therefore help eliminate the possibility of inadvertent therapy changes or adjustments when the patient is not in video view for some reason by causing automatically triggered pausing.

Additionally, automatic triggering schemes and manual intervention schemes may be combined in various permutations and combinations wherein manual overrides or programmatic overrides may be provided depending on algorithmic control in further embodiments. Accordingly, a broad range of remote care therapy intervention scenarios may be implemented within the ambit of the present patent disclosure, wherein the pausing of the remote care therapy session is operative to prevent the clinician from making changes or (re)adjustments with respect to the programming of the patient's IMD until the session is resumed.

FIGS. 21A-21F depict flowcharts illustrative of blocks, steps and/or acts that may be (re)combined in one or more arrangements with or without additional flowcharts of the present disclosure for implementing remote care therapy intervention in some example embodiments. Process flow 2100A depicted in FIG. 21A exemplifies a methodology executed at a patient controller device relative to a patient-paused scenario. At block 2102, a remote therapy session is established between a clinician and a patient and a Therapy Mode variable or parameter is set to "Active". At block 2104, a determination may be made as to whether a pause button of the patient controller device is pressed. If so, a Boolean comparison of Therapy Mode is made against "Paused" (block 2106), as indicated by the "==" logic operator, which may be repeated as long as the logic operation is valid, as set forth by a flow control return path to block 2104. Otherwise, a further determination is made at block 2108 as to whether a resume button of the patient controller device is activated. If so, a Boolean comparison of Therapy Mode is verified against "Paused" (block 2110). If the Boolean value of the comparison at block 2110 is false, or if no resume button was pressed (block 2108), flow control may return to block 2104. On the other hand, responsive to validating the Boolean comparison of Therapy Mode to "Paused" in block 2110, a "resume remote therapy" command may be generated by the patient controller application, which may be transmitted to the clinician controller application executing on the clinician device, as set forth 2112. At block 2114, a determination is made whether an acknowledgement response, e.g., "Resume Ack", is received from the clinician device, which may be executed in a loop until the "Resume Ack" response message is received. Thereafter, Therapy Mode may be set to "Active", whereupon the flow control returns to block 2104.

Responsive to verifying that the Boolean value of Therapy Mode comparison is false at block 2106, a "pause remote therapy" command may be generated by the patient controller application, which may be transmitted to the clinician controller application executing on the clinician device, as set forth 2118. Similar to block 2114, a decision loop process may be executed until a determination is made that a "Pause Ack" response message is received from the clinician device, as set forth at block 2120. Thereafter, Therapy Mode may be set to "Paused", whereupon the flow control returns to block 2104.

Figure 21A:
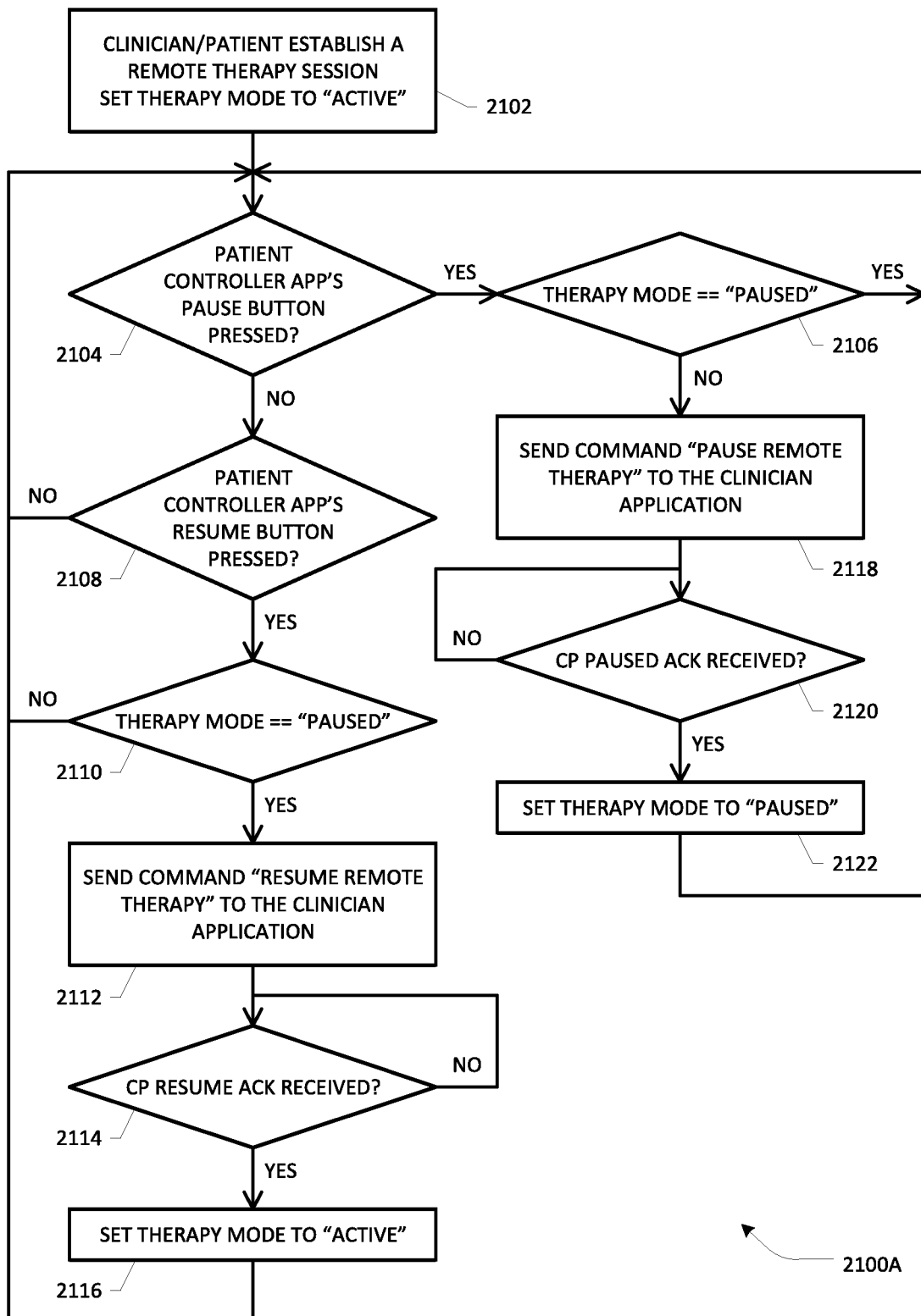
FIGS. 21A-21F depict flowcharts illustrative of blocks, steps and/or acts that may be (re)combined in one or more arrangements with or without additional flowcharts of the present disclosure for facilitating remote care therapy intervention in some use case scenarios according to example embodiments.
Figure 21B:
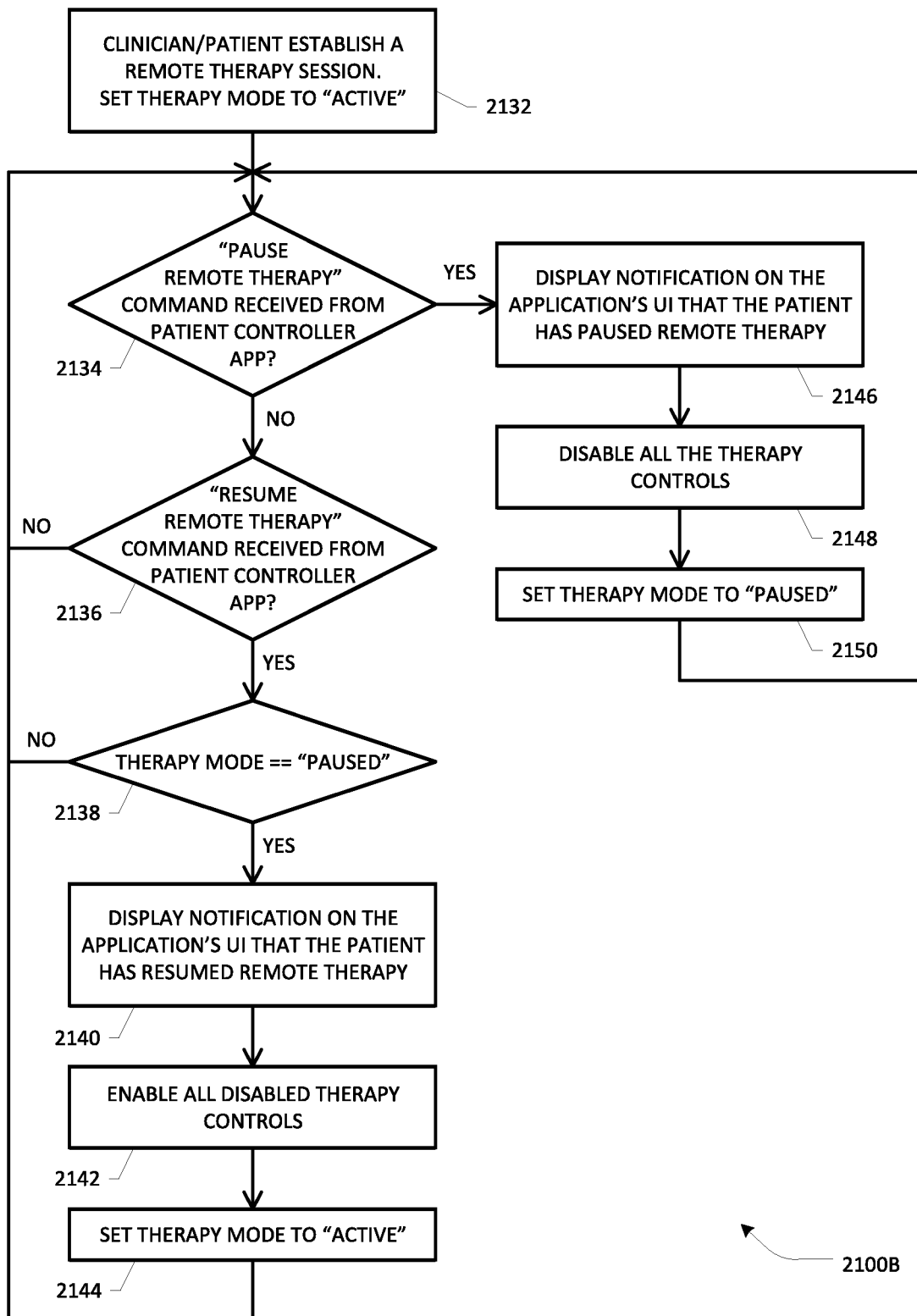

Process flow 2100B depicted in FIG. 21B exemplifies a methodology executed at a clinician controller device responsive to a patient-paused scenario. At block 2132, a remote therapy session is established between a clinician and a patient and a Therapy Mode variable is set to "Active". At block 2134, a determination may be made as to whether a "Pause remote therapy" command is received from the patient controller/application. If so, a notification may be displayed on the clinician controller's GUI that the patient has paused the remote therapy (block 2146). Thereafter, all remote therapy controls may be disabled in an example embodiment, as set forth at block 2148. Further, Therapy Mode may be set to "Paused" (block 2150), whereupon the flow control returns to block 2134.

Responsive to determining that "Pause remote therapy" command was not received from the patient controller/ application at block 2134, a further determination may be made as to whether a "Resume remote therapy" command was received from the patent controller device (block 2136). If so, a Boolean comparison of Therapy Mode is checked against "Paused" (block 2138). If the Boolean value is returned false or if "Resume remote therapy" command was not received from the patent controller device, the flow control returns to block 2134. On the other hand, if the Boolean value is verified as true at block 2138, a notification may be displayed on the clinician controller's GUI that the patient has resumed the remote therapy (block 2140). Thereafter, all disabled remote therapy controls may be enabled in an example embodiment, as set forth at block 2142. Further, Therapy Mode may be set to "Active" (block 2144), whereupon the flow control returns to block 2134.

Figure 21C:
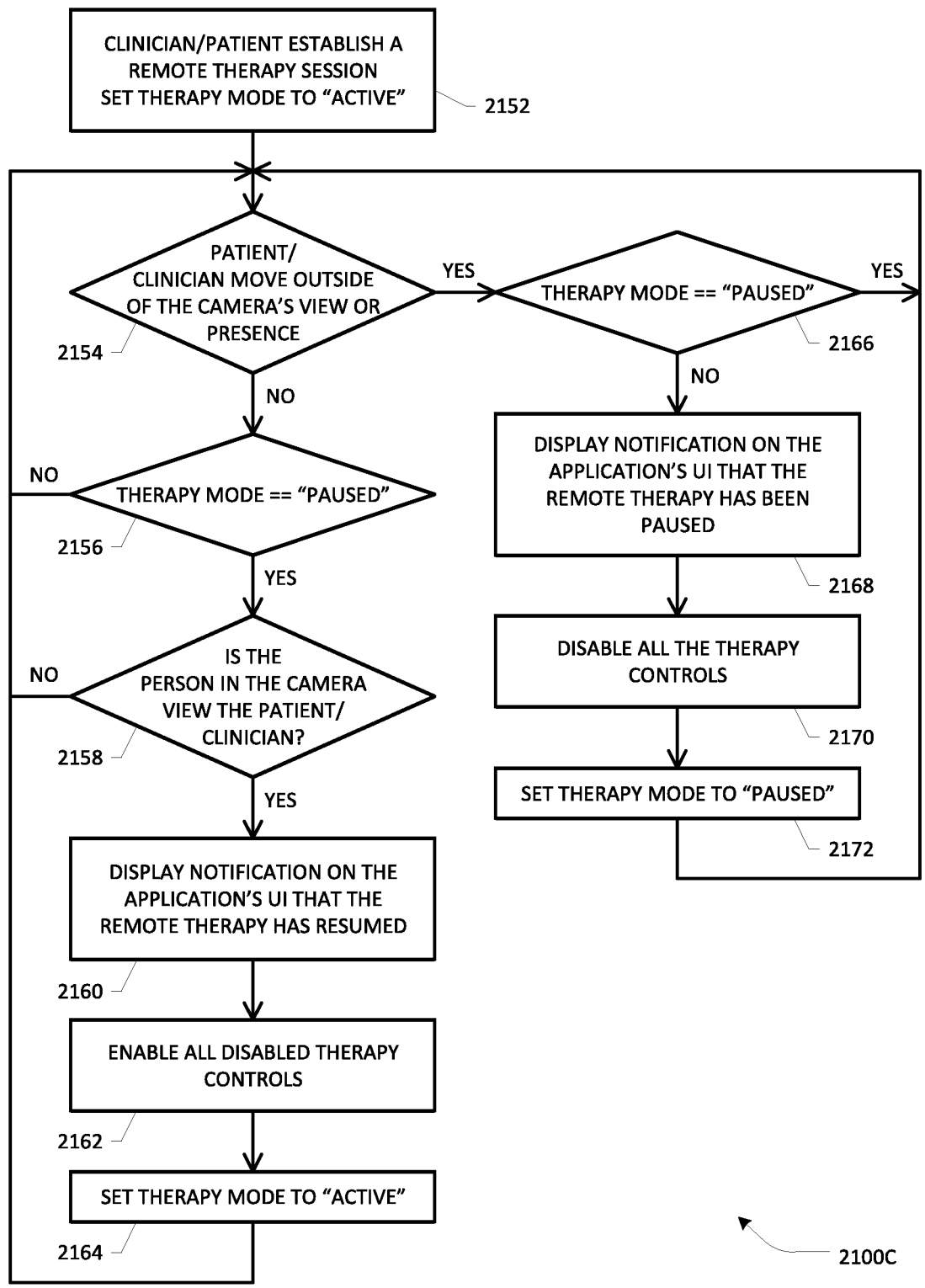

Process flow 2100C depicted in FIG. 21C exemplifies a pause/resume methodology relative to a scenario based on user's presence in a camera view. Similar to example embodiments set forth above, a remote therapy session is established between a clinician and a patient and a Therapy Mode variable is set to "Active" (block 2152). At block 2154, a determination may be made as to whether a user (i.e., the clinician or the patient) moved outside of the camera's view or other presence detector. If so, a Boolean comparison of Therapy Mode is checked against "Paused" (block 2166). If the Boolean value is true, the flow control returns to block 2154. Otherwise, a notification may be displayed on the user controller's GUI that the remote therapy has been paused (block 2168), followed by disabling of the therapy setting controls (block 2170). Thereafter, Therapy Mode may be set to "Paused" (block 2172) and the flow control is returned to block 2154.

At block 2156, a Boolean comparison of Therapy Mode is verified against "Paused". If true, a determination may be made whether the user is in the camera view (block 2158). If the Boolean value is false or if the user is not in the camera view, the flow control returns to block 2154. On the other hand, if the user is determined to be in the camera view or otherwise present, a notification may be displayed on the user controller's GUI that the remote therapy has resumed (block 2160). Thereafter, all disabled remote therapy controls may be enabled in an example embodiment, as set forth at block 2162. Further, Therapy Mode may be set to "Active" (block 2164), whereupon the flow control returns to block 2154.

Figure 21D:
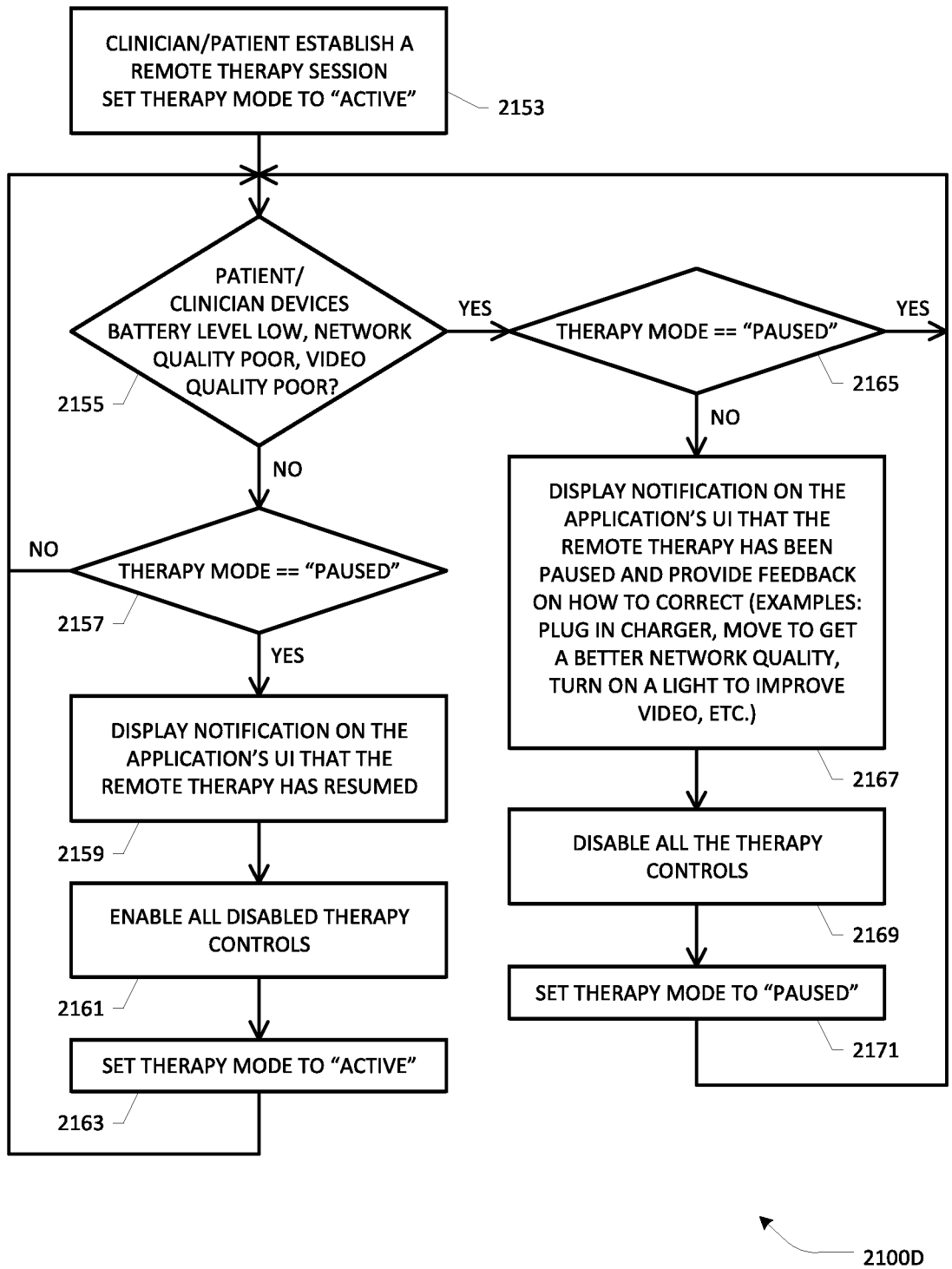
Figure 21E:
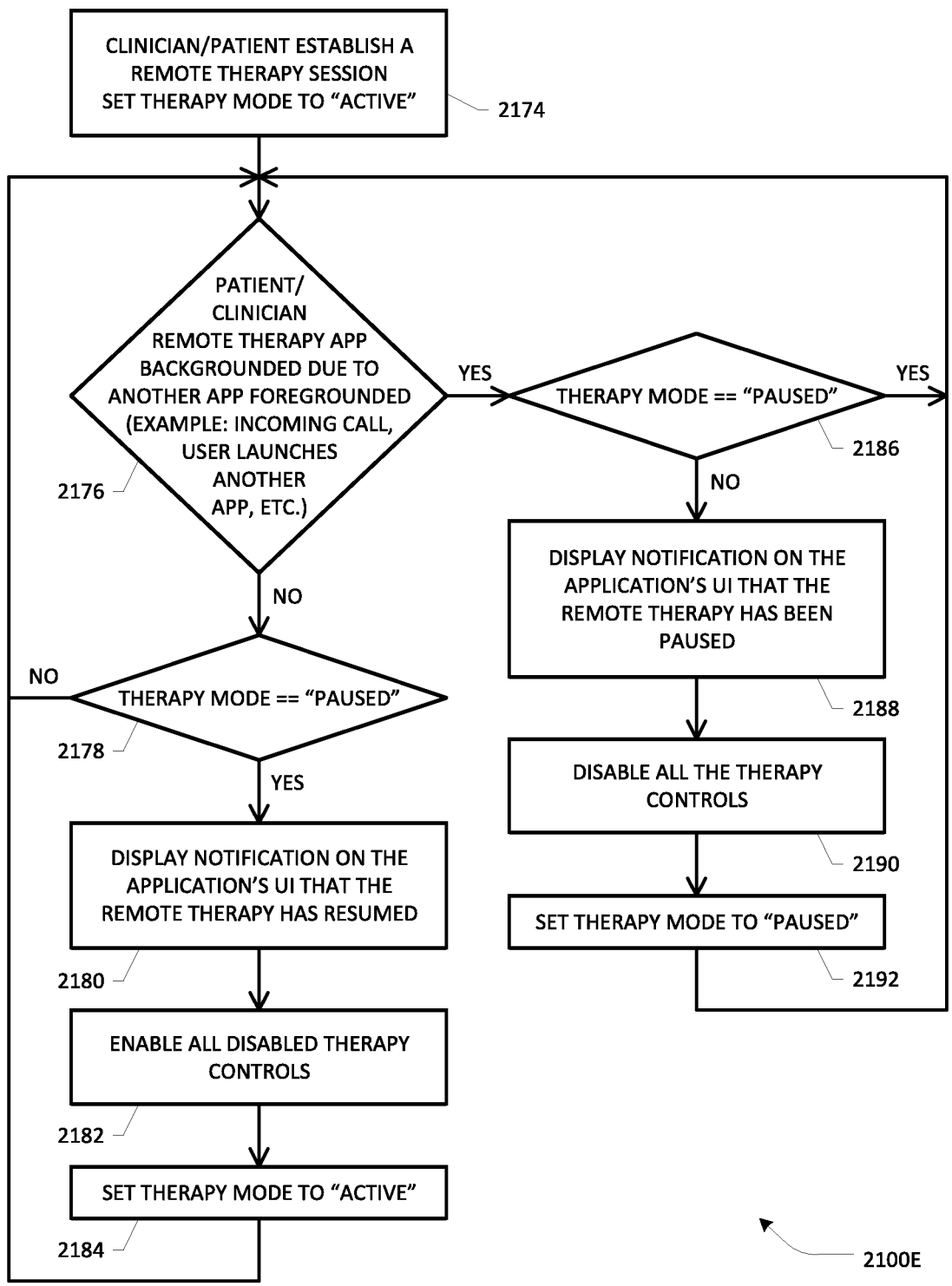
Figure 21F:
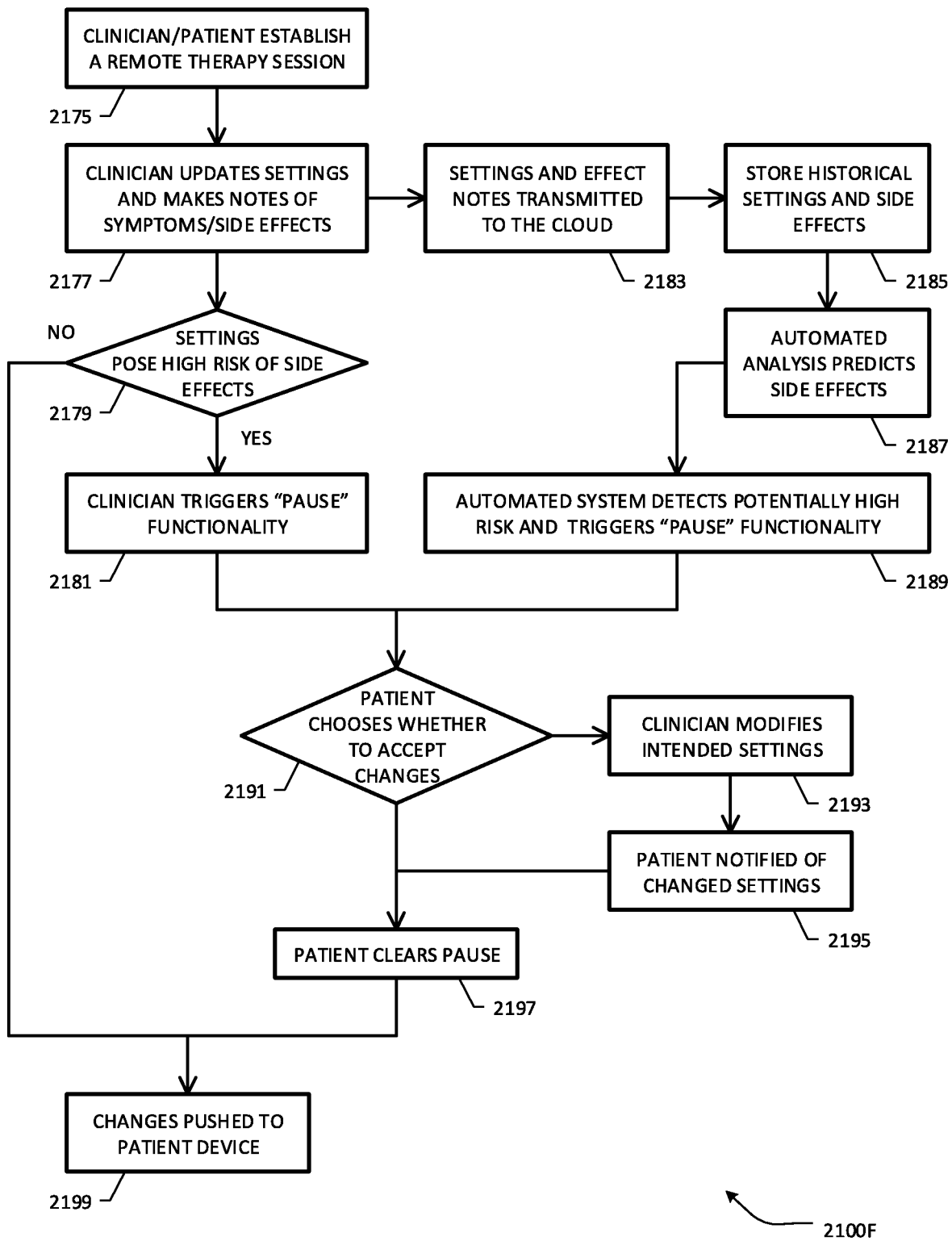

Similar process flows are set forth in FIGS. 21D and 21E with respect to pause/resume schemes based on triggering events generated responsive to network system parametrics, device status, another software application becoming active or foregrounded, etc. Process flow 2100D depicted in FIG. 21D commences with establishing a remote therapy session between a clinician and a patient and setting a Therapy Mode variable to "Active" (block 2153). At block 2155, a determination may be made as to whether any conditionality, constraint, threshold, etc. relative to network/system parametrics or device status is satisfied (e.g., clinician programmer or patient controller battery is low, network quality or audio/video quality is poor, and the like). If so, a Boolean comparison of Therapy Mode is made against "Paused" (block 2165). If the Boolean value is true, the flow control returns to block 2155. Otherwise, a notification may be displayed on the user controller's GUI that the remote therapy has been paused (block 2167), which may be accompanied by generating appropriate messages or feedback signals on how to correct the existing conditionality or constraint. Examples of such feedback messages may include, without limitation, "plug in charger", "move to obtain better network quality", "turn on light to improve video", and the like, depending on the triggering events. As before, the therapy setting controls may be disabled in some embodiments (block 2169). Thereafter, Therapy Mode may be set to "Paused" (block 2171) and the flow control is returned to block 2155.

At block 2157, a Boolean comparison of Therapy Mode is verified against "Paused". If the Boolean value is false, the flow control returns to block 2155. On the other hand, if the Boolean value is true, a notification may be displayed on the user controller's GUI that the remote therapy has resumed (block 2159). Thereafter, all disabled remote therapy controls may be enabled in an example embodiment, as set forth at block 2161. Further, Therapy Mode may be set to "Active" (block 2163), whereupon the flow control returns to block 2155.

Process flow 2100E depicted in FIG. 21E describes a pausing/resuming scenario relative to a remote therapy application being backgrounded. At block 2174, a remote therapy session is established between a clinician and a patient and a Therapy Mode variable is set to "Active". At block 2176, a determination may be made as to whether the remote therapy application on either the clinician programmer or the patient controller has become backgrounded due to another application becoming foregrounded (e.g., an incoming call at the user device, the user launching another application, etc.), as set forth at block 2176. If so, a Boolean comparison of Therapy Mode is checked against "Paused" (block 2186). If the Boolean value of the comparison is true, the flow control returns to block 2176. Otherwise, a notification may be displayed on the user controller's GUI that the remote therapy has been paused (block 2188). As before, the therapy setting controls of the clinician device may be disabled in some embodiments (block 2190). Thereafter, Therapy Mode may be set to "Paused" (block 2192) and the flow control is returned to block 2176.

At block 2178, a Boolean comparison of Therapy Mode is verified against "Paused" after determining that the remote therapy application has not been backgrounded at either of the user devices. If the Boolean value is false, the flow control returns to block 2176. On the other hand, if the Boolean value is true, a notification may be displayed on the user controller's GUI that the remote therapy has resumed (block 2180). Thereafter, all disabled remote therapy controls may be enabled in an example embodiment, as set forth at block 2182. Further, Therapy Mode may be set to "Active" (block 2184), whereupon the flow control returns to block 2176.

In yet another embodiment, a pause/resume process flow may be configured to allow either the clinician or an automated/expert system to trigger the pause functionality, allowing the patient to prepare for, and explicitly accept resumption of the remote care therapy session prior to any therapy changes taking effect. A scenario where such a methodology would be useful is if the clinician wants to try out therapy settings that may potentially cause some side effects, which might bring distress to the patient if they occur unexpectedly. Process flow 2100F depicted in FIG. 21F exemplifies an embodiment relative to the foregoing scenario, which commences with establishing a remote therapy session is established between a clinician and a patient (block 2175). At block 2177, the clinician may update the therapy settings and may take note of potential symptoms and/or side effects of the therapy settings. A parallel branch flow may emanate thereafter, wherein some of the steps, acts, or blocks may be optional and implementation-specific. In one variation, a determination may be made whether the settings pose a risk of side effects at a level that is greater than a designated level, which may be configurable and may be subjectively determined by the clinician (block 2179). If the settings are determined not to pose a high risk of side effects, the therapy settings may be pushed to the patient device (block 2199). On the other hand, if the settings engender side effects at an unacceptable risk level, the clinician may trigger the pause functionality (block 2181), whereupon a query or notification may be sent to the patient to determine whether the patient is willing to accept the risk of the potential side effects of the therapy changes/settings. If the patient chooses to accept the risk level (e.g., based on informed consent), the patient may clear the pause, as set forth at blocks 2191, 2197, whereupon the therapy changes/settings may be transmitted to the patient device (block 2199). An iterative process flow may be configured wherein the clinician may sequentially change/readjust the intended therapy settings and query the patient whether the changes are acceptable until the patient clears the pause based on informed consent with respect to a modified setting. A simplified flow relative to such interactions is exemplified at blocks 2193, 2195, leading to the patient clearing the pause condition (block 2197) and the accepted changes being pushed to the patient device (block 2199).

In an additional/alternative variation, the intended therapy changes/settings and potential side effects noted by the clinician may be transmitted to a cloud-based expert system, which may store the data and perform data analytics to determine/predict a risk factor associated with the therapy changes/settings, as set forth at blocks 2183, 2185, 2187. An automated trigger may be generated to pause the session responsive to the expert system detecting or determining a high risk level associated with the therapy settings (block 2189). The patient may be notified and queried thereafter with respect to the intended therapy changes/settings in view of the risk levels assessed by the expert system until the patient accepts the updated therapy changes/settings and clears the pause condition, similar to the process flow set forth above, whereupon the accepted therapy changes/settings may be transmitted to the patient device (block 2199). Regardless of whether the risk levels associated with any intended therapy changes/settings are evaluated subjectively by the clinician or objectively by the expert system, and regardless of whether the pause is triggered by the clinician or by the expert system, however, the patient may continue to retain ultimate control over the session and may even terminate the session in some use case scenarios. For example, if the patient is not willing to accept any therapy setting changes even after several rounds of negotiation to obtain informed consent, the patient may exit the therapy session and may notify the clinician accordingly.

In some embodiments, either the patient controller application and/or the clinician controller application may be configured to effectuate appropriate UI controls at respective controller devices to facilitate the labeling of various pieces of AV data, contextual data and experiential data related to a remote care therapy session, wherein several types of textual, pictogrammatic, speech- or sound-based labels may be used to characterize the data based on a user's subjective or personal evaluation or experience. Such functionality is particularly advantageous in obtaining highly granular and contextualized data relating to remote care therapy, which may be utilized in training AI/ML-based models, algorithms, expert systems, etc., that may be configured as highly reliable digital or virtual healthcare agents, augmenting and assisting human healthcare providers in current or future therapy sessions according to some implementations.

Figure 22:
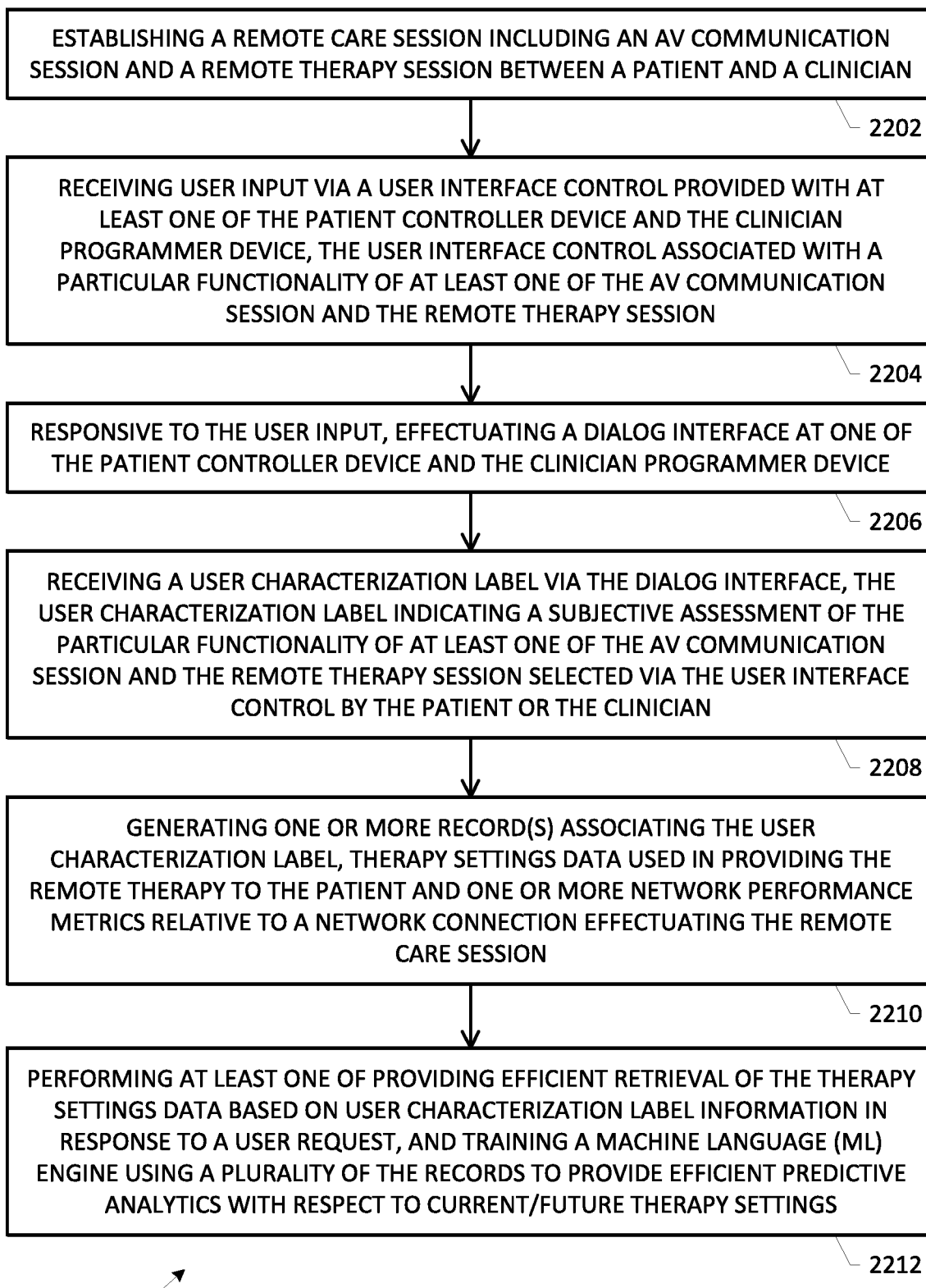
FIG. 22 depicts a flowchart illustrative of blocks, steps and/or acts that may be (re)combined in one or more arrangements with or without additional flowcharts of the present disclosure for facilitating user characterization of AV data and contextual data in remote care therapy according to still further embodiments.

FIG. 22 depicts a flowchart illustrative of blocks, steps and/or acts that may be (re)combined in one or more arrangements with or without additional flowcharts of the present disclosure for facilitating user characterization of AV data and contextual data in remote care therapy according to some embodiments, which may be executed at a patient controller device and/or a clinician controller device (cumulatively referred to as first or second external medical controller devices), and/or at a network entity, under control of suitable program instructions. Process flow 2200 is exemplified with establishing a remote care session including an AV communication session/channel and a remote therapy session/channel between a patient and a clinician at block 2202. At block 2204, user input may be received via a user interface control provided with at least one of the patient controller device and the clinician programmer device, the user interface control associated with a particular functionality of at least one of the AV communication session and the remote therapy session. In some embodiments, such user input may comprise tactile input, e.g., tapping, pressing, double-tapping, swiping, etc., provided at a particular location of the GUI that is presented the user device's touch screen display. At block 2206, responsive to the user input, a dialog interface may be effectuated at the user's device, i.e., at least one of the patient controller device and the clinician programmer device. At block 2208, a user characterization label may be received via the dialog interface, the user characterization label indicating a subjective assessment of the particular functionality of at least one of the AV communication session and the remote therapy session selected via the user interface control by the user, i.e., the patient or the clinician. In some embodiments, database records may be generated associating the user characterization labels, therapy settings data used in providing the remote therapy to the patient and one or more network performance metrics relative to a network connection effectuating the remote care session. In some embodiments, such records may be generated at different times during a therapy session depending on how often a patient or clinician activates a UI control and inputs a label, thereby maintaining a chronological history of the labeled data. In some embodiments, user-labeled data records may be generated at a patient controller device, a clinician controller device, and/or at a network entity, wherein a record generator may be provided for tagging, mapping and/or indexing the data based on the labels. The foregoing acts are set forth at block 2210. In some embodiments, process flow 2200 may involve providing or otherwise facilitating the storage and/or efficient retrieval of the therapy settings data based on user characterization label information in response to a user request, e.g., a request from the clinician. In some embodiments, process flow 2200 may involve training an AI/ML engine using the labeled data records to provide more reliable predictive analytics with respect to future therapy settings. The foregoing acts are set forth at block 2212. It should be appreciated that a remote healthcare AI/ML engine that may be trained based on user-labeled data may be provided with a patient controller device, (e.g., operative in association with a patient controller remote care application), a clinician programmer device (e.g., operative in association with a clinician controller remote care application), or with a network entity (e.g., operative in association with RCSM functionality), or in a combination thereof, depending on the device and/or system architecture implementation according to some embodiments.

Figure 24B:
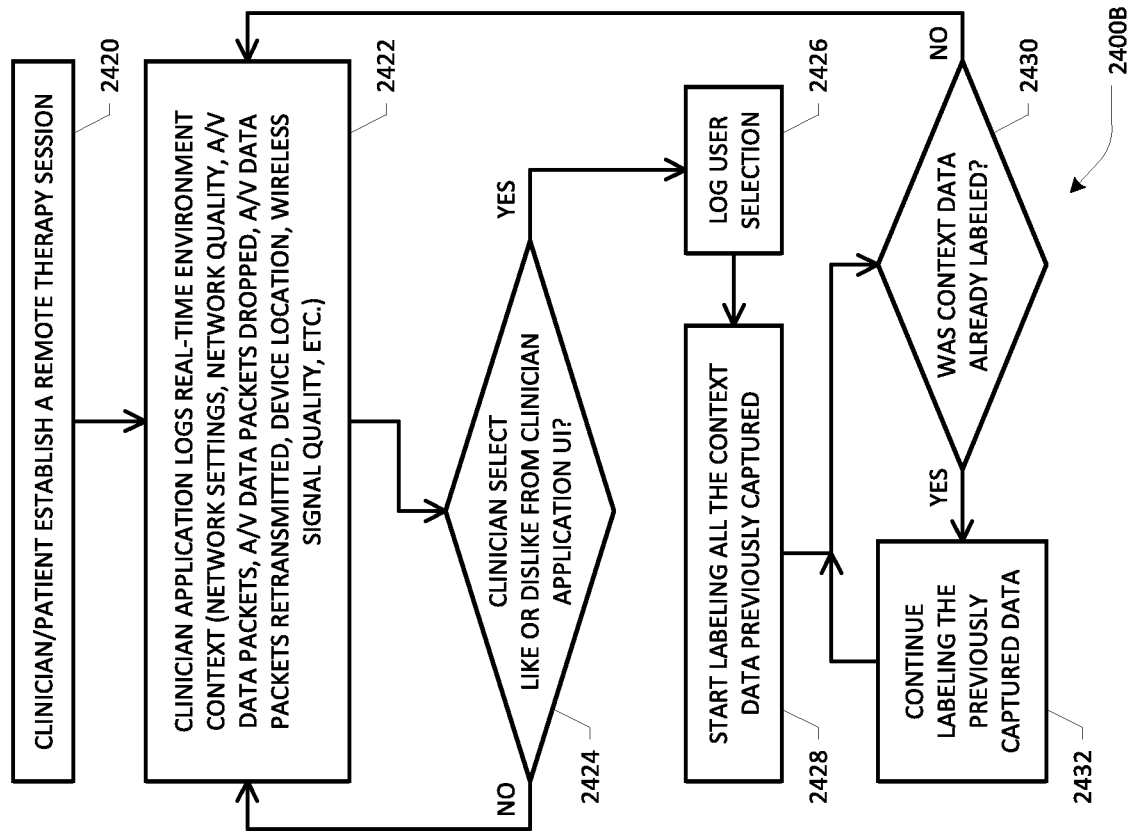
FIGS. 24A and 24B depict an example user interface and associated method to facilitate data labeling according to an example embodiment.
Figure 24A:
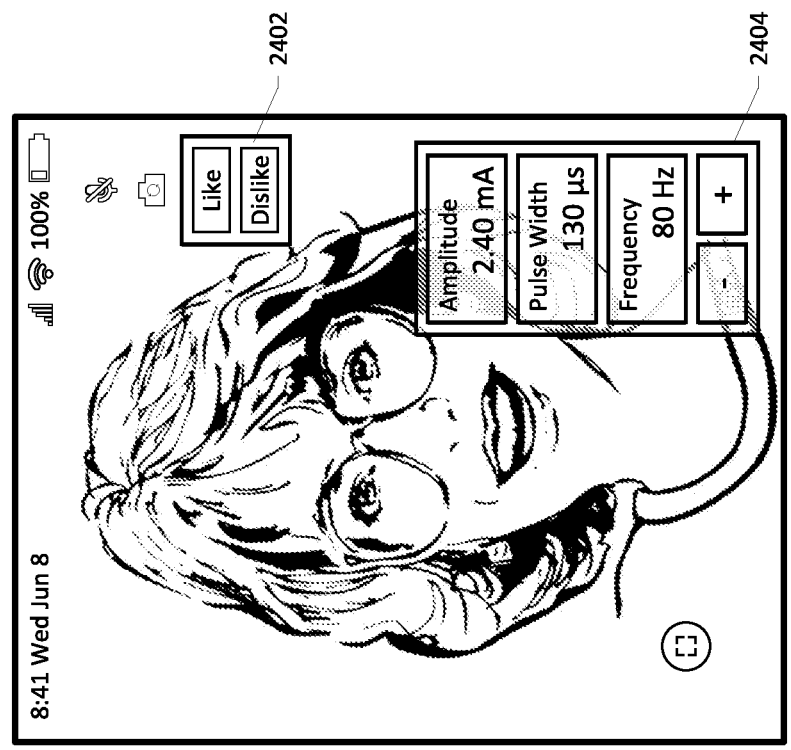

Turning to FIGS. 24A and 24B, depicted therein are an example user interface and associated method to facilitate data labeling by a user according to an example embodiment. A GUI screen 2400A associated with a clinician device is set forth in FIG. 24A along with a corresponding process flow 2400B in FIG. 24B for enabling a clinician to label, index, or mark AV data, therapy settings and events of a therapy session. Skilled artisans will appreciate, however, that similar UI arrangements and process flows may also be provided with a patient controller device, mutatis mutandis, in further embodiments. During a remote therapy session, the clinician can initiate a data labeling request by utilizing a specific portion of the touch screen display, which may show a therapy settings panel 2404 as well as various AV communication controls. Responsive thereto, one or more labeling buttons such as, e.g., "like" or "dislike" buttons, may be presented in a panel 2402. Additionally, speech can be used to label the data, wherein a speech monitoring service associated with the clinician controller application may be configured to monitor the clinician's speech and the context (e.g., based on voice recognition and speech analysis) for positive and negative words such as, e.g., "nice", "good", "like", "hate", "dislike", "terrible", etc. Regardless of the type of labels implemented and/or how they are input, the labels may be used to mark the selected underlying aspect of the remote care therapy, e.g., AV quality, capture of patient responses to specific therapy settings, which may comprise motor responses and/or vocalization responses, and the like.

Process flow 2400B may commence with establishing a remote care session including an AV communication session and a remote therapy session between a patient and a clinician, as set forth at block 2420. In one arrangement, the clinician controller application may be configured to monitor and log various network conditions, performance metrics, etc., during the remote care session. As set forth at block 2422, real-time network environment context data including network settings, network quality, AV packet transmission parametrics including data packets dropped, device location, packet jitter/latency, wireless signal quality, etc., may be monitored and logged. At block 2424, a determination is made if there is an input of label selection by the clinician, which may comprise a user characterization label including at least one of a textual label, a voice label, a ranking label, a multi-category label, a binary category label, a graphic icon label, an emoji label, a gesture-based label and a sliding scale label, among others. The label input is logged and applied to the real-time network environment context data captured, as set forth at blocks 2426 and 2128. If the context data was already captured and labeled (block 2430), the flow control may return to block 2422 for subsequent monitoring and logging. Otherwise, process flow 2400B continues to label the captured but as yet unlabeled context data, as set forth at block 2432.

Figure 25:
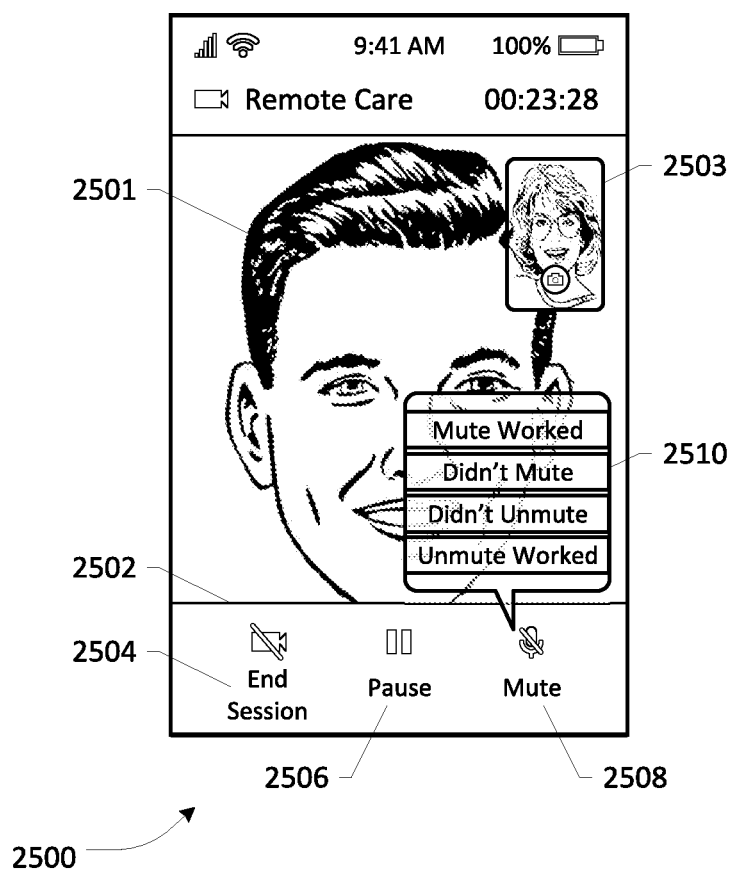
FIGS. 25-27 depict additional user interface representations with respect to facilitating data labeling or characterization by a user according to still further embodiments.
Figure 26:
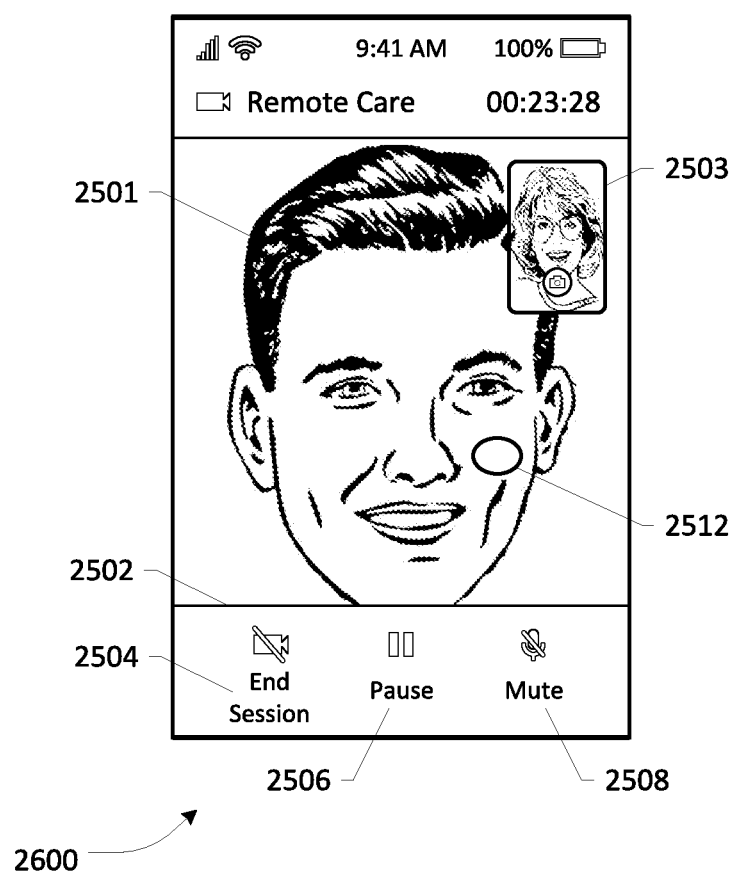
Figure 27:
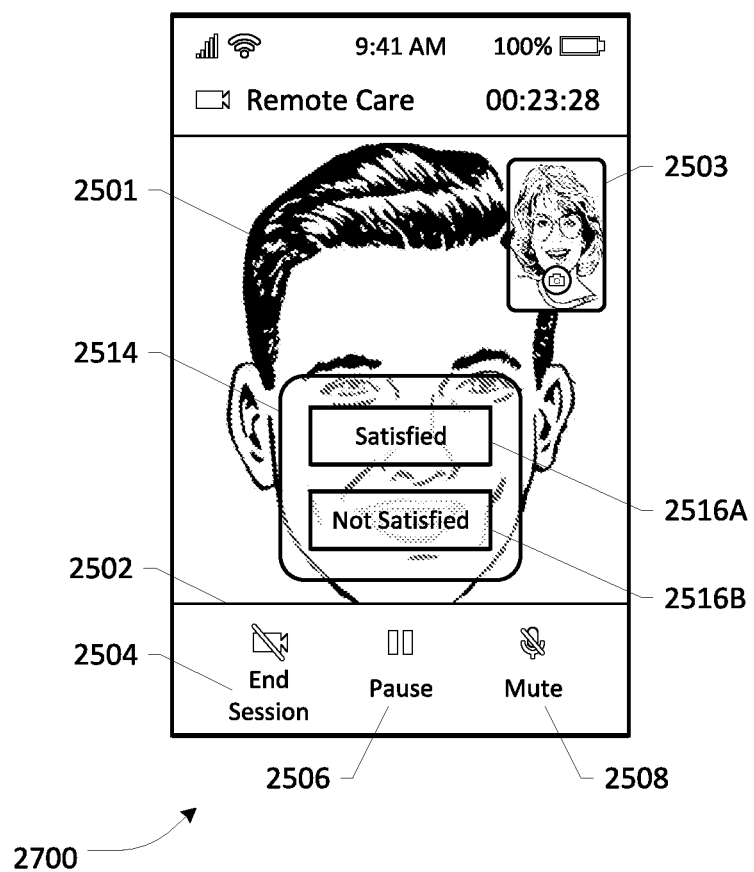

FIGS. 25-27 depict additional user interface representations with respect to facilitating data labeling or characterization by a user according to some example embodiments. A GUI display screen 2500 set forth in FIG. 25 is similar to the GUI display screen 1600C associated with a patient device set forth in FIG. 16C, which is further augmented with one or more label selection windows that may be associated with specific AV communication controls in one arrangement. As before, GUI display screen 2500 may be configured to show the patient and clinician images in a PIP display 2501/2503. Also, a control panel 2502 provided as an overlay or part of GUI display screen 2500 may include icon representations of a video session control 2504, a pause/resume control 2506 and a sound/microphone control 2508. By pressing and holding a particular control icon (e.g., for a configurable amount of time, with a certain amount of pressure, etc.), a pop-up window 2510 may be effectuated, allowing a label selection input specific to the underlying functionality of the control. In some embodiments, the label selection window 2510 may comprise pre-populated labels or selections, which may be periodically updated or reconfigured (based on adaptive learning, for example). For instance, with respect to sound/microphone control 2508, example labels may comprise "Mute Worked", "Did Not Mute", Did Not Unmute", and "Unmute Worked", etc.

FIG. 26 depicts a GUI display screen 2600 similar to the GUI display screen 2500, which is augmented with functionality for labeling an aspect of the therapy session by touching/pressing a particular X-Y coordinate location on the screen. For example, when the user presses, touches and/or holds a location 2512, the user controller application may be configured to notify the user to provide a label, e.g., a verbal label, a gesture label, etc. Such labels may be translated to text and the X-Y location may be analyzed to determine applicable control functionality associated therewith. The textualized label may be applied to the control functionality, which may be done with a configurable time offset, e.g., applied to the functionality at X seconds prior to triggering the label, to account for any delay.

FIG. 27 depicts a similar GUI display screen 2700 associated with a user controller device, which is augmented with functionality for facilitating context labeling based on monitoring the network environment. For example, responsive to monitoring real-time network conditions and user's interactions during the therapy, a pop-up notification window 2514 may be presented to the user. The user may be prompted to provide a response to indicate if a previous action attempted by the user was executed or performed in an acceptable manner, which may be indicated by selecting a pre-populated label such as, e.g., "Satisfied", "Unsatisfied", etc. Some example labeling scenarios may include, without limitation, (i) detecting that user had to press a control twice or more before the command associated with the control was completed; (ii) time to complete a remote command taking longer than expected; (iii) observing packet loss of video/audio data during a remote care session, etc. Responsive to obtaining the user's selection of the label, the selected label is applied against the monitored context data, which may be stored or presented to Big Data analytics for data mining, AI/ML model training, etc.

It should be appreciated that example embodiments set forth above advantageously provide a mechanism wherein A/V video stream data may be labeled within the context of a clinical evaluation in some scenarios. For example, software buttons such as "like" or "dislike" buttons may be replaced with buttons for "tremor", "bradykinesia", or "dyskinesia", etc., which provides for the additional benefit of allowing for the AV segments to be retrieved based on the labeled content. Furthermore, additional and/or external intelligence (e.g., by way of AI/ML algorithms) may also be implemented in some embodiments to automatically supply and/or update labels as noted elsewhere in the present disclosure.

Turning to FIG. 23, depicted therein is a database structure 2300 comprising a plurality of user-labeled data records 2310-1 to 2310-N that may be obtained relative to a remote care service according to an example embodiment. Various pieces of data 2302 may be labeled or indexed according to the teachings herein as noted above, which may include audio quality data 2304-1, video quality data 2304-2, vocalization response capture quality data 2304-3 (pertaining to different types of vocalization responses), motor response capture quality data 2304-N (pertaining to different types of motor responses), etc. Each data item may be tagged with a suitable label, e.g., Label-1 to Label-K, which is associated with or mapped to captured network environment or contextual data 2306 as well as various therapy settings data 2308. In one arrangement, labeled data items may be time-stamped and organized into a chronological database comprising records for one or more remote patients, one or more types of remote care therapies, etc. It should be appreciated that a labeled remote care therapy database as set forth herein therefore includes labeled and time-stamped therapy settings, which can enable a clinician to readily retrieve previous settings data, among others, during a therapy session based on user-supplied labels that are not only more amenable to user recollection but also more representative of verbal, oral, visual or other behavioral cues that may be developed during conventional in-person consultations and therapy administration.

Figure 28:
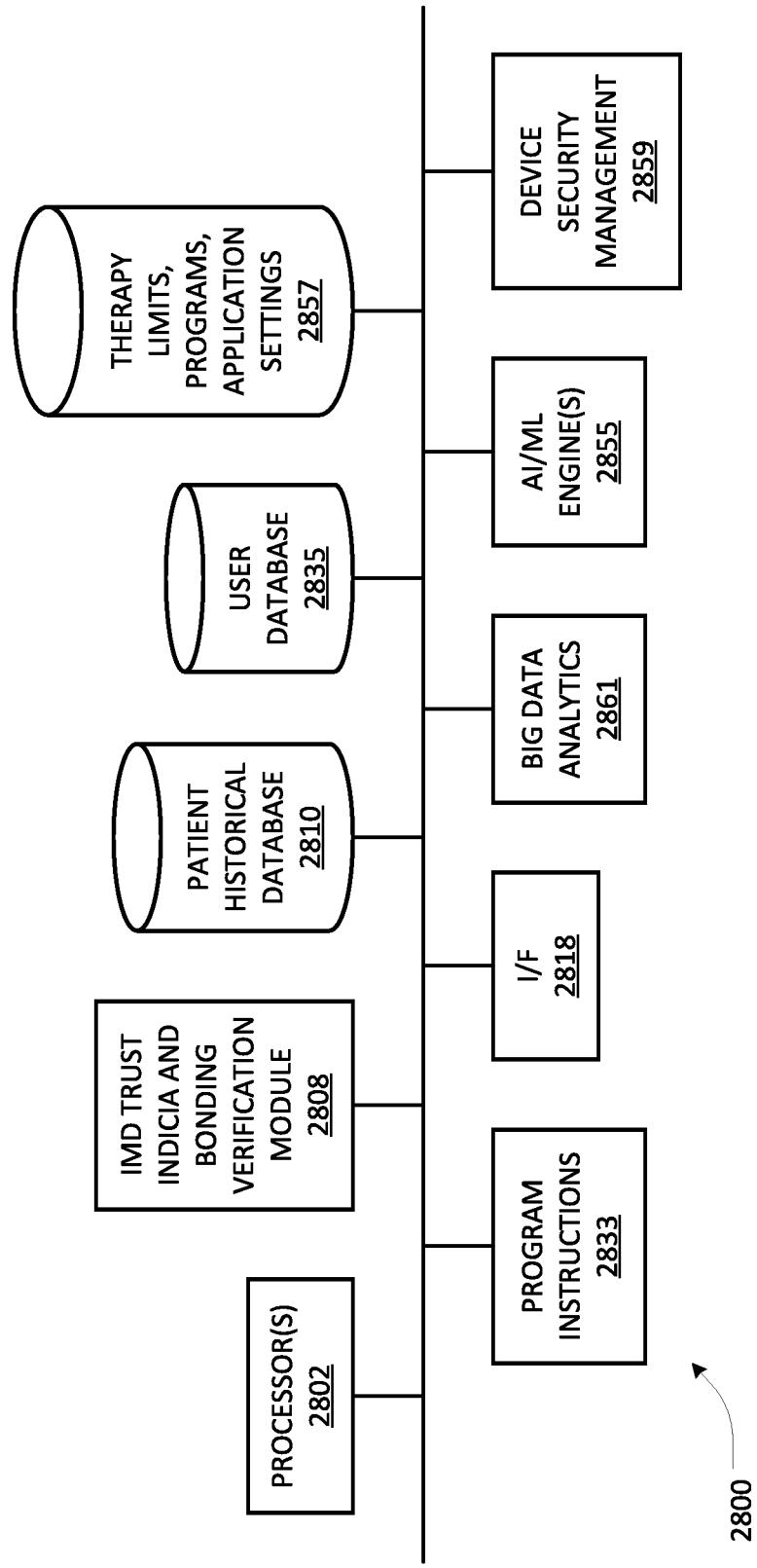
FIG. 28 depicts a block diagram involving a plurality of modules that may be configured or rearranged as a computer-implemented network node, platform or datacenter operative to effectuate one or more systems or methods according to some embodiments of the present disclosure.

FIG. 28 depicts a block diagram involving a plurality of modules that may be configured as a computer-implemented network node, apparatus or platform 2800 operative at a service provider network, a datacenter facility, and/or a cloud operator, etc., which may include remote care session management functionalities for purposes of an example embodiment of the present disclosure. One or more processors 2802 may be operatively coupled to various modules that may be implemented in persistent memory for executing suitable program instructions or code portions (e.g., code portion 2833) with respect to effectuating remote device management, establishment of trusted associations, interfacing with encryption key management systems, and the like, preferably in association with one or more other modules and/or databases of the platform 2800, which may be configured as a distributed architecture in some embodiments. As skilled artisans will recognize, the program instructions or code portions provided as part of the platform 2800 may be configured in a number of ways operative to execute one or more process flows described hereinabove. An IMD trust indicia verification module 2808 may be provided to create, maintain and store bonding associations between IMDs and clinician devices, which may be used for verification/bonding of patient controllers/devices in some embodiments. A patient history database 2810 and a user database 2835 may also be provided in some embodiments wherein the database(s) are operative to maintain and store patients' historical data relating to different therapies, biophysiological conditions monitoring, etc., as well as patient profile data, clinician profile data, and the like. In some arrangements, therapy settings, stimulation application programs, stimulation level thresholds and limits, etc., may be stored in a database 2857, e.g., on a patient-by-patient basis and/or IMD-by-IMD basis, which may also include user-labeled therapy settings and session quality data, wherein the stored data may be made available to remote clinicians engaged in a particular therapy session. As noted previously, user-labeled data may be generated either at patient controllers, clinician programmers, or both, and appropriate user-labeled data records may be generated at either devices and/or at the platform 2800 under control of suitable program instructions configured as a record generator module. Example remote therapy applications supported by the platform 2800 may comprise, without limitation, an SCS therapy, a neuromuscular stimulation therapy, a dorsal root ganglion (DRG) stimulation therapy, a deep brain stimulation (DBS) therapy, a cochlear stimulation therapy, a drug delivery therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial magnetic stimulation (rTMS) therapy, a vagal nerve stimulation (VNS) therapy, and one or more physiological condition monitoring applications, among others.

In some embodiments, a security management module 2859 may be provided as part of the platform 2800 for interfacing and proxying clinician devices and patient devices with respect to corresponding key infrastructure systems as described hereinabove. In a further embodiment, the platform 2800 may include one or more AI.ML engines 2855 operative in association with Big Data analytics module(s) 2861 for facilitating intelligent data-mining operations and adaptive learning of therapy operations based on patients' historical therapy data, biophysiological data, user-labeled data, and other relevant data that may be sourced from external entities. In the context of some example remote care therapy use case scenarios, "Big Data" may be used as a term for a collection of data sets so large and complex that it becomes virtually impossible to process using conventional database management tools or traditional data processing applications. Challenges involving Big Data may include capture, curation, storage, search, sharing, transfer, analysis, and visualization, etc. Because Big Data available with respect to patients' diagnostic data, user profile data, real-time monitoring of patients' biophysiological conditions, Internet-of-Things (IoT)-based sensor data gathered from patients and respective ambient surroundings, environments, etc., can be on the order of several terabytes to petabytes, exabytes, or more, it becomes exceedingly difficult to work with using most relational database management systems for optimizing, ranking, indexing, cross-correlating test/measurement data and status data in typical environments. Accordingly, in one arrangement, the Big Data analytics module 2861 and appropriate therapy domain knowledgebase(s) (not specifically shown in this FIG.) may be implemented in a machine learning framework that is optimized for storage and large-scale processing of data sets on clusters of commodity hardware. Skilled artisans will further recognize that an example machine learning framework may be implemented using one or more ML techniques, processes or algorithms and models (e.g., neural networks) as well as rule-based systems. In general, a variety of techniques such as, e.g., artificial intelligence (AI), convolutional neural networks (CNNs), fuzzy logic learning, pattern recognition, support vector machines (SVMs), support vector networks (SVNs) and related techniques, may be employed in a suitable combination or sub-combination with respect to effectuating an AI/ML-enhanced remote care therapy use case scenario involving the platform 2800. Further, in view of the flexible architecture of the platform 2800, one or more network interfaces (I/F) 2818 may be provided for interfacing with various external nodes or infrastructural elements, e.g., involving access and/or core communications networks, external databases, cryptographic key infrastructure nodes, business support system nodes, third-party healthcare provider networks, and the like.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine, as well as programmable system devices (PSDs) employing system-on-chip (SoC) architectures that combine memory functions with programmable logic on a chip that is designed to work with a standard microcontroller. Example memory modules or storage circuitry may include volatile and/or non-volatile memories such as, e.g., random access memory (RAM), electrically erasable/programmable read-only memories (EEPROMs) or UV-EPROMS, one-time programmable (OTP) memories, Flash memories, static RAM (SRAM), etc.

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Where the phrases such as "at least one of A and B" or phrases of similar import are recited or described, such a phrase should be understood to mean "only A, only B, or both A and B." Reference to an element in the singular is not intended to mean "one and only one" unless explicitly so stated, but rather "one or more." Moreover, the terms "first," "second," and "third," etc. employed in reference to elements or features are used merely as labels, and are not intended to impose numerical requirements, sequential ordering or relative degree of significance or importance on their objects. All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. A method for facilitating remote care management involving a patient having an implantable medical device (IMD), the method comprising:
    establishing a remote care session between a patient controller device associated with the patient and a clinician programmer device associated with a clinician, wherein the clinician and the patient are remotely located with respect to each other and the remote care session includes an audiovisual (AV) communication session controlled by one or more audio controls and one or more video controls provided at the patient controller device and by one or more audio controls and one or more video controls provided at the clinician programmer device, the remote care session further including a remote therapy session for providing one or more programming instructions to the patient's IMD via the patient controller device responsive to determining that the patient requires remote therapy;
    receiving user input via a user interface control provided with at least one of the patient controller device and the clinician programmer device, the user interface control associated with a particular functionality of at least one of the AV communication session and the remote therapy session;
    responsive to the user input, effectuating a dialog interface at one of the patient controller device and the clinician programmer device; and
    receiving a user characterization label via the dialog interface, the user characterization label indicating a subjective assessment of the particular functionality of at least one of the AV communication session and the remote therapy session selected via the user interface control by the patient or the clinician,
    wherein the particular functionality relates to at least one of audio quality of the AV communication session, video quality of the AV communication session, patient motor response capture quality, and patient vocalization capture quality, wherein the dialog interface comprises at least one of an audio dialog window facilitated by voice recognition, a video dialog window for facilitating motion capture and facial recognition, a label tray having a plurality of predetermined labels represented by corresponding software buttons, and a pull-down menu dialog window for facilitating label selection, wherein the user characterization label comprises at least one of a voice label, a ranking label, a multi-category label, a binary category label, a graphic icon label, an emoji label, a gesture-based label and a sliding scale label, and wherein at least the remote therapy session is paused in response to determining that a particular user characterization label has occurred a predetermined number of times over a configurable period of time.

2. The method as recited in claim 1, further comprising generating one or more records associating the user characterization label, therapy settings data used in providing the remote therapy to the patient and one or more network performance metrics relative to a network connection effectuating the remote care session.

3. The method as recited in claim 2, further comprising performing at least one of providing efficient retrieval of the therapy settings data based on user characterization label information in response to a user request, and training a machine language (ML) engine using a plurality of the records to provide efficient predictive analytics with respect to future therapy settings.

4. The method as recited in claim 1, wherein the remote therapy session comprises at least one of a spinal cord stimulation (SCS) therapy, a neuromuscular stimulation therapy, a dorsal root ganglion (DRG) stimulation therapy, a deep brain stimulation (DBS) therapy, a cochlear stimulation therapy, a drug delivery therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial magnetic stimulation (rTMS) therapy, a vagal nerve stimulation (VNS) therapy, and one or more physiological condition monitoring applications.

5. A remote care management system, comprising:
a first external device configured as a clinician programmer device associated with a clinician;
a second external device configured as a patient controller device associated with a patient;
an implantable medical device (IMD) implanted in the patient, the IMD supporting a therapy application configured to be programmable by at least one of the clinician operating the first external device and the patient operating the second external device; and
wherein the first external device and the second external device are each configured to establish a remote care session therebetween, the remote care session configurable to selectively allow a remote therapy session in addition to an audio and video (AV) communication session that facilitates a telehealth consultation between the clinician and the patient, the remote therapy session for delivering one or more programming instructions to the patient's IMD from the clinician programmer device in response to determining that the patient requires remote therapy,
wherein at least one of the patient controller device and the clinician programmer device is provided with a user interface control for receiving user input, the user interface control associated with a particular functionality of at least one of the AV communication session and the remote therapy session,
wherein the at least one of the patient controller device and the clinician programmer device is configured to effectuate, responsive to the user input, a dialog interface at one of the patient controller device and the clinician programmer device,
the dialog interface operative to receive a user characterization label indicative of a subjective assessment of the particular functionality of at least one of the AV communication session and the remote therapy session selected via the user interface control by the patient or the clinician,
wherein the user interface control provided with the at least one of the patient controller device and the clinician programmer device is operative with respect to the particular functionality relating to at least one of audio quality of the AV communication session, video quality of the AV communication session, patient motor response capture quality, and patient vocalization capture quality,
wherein the dialog interface comprises at least one of an audio dialog window facilitated by voice recognition, a video dialog window for facilitating motion capture and facial recognition, a label tray having a plurality of predetermined labels represented by corresponding software buttons, and a pull-down menu dialog window for facilitating label selection,
wherein the user characterization label comprises at least one of a voice label, a ranking label, a multi-category label, a binary category label, a graphic icon label, an emoji label, a gesture-based label and a sliding scale label, and
wherein at least the remote therapy session is paused in response to determining that a particular user characterization label has occurred a predetermined number of times over a configurable period of time.

6. The remote care management system as recited in claim 5, further comprising a record generator module for creating one or more records associating the user characterization label, therapy settings data used in providing the remote therapy to the patient and one or more network performance metrics relative to a network connection effectuating the remote care session.

7. The remote care management system as recited in claim 6, further comprising a database module for performing at least one of providing efficient retrieval of the therapy settings data based on user characterization label information in response to a user request from the clinician or the patient, and training a machine language (ML) engine using a plurality of the records to provide efficient predictive analytics with respect to future therapy settings.

8. The remote care management system as recited in claim 5, wherein the IMD is configured to effectuate a remote care therapy application comprising at least one of a spinal cord stimulation (SCS) therapy, a neuromuscular stimulation therapy, a dorsal root ganglion (DRG) stimulation therapy, a deep brain stimulation (DBS) therapy, a cochlear stimulation therapy, a drug delivery therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial magnetic stimulation (rTMS) therapy, a vagal nerve stimulation (VNS) therapy, and one or more physiological condition monitoring applications.

9. The remote care management system as recited in claim 5, further comprising a remote care session manager configured to maintain a first trusted association between the IMD and the clinician programmer device when the clinician programmer device and the patient are in close proximity of each other, and a second trusted association between the patient controller device and the IMD when the patient controller device and the patient are in close proximity of each other.

10. A non-transitory tangible computer-readable medium having program code stored thereon for execution on a first external medical controller device for facilitating remote care delivery with respect to a patient having an implantable medical device (IMD), the non-transitory tangible computer-readable medium comprising:

a code portion for establishing a remote care session with a second external medical controller device, wherein a clinician and the patient are remotely located with respect to each other and the remote care session includes an audiovisual (AV) communication session controlled by one or more audio controls and one or more video controls provided with at least one of the first and second external medical controller devices, the remote care session further including a remote therapy session for providing one or more programming instructions to the patient's IMD responsive to determining that the patient requires remote therapy;

a code portion for processing a user input received via a user interface control provided with the first external medical controller device, the user interface control associated with a particular functionality of at least one of the AV communication session and the remote therapy session;

a code portion, operative responsive to the user input, for effectuating a dialog interface at first external medical controller device;

a code portion for processing a user characterization label received via the dialog interface, the user characterization label indicating a subjective assessment of the particular functionality of at least one of the AV communication session and the remote therapy session selected via the user interface control by the patient or the clinician, wherein the particular functionality relates to at least one of audio quality of the AV communication session, video quality of the AV communication session, patient motor response capture quality, and patient vocalization capture quality, wherein the dialog interface comprises at least one of an audio dialog window facilitated by voice recognition, a video dialog window for facilitating motion capture and facial recognition, a label tray having a plurality of predetermined labels represented by corresponding software buttons, and a pull-down menu dialog window for facilitating label selection, wherein the user characterization label comprises at least one of a voice label, a ranking label, a multi-category label, a binary category label, a graphic icon label, an emoji label, a gesture-based label and a sliding scale label; and a code portion for pausing the remote therapy session in response to determining that a particular user characterization label has occurred a predetermined number of times over a configurable period of time.

11. The non-transitory tangible computer-readable medium as recited in claim 10, further comprising a code portion for generating one or more records associating the user characterization label, therapy settings data used in providing the remote therapy to the patient and one or more network performance metrics relative to a network connection effectuating the remote care session.

12. The non-transitory tangible computer-readable medium as recited in claim 11, further comprising a code portion for facilitating at least one of efficient retrieval of the therapy settings data based on user characterization label information in response to a user request and training a machine language (ML) engine using a plurality of the records to provide efficient predictive analytics with respect to future therapy settings.

\* \* \* \* \*

UNITED STATES PATENT AND TRADEMARK OFFICE
CERTIFICATE OF CORRECTION

PATENT NO. : 11,133,113 B2
APPLICATION NO. : 16/901368
DATED : September 28, 2021
INVENTOR(S) : Scott DeBates et al.

It is certified that error appears in the above-identified patent and that said Letters Patent is hereby corrected as shown below:

In the Specification

At Column 9, Line number 57, delete "Wth" and replace with --With--.
At Column 10, Line number 2, delete "WMAX" and replace with --WiMAX--.
At Column 15, Line number 5, delete "Wth" and replace with --With--.
At Column 21, Line number 60, delete "Wth" and replace with --With--.

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*